(12) United States Patent
Shimada et al.

(10) Patent No.: US 11,312,767 B2
(45) Date of Patent: Apr. 26, 2022

(54) CROSS-SPECIES ANTI-LATENT TGF-BETA 1 ANTIBODIES

(71) Applicant: Chugai Seiyaku Kabushiki Kaisha, Tokyo (JP)

(72) Inventors: Hideaki Shimada, Singapore (SG); Masakazu Kanamori, Singapore (SG); Xing'er Christine Koo, Singapore (SG)

(73) Assignees: Chugai Seiyaku Kabushiki Kaisha, Tokyo (JP); Chugai Pharmabody Research Pte. Ltd., Singapore (SG)

(*) Notice: Subject to any disclaimer, the term of this patent is extended or adjusted under 35 U.S.C. 154(b) by 0 days.

(21) Appl. No.: 17/466,509

(22) Filed: Sep. 3, 2021

(65) Prior Publication Data

US 2021/0395356 A1 Dec. 23, 2021

Related U.S. Application Data

(63) Continuation of application No. PCT/JP2020/032522, filed on Aug. 28, 2020.

(30) Foreign Application Priority Data

Aug. 28, 2019 (JP) .............................. JP2019-155278

(51) Int. Cl.
| | | |
|---|---|---|
| C07K 16/22 | (2006.01) | |
| C07K 16/30 | (2006.01) | |
| A61P 35/00 | (2006.01) | |
| A61K 45/06 | (2006.01) | |

(52) U.S. Cl.
CPC ............. *C07K 16/22* (2013.01); *A61K 45/06* (2013.01); *A61P 35/00* (2018.01); *C07K 16/30* (2013.01)

(58) Field of Classification Search
None
See application file for complete search history.

(56) References Cited

U.S. PATENT DOCUMENTS

2021/0115122 A1  4/2021  Kanamori

FOREIGN PATENT DOCUMENTS

| WO | WO2005105144 A1 | 11/2005 |
| WO | WO2011102483 A1 | 8/2011 |
| WO | WO2013134365 A1 | 9/2013 |
| WO | WO2014074532 A2 | 5/2014 |
| WO | WO2014182676 A2 | 11/2014 |
| WO | WO2015171691 A2 | 11/2015 |
| WO | WO2016115345 A1 | 7/2016 |
| WO | WO2017156500 A1 | 9/2017 |
| WO | WO2018043734 A1 | 3/2018 |
| WO | WO2018129329 A1 | 7/2018 |
| WO | WO2018206790 A1 | 11/2018 |
| WO | WO2018235964 A1 | 12/2018 |
| WO | WO2019023661 A1 | 1/2019 |
| WO | WO2019045086 A1 | 3/2019 |
| WO | WO2019075090 A1 | 4/2019 |
| WO | WO2019163927 A1 | 8/2019 |
| WO | WO2020014460 A1 | 1/2020 |
| WO | WO2020014473 A1 | 1/2020 |
| WO | WO2020160291 A2 | 8/2020 |
| WO | WO2021039945 A1 | 3/2021 |

OTHER PUBLICATIONS

Lloyd et al., Modelling the human immune response: performance of a 1011 human antibody repertoire against a broad panel of therapeutically relevant antigens. Protein Engineering, Design & Selection, 22, 159-168, 2009. (Year: 2009).*
Annes, J. P., et al., "Making sense of latent TGFβ activation," J Cell Sci., 116:217-224 (2003).
Dickson, M. C., et al., "Defective haematopoiesis and vasculogenesis in transforming growth factor-β1 knock out mice," Development, 121:1845-1854 (1995).
Dubois, C. M., et al., "Processing of Transforming Growth Factor β1 Precursor by Human Furin Convertase," J Biol Chem., 270(18):10618-10624 (1995).
Gabriely, G., et al., "Targeting latency-associated peptide promotes anti-tumor immunity," Sci Immunol., 2(11):eaaj1738 (2017).
Kulkarni, A. B., et al., "Transforming growth factor β1 null mutation in mice causes excessive inflammatory response and early death," Proc Natl Acad Sci., 90:770-774 (1993).
Martin, C. J., et al., "Selective inhibition of TGFβ1 activation overcomes primary resistance to checkpoint blockade therapy by altering tumor immune landscape," Sci Transl Med., 12:eaay8456 (2020).
Massagué, J., "TGF-β Signal Transduction," Annu Rev Biochem. 67:753-791 (1998).
McCartney-Francis, N. L., et al., "TGF-β: A Balancing Act," Intern Rev Immunol., 16:553-580 (1998).
Millan, F. A., et al., "Embryonic gene expression patterns of TGF β1, β2 and β3 suggest different developmental functions in vivo," Development, 111:131-143 (1991).
Munger, J. S., et al., "The Integrin αvβ6 Binds and Activates Latent TGFβ1: A Mechanism for Regulating Pulmonary Inflammation and Fibrosis," Cell, 96:319-328 (1999).

(Continued)

*Primary Examiner* — Elly-Gerald Stoica
(74) *Attorney, Agent, or Firm* — Nixon & Vanderhye P.C.

(57) ABSTRACT

The objective of the invention is to provide cross-species anti-latent TGF-beta 1 antibodies which inhibit a protease mediated activation of latent TGF-beta 1 without inhibiting integrin mediated activation of latent TGF-beta 1. To obtain the anti-latent TGF-beta 1 antibodies of the invention, anti-latent-latent TGF-beta 1 antibodies which inhibit a protease mediated activation of latent TGF-beta 1 without inhibiting integrin mediated activation of latent TGF-beta 1 were screened, and then humanized, and further optimized. The invention also provides combination therapies comprising an anti-latent TGF-beta 1 antibody and one or more immune checkpoint inhibitors, preferably a PD-1 axis binding antagonists.

19 Claims, 13 Drawing Sheets

Specification includes a Sequence Listing.

(56) References Cited

OTHER PUBLICATIONS

Nunes, I., et al., "Structure and activation of the large latent transforming growth factor-β complex," J Am Optom Assoc., 69(10):643-648 (1998).

Proetzel, G., et al., "Transforming growth factor-β3 is required for secondary palate fusion," Nat Genet., 11:409-414 (1995).

Sanderson, N., et al., "Hepatic expression of mature transforming growth factor β1 in transgenic mice results in multiple tissue lesions," Proc Natl Acad Sci., 92:2572-2576 (1995).

Sanford, L. P., et al., "TGFβ2 knockout mice have multiple developmental defects that are non-overlapping with other TGFβ knockout phenotypes," Development, 124:2659-2670 (1997).

Schultz-Cherry, S., et al., "Thrombospondin Binds and Activates the Small and Large Forms of Latent Transforming Growth Factor-β in a Chemically Defined System," J Biol Chem., 269(43):26775-26782 (1994).

Shi, Y. and Massagué, J., "Mechanisms of TGF-β Signaling from Cell Membrane to the Nucleus," Cell, 113:685-700 (2003).

Shi, M., et al., "Latent TGF-β structure and activation," Nature, 474:343-349 (2011).

Shull, M. M., et al., "Targeted disruption of the mouse transforming growth factor-β1 gene results in multifocal inflammatory disease," Nature, 359:693-699 (1992).

Xu, P., et al., "Post-translational regulation of TGF-β receptor and Smad signaling," FEBS Lett., 586:1871-1884 (2012).

Yu, L., et al., "TGF-β isoforms in renal fibrogenesis," Kidney Int'l, 64:844-856 (2003).

U.S. Appl. No. 16/971,924, 371(c) date Aug. 21, 2020, Kanamori, related application.

Derynck, R. and Miyazono, K., ed., "The TGF-β Family," 50:1-1114, Cold Spring Harbor Press (2008).

\* cited by examiner

CROSS-SPECIES ANTI-LATENT TGF-BETA 1 ANTIBODIES

The present invention relates to anti-latent TGF-beta 1 antibodies and methods of using the same.

BACKGROUND ART

Transforming growth factor-beta (transforming growth factor beta; TGF-beta) is a member of the TGF-beta superfamily of cytokines, which consists of TGF-beta isoforms, activins, inhibins, Nodal, bone morphogenetic proteins (BMPs), anti-Mullerian hormone (AMH), as well as growth and differentiation factors (GDFs). Members of this superfamily are dimeric proteins with conserved structures and have pleiotropic functions in vitro and in vivo (NPL 1, 2). The TGF-beta isoforms are involved in many cellular processes, including growth inhibition, cell migration, invasion, epithelial-mesenchymal transition (EMT), extracellular matrix (ECM) remodeling, and immune-suppression (NPL 3). However, although normally dynamically regulated and involved in maintenance of tissue homeostasis, TGF-beta isoforms are often chronically overexpressed in disease states, including cancer, fibrosis, and inflammation, and this excessive production of TGF-beta drives disease progression by modulating cell growth, migration, or phenotype.

Three separate TGF-beta isoforms (TGF-beta 1, TGF-beta 2, and TGF-beta 3) have been identified in mammals, and share 70-82% homology at the amino acid level (NPL 4). All three TGF-beta isoforms bind to TGF-beta receptor type 2 (TGFR2) as homodimers (their active form); TGFR2 then recruits and activates TGF-beta receptor type 1 (TGFR1) to activate receptor signaling (NPL 5). However, expression levels of the three isoforms vary depending on the tissue (NPL 6), and their functions are distinct, as demonstrated by the phenotypes of knockout mice (NPL 7-11).

Like other members of the TGF-beta superfamily, TGF-beta is synthesized as a precursor protein, which forms a homodimer that interacts with its latency-associated peptide (LAP) and a latent TGF-beta-binding protein (LTBP) to form a larger complex called the large latent complex (LLC). The TGF-beta gene encodes a preproprotein sequence consisting of a signal peptide, a propeptide that ends with a proprotein convertase (PPC) cleavage site, and the mature TGF-beta sequence. Furin hydrolyzes the PPC cleavage site, creating separate TGF-beta- and propeptide-derived homodimers. The two homodimers remain noncovalently associated and are secreted. This latent complex keeps TGF-beta in an inactive form that is incapable of binding to its receptors (NPL 12, 13). The TGF-beta activation process involves the release of the LLC from the ECM, followed by further proteolysis of LAP to release active TGF-beta to its receptors (NPL 3). Latent TGF-beta is cleaved to release active TGF-beta by a wide range of proteases, including plasmin (PLN), plasma kallikrein (PLK), matrix metalloproteinase (MMP) 2, and MMP9 (NPL 14), and by thrombospondin 1 (TSP-1) (NPL 15). Without wishing to be bound by any theory, MMP2, as well as MMP9, proteolytically cleaves latent TGF-beta 1 and release mature TGF-beta 1 from latent form. Both MMP2 and MMP9 are synthesized as inactive pro-MMP. Pro-MMP2 is activated by a complex of membrane type 1 MMP (MT1-MMP/MMP14) and tissue inhibitor of metalloproteinase 2 (TIMP-2). Pro-MMP9 is activated through an interacting protease cascade involving plasmin and stromelysin 1 (MMP-3). Plasmin generates active MMP-3 from its zymogen. Active MMP-3 cleaves the propeptide from the 92-kDa pro-MMP-9, yielding an 82-kDa enzymatically active enzyme. The cleavage sites of MMPs are not specifically determined; however, it is reported that MMP3 specifically cleaves the site between 79 Ala and 80 Leu of latent TGF-beta, so as to activate TGF-beta (WO2005/023870). Alternatively, upon mechanical stretch, integrins can activate TGF-beta by binding to the RGD motif present in LAP to induce the release of mature TGF-beta from its latent complex (NPL 16, 17).

After activation, the dimeric TGF-beta ligand binds to the extracellular domains of type I and type II receptors and induces close proximity, placing the intracellular serine/threonine kinase domains of the receptors in a conformation that facilitates the phosphorylation and subsequent activation of the type I receptor. This activation of the type I receptor leads to the propagation of signaling by at least two seemingly independent routes: the SMAD-dependent canonical pathway and the SMAD-independent or non-canonical pathway. In the SMAD-dependent pathway, activation of TGFR1 (also known as ALK5) leads to phosphorylation of SMAD proteins. SMAD2 and SMAD3 are substrates of TGFR1. Upon phosphorylation by the receptor, SMADs together with the common mediator SMAD4 translocate to the nucleus, where they interact with other transcription factors to regulate transcriptional responses (NPL 18). In the non-canonical pathway, the activated TGF-beta receptor complex transmits a signal through other factors, such as tumor necrosis factor (TNF) receptor-associated factor 4 (TRAF4), TRAF6, TGF-beta-activated kinase 1 (TAK1, also known as MAP3K7), p38 mitogen-activated protein kinase (p38 MAPK), RHO, phosphoinositide 3-kinase (PI3K), AKT (also known as protein kinase B), extracellular signal-regulated kinase (ERK), JUN N-terminal kinase (JNK), or nuclear factor-kappa B (NF-kappa B). Thus, cellular responses to TGF-beta signaling result from the dynamic combination of canonical and non-canonical signaling cascades.

Fibrosis, or the accumulation of ECM molecules that make up scar tissue, is a common feature of chronic tissue injury. Pulmonary fibrosis, renal fibrosis, and hepatic cirrhosis are among the more common fibrotic diseases, which in aggregate represent a huge unmet clinical need. TGF-beta strongly promotes generation of the extracellular matrices of mesenchymal cells, while at the same time it suppresses the growth of epithelial cells, which contributes to the pathogenesis of sclerotic diseases. Overexpression of the active form of TGF-beta 1 in the liver of transgenic mice is sufficient to induce fibrotic disease in multiple organs (NPL 19). On the other hand, TGF-beta also plays an important role in maintaining our health. For example, TGF-beta suppresses excessive generation of proteases in the lung and prevents the destruction of lung tissue that leads to emphysema. Also, mice with deleted TGF-beta 1 show prenatal lethality (around 50% at 10.5 days post coitus) or their offspring die shortly after birth, with massive inflammatory lesions seen in many organs, including the lungs (vasculitis, perivascular cuffing, and interstitial pneumonia) and heart (endocarditis and myocarditis), which suggests that TGF-beta 1 plays a crucial role in maintaining immune homeostasis (NPL 7).

Results of studies using a neutralizing antibody to TGF-beta and animal models revealed that sclerotic diseases can be prevented or cured by suppressing the action of TGF-beta. As TGF-beta is produced as a precursor protein, there are several reported approaches to prevent activation from the latent form. Another method of preventing activation from the latent form is to use an inhibitor or antibody that binds to latent TGF-beta to block cleavage by proteases, such as PLK and PLN. Several antibodies that use this method of suppressing TGF-beta activation were reported as preventing or treating hepatic fibrosis/cirrhosis (PTL 1). In addition, there have been some documents mentioning anti-LAP antibodies for treating cancer (PTL 2), and TGF beta 1-binding immunoglobulins for treating TGF beta 1-related disorders (PTL 3).

CITATION LIST

Patent Literature

[PTL 1] WO 2011102483
[PTL 2] WO 2016115345
[PTL 3] WO 2017156500

Non Patent Literature

[NPL 1] McCartney-Francis, N. L. et al. Int. Rev. Immunol. 16, 553-580 (1998)
[NPL 2] Massague, J. Annu. Rev. Biochem. 67, 753-791 (1998)
[NPL 3] Derynck, R. & Miyazono, K. Cold Spring Harbor Press (2008)
[NPL 4] Yu, L. et al. Kidney Int. 64, 844-856 (2003).
[NPL 5] Xu, P., Liu, J. & Derynck, R. et al. FEBS Lett. 586, 1871-1884 (2012).
[NPL 6] Millan, F. A. et al. Development 111, 131-143 (1991).
[NPL 7] Kulkarni, A. B. et al. Proc. Natl Acad. Sci. USA 90, 770-774 (1993).
[NPL 8] Shull, M. M. et al. Nature 359, 693-699 (1992).
[NPL 9] Dickson, M. C. et al. Development 121, 1845-1854 (1995).
[NPL 10] Sanford, L. P. et al. Development 124, 2659-2670 (1997).
[NPL 11] Proetzel, G. et al. Nature Genet. 11, 409-414 (1995).
[NPL 12] Dubois, C. M. et al. J. Biol. Chem. 270, 10618-10624 (1995)
[NPL 13] Nunes, I. et al. J. Am. Optom. Assoc. 69, 643-648 (1998)
[NPL 14] Annes, J. et al. J. Cell Sci. 116, 217-224 (2003).
[NPL 15] Schultz-Cherry, S. et al. J. Biol. Chem. 269, 26775-26782 (1994).
[NPL 16] Munger, J. S. et al. Cell 96, 319-328 (1999).
[NPL 17] Shi, M. et al. Nature 474, 343-349 (2011).
[NPL 18] Shi, Y. & Massague, et al. Cell 113, 685-700 (2003).
[NPL 19] Sanderson, N. et al. Proc. Natl Acad. Sci. USA 92, 2572-2576 (1995).

SUMMARY OF INVENTION

Technical Problem

An object of the invention is to provide cross-species, humanized and optimized anti-latent TGF-beta 1 antibodies which inhibit a protease mediated activation of latent TGF-beta 1 without inhibiting integrin mediated activation of latent TGF-beta 1. The invention also provides combination therapies comprising an anti-latent TGF-beta 1 antibody and one or more immune checkpoint inhibitors.

Solution to Problem

The present inventors have conducted diligent studies under the situations as described above and consequently created cross-species, humanized and optimized anti-latent TGF-beta 1 antibodies which inhibit a protease mediated activation of TGF-beta 1 without inhibiting integrin mediated activation of latent TGF-beta 1. Further, the anti-latent TGF-beta 1 antibodies showed antitumor effect when administered in combination with one or more immune checkpoint inhibitors.

The present invention provides:

A1. An anti-latent TGF-beta 1 antibody comprising:
 (a) HVR-H1, HVR-H2 and HVR-H3 comprising the amino acid sequences of SEQ ID NO:20, 21 and 22, respectively;
 (b) HVR-H1, HVR-H2 and HVR-H3 comprising the amino acid sequences of SEQ ID NO:26, 27 and 28, respectively;
 (c) HVR-H1, HVR-H2 and HVR-H3 comprising the amino acid sequences of SEQ ID NO:32, 33 and 34, respectively; or
 (d) HVR-H1, HVR-H2 and HVR-H3 comprising the amino acid sequences of SEQ ID NO:38, 39 and 40, respectively.

A2. The anti-latent TGF-beta 1 antibody of A1 which further comprises:
 (a) HVR-L1, HVR-L2 and HVR-L3 comprising the amino acid sequences of SEQ ID NO:23, 24 and 25, respectively;
 (b) HVR-L1, HVR-L2 and HVR-L3 comprising the amino acid sequences of SEQ ID NO:29, 30 and 31, respectively;
 (c) HVR-L1, HVR-L2 and HVR-L3 comprising the amino acid sequences of SEQ ID NO:35, 36 and 37, respectively; and
 (d) HVR-L1, HVR-L2 and HVR-L3 comprising the amino acid sequences of SEQ ID NO:41, 42 and 43, respectively.

A3. An anti-latent TGF-beta 1 antibody comprising:
 (a) HVR-H1, HVR-H2 and HVR-H3 comprising the amino acid sequences of SEQ ID NO:20, 21 and 22, respectively, and HVR-L1, HVR-L2 and HVR-L3 comprising the amino acid sequences of SEQ ID NO:23, 24 and 25, respectively;
 (b) HVR-H1, HVR-H2 and HVR-H3 comprising the amino acid sequences of SEQ ID NO:26, 27 and 28, respectively, and HVR-L1, HVR-L2 and HVR-L3 comprising the amino acid sequences of SEQ ID NO:29, 30 and 31, respectively;
 (c) HVR-H1, HVR-H2 and HVR-H3 comprising the amino acid sequences of SEQ ID NO:32, 33 and 34, respectively, and HVR-L1, HVR-L2 and HVR-L3 comprising the amino acid sequences of SEQ ID NO:35, 36 and 37, respectively; or
 (d) HVR-H1, HVR-H2 and HVR-H3 comprising the amino acid sequences of SEQ ID NO:38, 39 and 40, respectively, and HVR-L1, HVR-L2 and HVR-L3 comprising the amino acid sequences of SEQ ID NO:41, 42 and 43, respectively.

A4. The anti-latent TGF-beta 1 antibody of any one of A1 to A3, comprising:
 (a)(i) a VH sequence having at least 95% sequence identity to the amino acid sequence of SEQ ID NO:12, (ii) a VL sequence having at least 95% sequence identity to the amino acid sequence of SEQ ID NO:13, or (iii) a VH sequence as in (i) and a VL sequence as in (ii);
 (b)(i) a VH sequence having at least 95% sequence identity to the amino acid sequence of SEQ ID NO:14, (ii) a VL sequence having at least 95% sequence identity to the amino acid sequence of SEQ ID NO:15, or (iii) a VH sequence as in (i) and a VL sequence as in (ii);

(c)(i) a VH sequence having at least 95% sequence identity to the amino acid sequence of SEQ ID NO:16, (ii) a VL sequence having at least 95% sequence identity to the amino acid sequence of SEQ ID NO:17, or (iii) a VH sequence as in (i) and a VL sequence as in (ii); or (d)(i) a VH sequence having at least 95% sequence identity to the amino acid sequence of SEQ ID NO:18, (ii) a VL sequence having at least 95% sequence identity to the amino acid sequence of SEQ ID NO:19, or (iii) a VH sequence as in (i) and a VL sequence as in (ii).

A5. The anti-latent TGF-beta 1 antibody of A4, comprising a VH sequence of SEQ ID NO: 12, 14, 16 or 18.

A6. The anti-latent TGF-beta 1 antibody of A4 or A5, comprising a VL sequence of SEQ ID NO: 13, 15, 17 or 19.

A7. The anti-latent TGF-beta 1 antibody of any one of A4 to A6, comprising:
(a) a VH sequence of SEQ ID NO:12 and a VL sequence of SEQ ID NO:13;
(b) a VH sequence of SEQ ID NO:14 and a VL sequence of SEQ ID NO:15;
(c) a VH sequence of SEQ ID NO:16 and a VL sequence of SEQ ID NO:17; or
(d) a VH sequence of SEQ ID NO:18 and a VL sequence of SEQ ID NO:19.

A8. An anti-latent TGF-beta 1 antibody comprising:
(a) a VH sequence of SEQ ID NO:12 and a VL sequence of SEQ ID NO:13;
(b) a VH sequence of SEQ ID NO:14 and a VL sequence of SEQ ID NO:15;
(c) a VH sequence of SEQ ID NO:16 and a VL sequence of SEQ ID NO:17; or
(d) a VH sequence of SEQ ID NO:18 and a VL sequence of SEQ ID NO:19.

A9. The anti-latent TGF-beta 1 antibody of any one of A1 to A8, which is a human, humanized, or chimeric antibody.

A10. The anti-latent TGF-beta 1 antibody of any one of A1 to A9, which is a full length IgG antibody, preferably a full length IgG1 antibody.

A11. The anti-latent TGF-beta 1 antibody of any one of A1 to A9, which is a bispecific antibody.

A12. The anti-latent TGF-beta 1 antibody of any one of A1 to A11, wherein the anti-latent TGF-beta 1 antibody comprises a modified IgG1 Fc region having reduced effector function compared with a wild type IgG1 Fc region.

A13. The anti-latent TGF-beta 1 antibody of A12, wherein the modified IgG1 Fc region comprises amino acid substitutions at positions at EU235 and/or EU236, according to the EU index.

A14. The anti-latent TGF-beta 1 antibody of A12 or A13, wherein the modified IgG1 Fc region comprises amino acid substitutions of L235R and G236R, according to the EU index.

A15. The anti-latent TGF-beta 1 antibody of any one of A12 to A14, wherein the modified IgG1 Fc region further has enhanced binding activity to FcRn compared with a wild type IgG1 Fc region.

A16. The anti-latent TGF-beta 1 antibody of A15, wherein the modified IgG1 Fc region comprises one or more amino acid substitutions at positions selected from the group consisting of: EU428, EU434, EU438 and EU440, according to the EU index.

A17. The anti-latent TGF-beta 1 antibody of any one of A15 or A16, wherein the modified IgG1 Fc region comprises amino acid substitutions of M428L, N434A, Q438R and S440E.

A18. The anti-latent TGF-beta 1 antibody of any one of A1 to A11, wherein the anti-latent TGF-beta 1 antibody comprises a modified IgG1 Fc region, wherein the modified IgG1 Fc region comprises amino acid substitutions of K214R, L235R and G236R.

A19. The anti-latent TGF-beta 1 antibody of any one of A1 to A11, wherein the anti-latent TGF-beta 1 antibody comprises a modified IgG1 Fc region, wherein the modified IgG1 Fc region comprises amino acid substitutions of K214R, L235R, G236R, M428L, N434A, Q438R and S440E.

A20. The anti-latent TGF-beta 1 antibody of any one of A1 to A11, which is an antibody fragment.

A21. An anti-latent TGF-beta 1 antibody comprising:
(a) a full length heavy chain sequence of SEQ ID NO:47 and a full length light chain sequence of SEQ ID NO:60;
(b) a full length heavy chain sequence of SEQ ID NO:48 and a full length light chain sequence of SEQ ID NO:61;
(c) a full length heavy chain sequence of SEQ ID NO:49 and a full length light chain sequence of SEQ ID NO:62;
(d) a full length heavy chain sequence of SEQ ID NO:50 and a full length light chain sequence of SEQ ID NO:63;
(e) a full length heavy chain sequence of SEQ ID NO:51 and a full length light chain sequence of SEQ ID NO:64;
(f) a full length heavy chain sequence of SEQ ID NO:52 and a full length light chain sequence of SEQ ID NO:65;
(g) a full length heavy chain sequence of SEQ ID NO:53 and a full length light chain sequence of SEQ ID NO:66; or
(h) a full length heavy chain sequence of SEQ ID NO:54 and a full length light chain sequence of SEQ ID NO:67.

A22. The anti-latent TGF-beta 1 antibody of any one of A1 to A21, wherein the latent TGF beta-1 is a human latent TGF beta-1, a mouse latent TGF beta-1, or a cynomolgus monkey latent TGF beta-1.

A23. The anti-latent TGF-beta 1 antibody of any one of A1 to A22, wherein the anti-latent TGF-beta 1 antibody binds to a human latent TGF-beta 1, a mouse latent TGF-beta 1, and a cynomolgus monkey latent TGF-beta 1.

A24. The anti-latent TGF-beta 1 antibody of any one of A1 to A23, wherein the anti-latent TGF-beta 1 antibody binds to a latency-associated peptide (LAP) region of a latent TGF-beta 1.

A25. An immunoconjugate comprising the anti-latent TGF beta-1 antibody of any one of A1 to A24 and a cytotoxic agent.

A26. An isolated nucleic acid encoding the anti-latent TGF beta-1 antibody of any one of A1 to A24.

A27. A vector comprising the nucleic acid of A26.

A28. A host cell comprising the nucleic acid of A26 or the vector of A27.

A29. A method of producing an anti-latent TGF beta-1 antibody comprising culturing the host cell of A28 so that the antibody is produced.

A30. The method of A29, further comprising recovering the antibody from the host cell.

B1. The anti-latent TGF beta-1 antibody of any one of A1 to A24 or the immunoconjugate of A25, for use as a medicament.

B2. The anti-latent TGF beta-1 antibody of any one of A1 to A24 or the immunoconjugate of A25, for use in treating fibrosis or cancer.

B3. Use of the anti-latent TGF beta-1 antibody of any one of A1 to A24 or the immunoconjugate of A25, in the manufacture of a medicament for treatment of fibrosis or cancer.

B4. The anti-latent TGF beta-1 antibody of any one of A1 to A24 or the immunoconjugate of A25, for use in combination with an additional therapeutic agent, preferably an immune checkpoint inhibitor, for treatment of cancer.

B5. The anti-latent TGF beta-1 antibody or the immunoconjugate of B4, wherein the immune checkpoint inhibitor is a PD-1 axis binding antagonist, preferably an anti-PD-1 antibody or an anti-PD-L1 antibody.

B6. The anti-latent TGF beta-1 antibody or the immunoconjugate of B4, wherein the immune checkpoint inhibitor is an anti-PD-L1 antibody.

B7. The anti-latent TGF beta-1 antibody or the immunoconjugate of any one of B4 to B6, wherein the immune checkpoint inhibitor is administered concomitantly with the anti-latent TGF beta-1 antibody or the immunoconjugate.

B8. The anti-latent TGF beta-1 antibody or the immunoconjugate of any one of B4 to B6, wherein the immune checkpoint inhibitor is administered before or after the administration of the anti-latent TGF beta-1 antibody or the immunoconjugate.

C1. A pharmaceutical formulation comprising the anti-latent TGF beta-1 antibody of any one of A1 to A24 or the immunoconjugate of A25, and a pharmaceutically acceptable carrier.

C2. The pharmaceutical formulation of C1, further comprising an additional therapeutic agent, preferably an immune checkpoint inhibitor.

C3. The pharmaceutical formulation of C2, wherein the immune checkpoint inhibitor is a PD-1 axis binding antagonist, preferably an anti-PD-1 antibody or an anti-PD-L1 antibody.

C4. The pharmaceutical formulation of C2, wherein the immune checkpoint inhibitor is an anti-PD-L1 antibody.

C5. The pharmaceutical formulation of any one of C1 to C4, for use in treatment of fibrosis or cancer.

C6. The pharmaceutical formulation of any one of C1 to C4, for use in combination with an additional therapeutic agent, preferably an immune checkpoint inhibitor, for treatment of cancer.

C7. The pharmaceutical formulation of C6, wherein the immune checkpoint inhibitor is a PD-1 axis binding antagonist, preferably an anti-PD1 antibody or an anti-PD-L1 antibody.

C8. The pharmaceutical formulation of C6, wherein the immune checkpoint inhibitor is an anti-PD-L1 antibody.

C9. The pharmaceutical formulation of any one of C6 to C8, wherein the immune checkpoint inhibitor is administered concomitantly with the pharmaceutical formulation.

C10. The pharmaceutical formulation of any one of C6 to C8, wherein the immune checkpoint inhibitor is administered before or after the administration of the pharmaceutical formulation.

D1. A pharmaceutical formulation comprising an immune checkpoint inhibitor and a pharmaceutically acceptable carrier, for use in combination with the anti-latent TGF beta-1 antibody of any one of Claim A1 to A24 or the immunoconjugate of Claim A25, for treatment of cancer.

D2. The pharmaceutical formulation of D1, wherein the immune checkpoint inhibitor is a PD-1 axis binding antagonist, preferably an anti-PD1 antibody or an anti-PD-L1 antibody.

D3. The pharmaceutical formulation of D1, wherein the immune checkpoint inhibitor is an anti-PD-L1 antibody.

D4. The pharmaceutical formulation of any one of D1 to D3, wherein the anti-latent TGF beta-1 antibody or the immunoconjugate is administered concomitantly with the pharmaceutical formulation.

D5. The pharmaceutical formulation of any one of D1 to D3, wherein the anti-latent TGF beta-1 antibody or the immunoconjugate is administered before or after the administration of the pharmaceutical formulation.

E1. A method of treating an individual having fibrosis or cancer comprising administering to the individual an effective amount of the anti-latent TGF beta-1 antibody of any one of A1 to A24 or the immunoconjugate of A25.

E2. The method of E1 further comprising administering an additional therapeutic agent, preferably an immune checkpoint inhibitor, to the individual.

E3. The method of E1 or E2, wherein the immune checkpoint inhibitor is a PD-1 axis binding antagonist, preferably an anti-PD-1 antibody or an anti-PD-L1 antibody.

E4. The method of E3, wherein the immune checkpoint inhibitor is an anti-PD-L1 antibody.

E5. The method of any one of E1 to E4, wherein the immune checkpoint inhibitor is administered concomitantly with the anti-latent TGF beta-1 antibody or the immunoconjugate.

E6. The method of any one of E1 to E4, wherein the immune checkpoint inhibitor is administered before or after the administration of the anti-latent TGF beta-1 antibody or the immunoconjugate.

DESCRIPTION OF EMBODIMENTS

I. Definitions

Figure 1A:
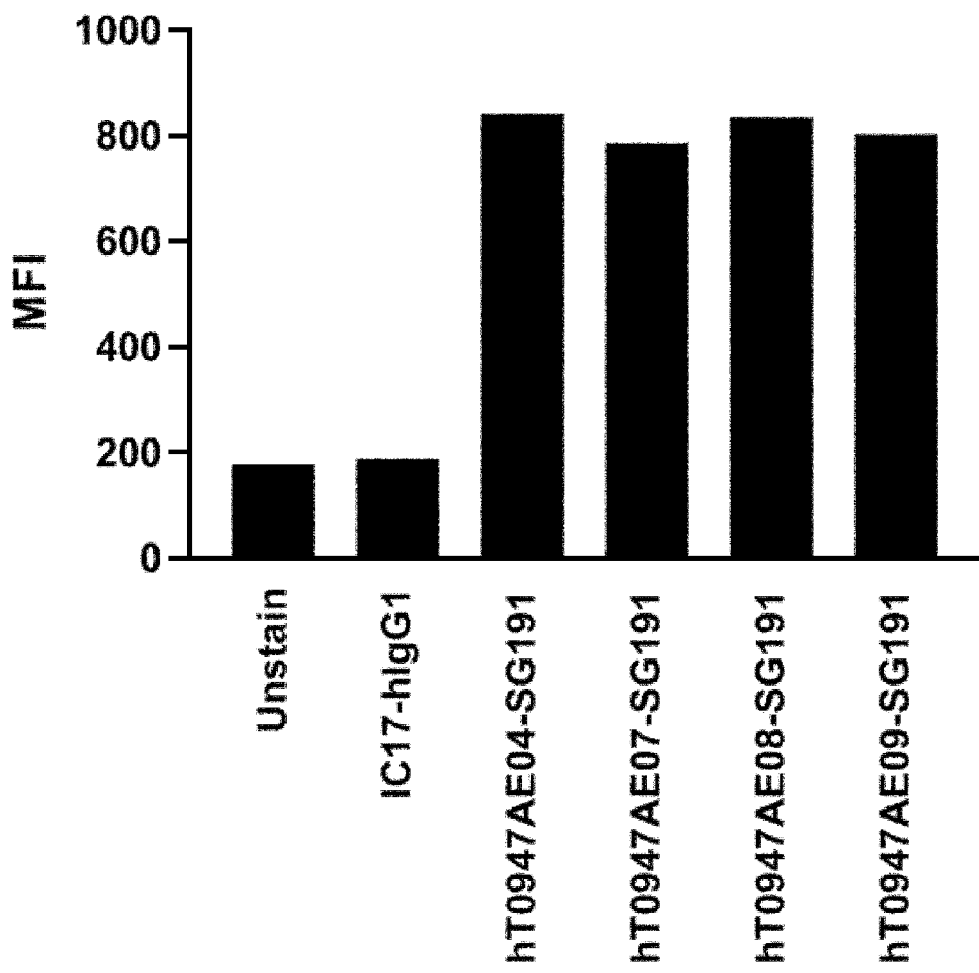
FIG. 1A shows the results of antibody binding to cell surface latent TGF-beta 1 on BaF3 cells. IC17-hIgG1 represents an anti-KLH antibody as a negative control. hT0947AE04-SG191, hT0947AE07-SG191, hT0947AE08-SG191, and hT0947AE09-SG191 represent anti-latent TGF-beta 1 antibodies.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

The term "binding activity" refers to the strength of the sum total of noncovalent interactions between one or more binding sites of a molecule (e.g., an antibody) and its binding partner (e.g., an antigen). Herein, "binding activity" is not strictly limited to a 1:1 interaction between members of a binding pair (e.g., antibody and antigen). For example, when the members of a binding pair reflect a monovalent 1:1 interaction, the binding activity is particularly called the intrinsic binding affinity (affinity). When a member of a binding pair is capable of both monovalent binding and multivalent binding, the binding activity is the sum of each binding strength. The binding activity of a molecule X for its partner Y can generally be represented by the dissociation constant (KD) or "binding amount of analyte per unit amount of ligand" (hereinbelow, may be referred to as "binding amount"). Those skilled in the art would understand that, generally, lower value of dissociation constant (KD) means higher binding activity, and higher value of "binding amount of analyte per unit amount of ligand" or "binding amount" means higher binding activity. Binding activity can be measured by common methods known in the art, including those described herein. Specific illustrative and exemplary embodiments for measuring binding activity are described in the following.

A "binding activity-matured", "affinity-matured" antigen-binding molecule or antibody, "binding activity-increased (enhanced)", or "affinity-increased (enhanced)" antigen-binding molecule or antibody refers to an antibody with one or more alterations (e.g., substitutions) in one or more hypervariable regions (HVRs), compared to a parent antigen-binding molecule or a parent antibody which does not carry such alterations, such alterations resulting in an improvement in the binding activity of the antigen-binding molecule or antibody for antigen.

The terms "anti-latent TGF-beta 1 antibody" and "an antibody that can bind to latent TGF-beta 1" refer to an antibody that is capable of binding latent TGF-beta 1 with sufficient binding activity such that the antibody is useful as a diagnostic and/or therapeutic agent in targeting latent TGF-beta 1. In one embodiment, "an antibody that can bind to latent TGF-beta 1" is an antibody that specifically binds to latent TGF-beta 1. In one embodiment, the extent of binding activity of an anti-latent TGF-beta 1 antibody to an unrelated, non-latent TGF-beta 1 protein is less than about 10% of the binding activity of the antibody to latent TGF-beta 1 as measured, e.g., by a radioimmunoassay (RIA). In certain embodiments, an antibody that can bind to TGF-beta 1 has a dissociation constant (KD) of 1 micromolar or less, 100 nM or less, 10 nM or less, 1 nM or less, 0.1 nM or less, 0.01 nM or less, or 0.001 nM or less (e.g. 10-8 M or less, e.g. from 10-8 M to 10-13 M, e.g., from 10-9 M to 10-13 M). In certain embodiments, an anti-latent TGF-beta 1 antibody binds to an epitope of latent TGF-beta 1 that is conserved among latent TGF-beta 1 from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. The term "antibody" also includes any antigen binding molecule which comprises variable heavy chain and/or variable light chain structure(s) of immunoglobulin.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer. In one example, cancer is resistant to immune-checkpoint inhibitors and/or shows limited response to immune-checkpoint inhibitors.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called alpha, delta, epsilon, gamma, and mu, respectively.

The term "cytotoxic agent" as used herein refers to a substance that inhibits or prevents a cellular function and/or causes cell death or destruction. Cytotoxic agents include, but are not limited to, radioactive isotopes (e.g., 211At, 131I, 125I, 90Y, 186Re, 188Re, 153Sm, 212Bi, 32P, 212Pb and radioactive isotopes of Lu); chemotherapeutic agents or drugs (e.g., methotrexate, adriamycin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) or glycine-lysine (residues 446-447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-latent TGF-beta 1 antibody" or "nucleic acid encoding an anti-latent TGF-beta 1 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies composing the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (kappa) and lambda (lambda), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, Megalign (DNASTAR) software, or GENETYX (registered trademark) (Genetyx Co., Ltd.). Those skilled in the art can determine appropriate parameters for aligning sequences, including any algorithms needed to achieve maximal alignment over the full length of the sequences being compared.

The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "TGF-beta 1," as used herein, refers to any native TGF-beta 1 from any vertebrate source, including mammals such as primates (e.g. humans) and rodents (e.g., mice and rats), unless otherwise indicated. The term encompasses "full-length" unprocessed TGF-beta 1 as well as any form of TGF-beta 1 that results from processing in the cell. The term also encompasses naturally occurring variants of TGF-beta 1, e.g., splice variants or allelic variants. The amino acid sequence of an exemplary human TGF-beta 1 preproprotein is shown in SEQ ID NO: 68 (NCBI RefSeq: NP_000651.3) and the nucleic acid sequence encoding an exemplary human TGF-beta 1 is shown in SEQ ID NO: 69 (NCBI RefSeq: NM_000660.6). The amino acid sequence of an exemplary mouse TGF-beta 1 preproprotein is shown in SEQ ID NO: 70 (NCBI RefSeq: NP_035707.1) and the nucleic acid sequence encoding an exemplary mouse TGF-beta 1 is shown in SEQ ID NO: 71 (NCBI RefSeq: NM_011577.2). The amino acid sequence of an exemplary cynomolgus monkey TGF-beta 1 preproprotein is shown in SEQ ID NO: 72 (NCBI RefSeq: XP_005589396.1) and the nucleic acid sequence encoding an exemplary cynomolgus monkey TGF-beta 1 is shown in SEQ ID NO: 73 (NCBI RefSeq: XM_005589339.2). The term "TGF-beta 1" encompasses both latent TGF-beta 1 and mature TGF-beta 1.

The term "latent TGF-beta 1", as used herein, refers to any TGF-beta 1 which forms a latent TGF-beta 1 complex ("cell surface latent TGF-beta 1", LLC or SLC (see below)) and/or which is incapable of binding to its receptors. Transforming growth factor-beta 1 (TGF-beta 1) is a member of TGF-beta, which is a member of TGF-beta superfamily Like other members of TGF-beta superfamily, TGF-beta is synthesized as a precursor protein, which forms a homodimer that interacts with its latency-associated peptide (LAP) and a latent TGF-beta-binding protein (LTBP), forming a larger complex called the large latent complex (LLC). The amino acid sequence of an exemplary latent human TGF-beta 1 (TGF-beta homodimer and its LAP) is amino acids 30-390 of SEQ ID NO: 68. The amino acid sequence of and exemplary mouse latent TGF-beta 1 (TGF-beta homodimer and its LAP) is amino acids 30-390 of SEQ ID NO: 70. The amino acid sequence of an exemplary latent cynomolgus monkey TGF-beta 1 (TGF-beta homodimer and its LAP) is amino acids 30-390 of SEQ ID NO: 72.

A complex formed from the TGF-beta homodimer and its LAP is called Small Latent Complex (SLC). This latent complex keeps TGF-beta in an inactive form, which is incapable of binding to its receptors. SLC may be covalently linked to an additional protein, latent TGF-beta binding protein (LTBP), forming the large latent complex (LLC). There are four different LTBP isoforms known, LTBP-1, LTBP-2, LTBP-3 and LTBP-4. It has been reported that LTBP-1, LTBP-3 and LTBP-4 bind to SLC (See, e.g., Rifkin et al., J Biol Chem. 2005 Mar. 4; 280(9):7409-12). SLC may also be covalently linked to other additional proteins, such as glycoprotein A repetitions predominant (GARP) or leucine-rich repeat-containing protein 33 (LRRC33). GARP and LRRC have a transmembrane domain and associate with LAP on the cell surface (See, e.g., Wang et al., Mol Biol Cell. 2012 March; 23(6):1129-39). As to LLCs, it is reported that LLCs associate covalently with the extracellular matrix (ECM) via the N-termini of the LTBPs (See, e.g., Saharinen et al., Cytokine Growth Factor Rev. 1999 June; 10(2):99-117). In some embodiments, latent TGF-beta 1 associated with the ECM on a cell surface is referred to as "cell surface latent TGF-beta 1".

The term "active TGF-beta 1", "mature TGF-beta 1", or "active mature TGF-beta 1", as used herein, refers to any TGF-beta 1 homodimer which does not form a latent TGF-beta 1 complex (LLC or SLC) and which is capable of binding to its receptors. The TGF-beta 1 activation process involves the release of the LLC from the ECM, followed by further proteolysis of LAP to release active TGF-beta to its receptors. Wide range of proteases including plasmin (PLN), prekallikrein (PLK), matrix metalloproteinase (MMP) 2, MMP9, MMP13, MMP14, Thrombin, Tryptase and Calpain are known to cleave latent TGF-beta and release active TGF-beta. These proteases may be collectively called "(latent) TGF-beta-cleaving proteases" or "(latent) TGF-beta 1-cleaving proteases" in the context of the present invention. In addition to proteases, thrombospondin 1 (TSP-1), Neuropilin-1 (Nrp1), ADAMSTS1 and F-spondin activate latent TGF-beta. Alternatively, upon mechanical stretch, integrins (preferably integrin alpha V beta 8 and/or integrin alpha V beta 6) can activate TGF-beta by binding to the RGD motif present in LAP and inducing the release of mature TGF-beta from its latent complex form.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Compositions and Methods

In one aspect, the invention is based, in part, on anti-latent TGF-beta 1 antibodies and uses thereof. In certain embodiments, antibodies that bind to TGF-beta 1 are provided. Antibodies of the invention are useful, e.g., for the diagnosis or treatment of fibrosis, preferably myocardial fibrosis, pulmonary fibrosis, liver fibrosis, renal fibrosis, skin fibrosis, ocular fibrosis and myelofibrosis. Antibodies of the invention are also useful, e.g., for the diagnosis or treatment of cancer. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

A. Exemplary Anti-Latent TGF-Beta 1 Antibodies

In one aspect, the invention provides isolated antibodies that bind to latent TGF-beta 1. In further embodiments, the anti-latent TGF-beta 1 antibody binds to latent associated protein (LAP) region of the latent TGF-beta 1. An example of LAP region comprises amino acids 30-278 of a human TGF-beta 1 preproprotein (SEQ ID NO: 1). LAP is a component of latent TGF-beta 1, as described above. In some embodiments, an anti-latent TGF-beta 1 antibody binds to latent TGF-beta 1 with a dissociation constant (KD) of 10-8 nM or less, 10-9 nM or less, or 10-10 nM or less.

In one aspect, an anti-latent TGF-beta 1 antibody binds to a latent TGF-beta 1 forming LLC, and/or a latent TGF-beta 1 forming complex with GARP or LRRC33. In certain embodiments, an anti-latent TGF-beta 1 antibody binds to cell surface latent TGF-beta 1, which is a latent TGF-beta 1 associated with the extracellular matrix (ECM) on a cell surface. In another aspect, an anti-latent TGF-beta 1 antibody binds to a latent TGF-beta 1, wherein the LAP region of the latent TGF-beta 1 is not linked to LTBP, forming the small latent complex (SLC). In certain embodiments, SLCs exist in a soluble form. In some embodiments, an anti-latent TGF-beta 1 antibody binds to latent TGF-beta 1 (cell surface latent TGF-beta 1, LLC, or SLC) with a dissociation constant (KD) of 10-8 nM or less, 10-9 nM or less, or 10-10 nM or less.

In one aspect, an anti-latent TGF-beta 1 antibody inhibits activation of a latent TGF-beta 1. The term "activation" of latent TGF-beta 1, as used herein, refers to any process in which mature TGF-beta 1 is released from LAP, which is a component of the latent TGF-beta 1. The activation of latent TGF-beta 1 can be detected, for example, by measuring mature TGF-beta 1 and/or measuring mature TGF-beta 1 activity using various techniques known in the art or described herein. In some embodiments, an anti-latent TGF-beta 1 antibody inhibits the release of mature TGF-beta 1 from latent TGF-beta 1. As described above, it has been reported that mature TGF-beta 1 is released from latent TGF-beta 1 by activators such as proteases, integrins and other non-protease activators. Non-limited examples of proteases which activate latent TGF-beta 1 include plasmin (PLN), prekallikrein (PLK), matrix metalloproteinase (MMP) 2 and MMP9. In some embodiments, an anti-latent TGF-beta 1 antibody inhibits protease mediated and/or integrin mediated release of mature TGF-beta 1 from latent TGF-beta 1. As described above, proteases cleave LAP region of latent TGF-beta 1, which causes release of mature TGF-beta 1. In some embodiments, the cleavage sites by PLN and/or PLK locate within a fragment consisting of amino acids 56-59 of LAP polypeptide.

In one aspect, an anti-latent TGF-beta 1 antibody inhibits protease mediated release of mature TGF-beta 1 from latent TGF-beta 1 without inhibiting protease mediated cleavage of LAP portion of latent TGF-beta 1. In some embodiments, an anti-latent TGF-beta 1 antibody inhibits protease mediated release of mature TGF-beta 1 from latent TGF-beta 1 and allows a protease to cleave the LAP region while the anti-latent TGF-beta 1 antibody binds to the LAP region of the latent TGF-beta 1. In some embodiments, an anti-latent TGF-beta 1 antibody does not block access of a protease to latent TGF-beta 1, especially to the cleavage sites by PLN and/or PLK. In other embodiments, an anti-latent TGF-beta 1 antibody does not bind to protease cleavage sites of LAP portion of a latent TGF-beta 1, especially the cleavage sites by PLN and/or PLK.

In some embodiments, an anti-latent TGF-beta 1 antibody that inhibits protease mediated release of mature TGF-beta 1 from latent TGF-beta 1 is an antibody which (i) inhibits cleavage of LAP region mediated by one or more proteases, but (ii) does not inhibit cleavage of LAP region mediated by other proteases. For example, an anti-latent TGF-beta 1 antibody (1-i) inhibits MMP2 and/or MMP9 mediated release of mature TGF-beta 1 by inhibiting MMP2 and/or MMP9 mediated cleavage of LAP portion of latent TGF-beta 1, and (1-ii) inhibits PLN and/or PLK mediated release of mature TGF-beta 1 without inhibiting PLN and/or PLK mediated cleavage of LAP portion of latent TGF-beta 1. Alternatively, an anti-latent TGF-beta 1 antibody (2-i) inhibits PLN and/or PLK mediated release of mature TGF-beta 1 by inhibiting PLN and/or PLK mediated cleavage of LAP portion of latent TGF-beta 1, and (2-ii) inhibits MMP2 and/or MMP9 mediated release of mature TGF-beta 1 without inhibiting MMP2 and/or MMP9 mediated cleavage of LAP portion of latent TGF-beta 1. Alternatively, an anti-latent TGF-beta 1 antibody (3-i) inhibits PLN and/or PLK mediated release of mature TGF-beta 1 without inhibiting PLN and/or PLK mediated cleavage of LAP portion of latent TGF-beta 1, and (3-ii) inhibits MMP2 and/or MMP9 mediated release of mature TGF-beta 1 without inhibiting MMP2 and/or MMP9 mediated cleavage of LAP portion of latent TGF-beta 1.

In some embodiments, antibodies "which inhibit activation of a latent TGF-beta 1" include antibodies that cause at least 5%, 10%, 15%, 20%, 25%, 30%, 35%, or 40% or greater decrease in TGF-beta 1 activation. In other embodiments, antibodies "which inhibit protease mediated release of mature TGF-beta 1 from latent TGF-beta 1" include antibodies that cause at least 5%, 10%, 15%, 20%, 25%, 30%, 35%, or 40% or greater decrease in protease mediated release of mature TGF-beta 1 from latent TGF-beta 1. In further embodiments, antibodies which inhibit protease mediated release of mature TGF-beta 1 from latent TGF-beta 1 "without inhibiting protease mediated cleavage of LAP region of latent TGF-beta 1" include antibodies that cause 50% or less, 45% or less, 40% or less, 35% or less, 30% or less, 25% or less, 20% or less, 15% or less, 10% or less, 5% or less decrease in protease mediated cleavage of LAP region of latent TGF-beta 1.

In some embodiments, an anti-latent TGF-beta 1 antibody stabilizes the structure of LAP region of the latent TGF-beta 1 without inhibiting the protease mediated cleavage of the LAP region of the latent TGF-beta 1. When an anti-latent TGF-beta 1 antibody "stabilize" the structure of LAP region, as used herein, the LAP region bounded by the anti-latent TGF-beta 1 antibody was kept in a certain structure from which mature TGF-beta 1 cannot be released. In further embodiments, latent TGF-beta 1 which is stabilized by an anti-latent TGF-beta 1 antibody can be activated by integrin (preferably integrin alpha V beta 8 and/or integrin alpha V beta 6). In certain embodiments, the LAP region which is stabilized by an anti-latent TGF-beta 1 antibody has been either cleaved or not cleaved by a protease. In some embodiments, an anti-latent TGF-beta 1 antibody stabilizes the structure of LAP region of the latent TGF-beta 1 and allows a protease to cleave the LAP region while the anti-latent TGF-beta 1 antibody binds to the LAP region of the latent TGF-beta 1. In some embodiments, an anti-latent TGF-beta 1 antibody stabilizes the structure of LAP region of the latent TGF-beta 1 without blocking access of a protease to latent TGF-beta 1, especially to the cleavage sites by PLN and/or PLK. In other embodiments, an anti-latent TGF-beta 1 antibody stabilizes the structure of LAP region of the latent TGF-beta 1 without blocking access of a protease to latent TGF-beta 1, especially to the cleavage sites by MMP2 and/or MMP9.

In one aspect, an anti-latent TGF-beta 1 antibody does not bind to mature TGF-beta 1. In some embodiments, an anti-latent TGF-beta 1 antibody binds to latent TGF-beta 1 with higher binding activity than mature TGF-beta 1. In certain embodiments, the antibodies of the present invention bind to latent TGF-beta 1 with at least 2, 3, 5, 10, 15, 20, 25, 30, 35, 40, 45, 50, 55, 60, 65, 70, 75, 80, 85, 90, 95, 100, 200, 400, 1000, 10000, or more times higher binding activity than to mature TGF-beta 1.

In one aspect, an anti-latent TGF-beta 1 antibody does not or does not significantly inhibit integrin mediated TGF-beta 1 activation, i.e, integrin mediated release of mature TGF-beta 1 from latent TGF-beta 1. Preferably the integrin here is integrin alpha V beta 8 and/or integrin alpha V beta 6. In some embodiments, antibodies "which does not or does not significantly inhibit integrin mediated TGF-beta 1 activation" include antibodies that cause 50% or less, 45% or less, 40% or less, 35% or less, 30% or less, 25% or less, 20% or less, 15% or less, 10% or less, 5% or less decrease in integrin mediated TGF-beta 1 activation, i.e, integrin mediated release of mature TGF-beta 1 from latent TGF-beta 1.

In one aspect, an anti-latent TGF-beta 1 antibody causes reduced or fewer toxicities and/or adverse effects associated with anti-TGF-beta antagonists. In some embodiments, anti-latent TGF-beta 1 antibodies, such as those described herein, have a superior safety-efficacy profile, as compared to agents that elicit activities towards mature TGF-beta 1 or agent that elicit activities towards latent TGF-beta 1 but inhibits both protease and integrin mediated activation of latent TGF-beta 1. In some embodiments, an anti-latent TGF-beta 1 antibody of the present disclosure has reduced cardiotoxicity while has efficacy better than or comparable with anti-mature TGF-beta 1 antibody. Without being bound by any theory, an anti-latent TGF-beta 1 antibody of the present disclosure does not or does not significantly inhibit integrin mediated TGF-beta 1 activation, and therefore has reduced or fewer toxicities and/or adverse effects which are caused by: (i) integrin mediated TGF-beta 1 activation or (ii) TGF-beta 1 signaling inhibition at sites where TGF-beta 1 is activated by integrin. An anti-latent TGF-beta 1 antibody of the present disclosure can therefore be administered to subjects in need thereof at a therapeutically effective dose without causing adverse effects, especially cardiotoxicity. Such approach would therefore broaden the dosage range in which both efficacy and safety/tolerability can be achieved in patients. Thus, the invention provides methods for treating a disease associated with TGF-beta 1 signaling, by administering to a subject an effective amount of an anti-latent TGF-beta 1 antibody which does not or does not significantly inhibit integrin mediated TGF-beta 1 activation. Use of an anti-latent TGF-beta 1 antibody for reducing toxicities and/or adverse effects associated with TGF-beta 1 inhibition in a subject is encompassed by the present invention. In some embodiments, toxicity and/or adverse effects may include cardiovascular toxicities, gastrointestinal toxicities, immune toxicities, bone/cartilage toxicities, reproductive toxicities, and renal toxicities. In some embodiments, cardiovascular toxicities include, but are not limited to: heart valve lesions, e.g., hemorrhage, inflammation, degeneration and proliferation of valvular interstitial cells. In some embodiments, toxicities and/or adverse effects may include bleeding. In some embodiments, toxicities and/or adverse effects may include skin lesions or tumors. In some embodiments, toxicities and/or adverse effects may include tumor progression.

In some embodiments, an anti-latent TGF-beta 1 antibody of the present invention:
  binds to latent TGF-beta 1;
  binds to latent TGF-beta 1 forming SLC;
  binds to latent TGF-beta 1 forming LLC;
  binds to latent TGF-beta 1 forming complex with GARP or LRRC33;
  binds to cell surface latent TGF-beta 1;
  binds to LAP region of latent TGF-beta 1;
  binds to LAP;
  binds to latent TGF-beta 1 with a dissociation constant (KD) of 10-8 nM or less, 10-9 nM or less, or 10-10 nM or less;
  inhibits protease mediated release of mature TGF-beta 1 from latent TGF-beta 1;
  does not inhibit protease mediated cleavage of LAP region of latent TGF-beta 1;
  does not or does not significantly inhibit integrin mediated release of mature TGF-beta 1 from latent TGF-beta 1; and/or
  causes reduced or fewer toxicities and/or adverse effects associated with anti-TGF-beta 1 antagonists, for example, anti-mature TGF-beta antibody.

In further embodiments, the anti-latent TGF-beta 1 antibody of the present invention is:
  a monoclonal antibody;
  a human, humanized or chimeric antibody;
  a full length of IgG antibody; and/or
  an antibody fragment.

In one aspect, the invention provides an anti-latent TGF-beta 1 antibody comprising at least one, two, three, four, five, or six HVRs selected from:
  (a) HVR-H1 comprising the amino acid sequence of SEQ ID NO: 20;
  (b) HVR-H2 comprising the amino acid sequence of SEQ ID NO: 21;
  (c) HVR-H3 comprising the amino acid sequence of SEQ ID NO: 22;
  (d) HVR-L1 comprising the amino acid sequence of SEQ ID NO: 23;
  (e) HVR-L2 comprising the amino acid sequence of SEQ ID NO: 24; and
  (f) HVR-L3 comprising the amino acid sequence of SEQ ID NO: 25.

In one aspect, the invention provides an anti-latent TGF-beta 1 antibody comprising at least one, two, three, four, five, or six HVRs selected from:
  (a) HVR-H1 comprising the amino acid sequence of SEQ ID NO: 26;

(b) HVR-H2 comprising the amino acid sequence of SEQ ID NO: 27;
(c) HVR-H3 comprising the amino acid sequence of SEQ ID NO: 28;
(d) HVR-L1 comprising the amino acid sequence of SEQ ID NO: 29;
(e) HVR-L2 comprising the amino acid sequence of SEQ ID NO: 30; and
(f) HVR-L3 comprising the amino acid sequence of SEQ ID NO: 31.

In one aspect, the invention provides an anti-latent TGF-beta 1 antibody comprising at least one, two, three, four, five, or six HVRs selected from:
(a) HVR-H1 comprising the amino acid sequence of SEQ ID NO: 32;
(b) HVR-H2 comprising the amino acid sequence of SEQ ID NO: 33;
(c) HVR-H3 comprising the amino acid sequence of SEQ ID NO: 34;
(d) HVR-L1 comprising the amino acid sequence of SEQ ID NO: 35;
(e) HVR-L2 comprising the amino acid sequence of SEQ ID NO: 36; and
(f) HVR-L3 comprising the amino acid sequence of SEQ ID NO: 37.

In one aspect, the invention provides an anti-latent TGF-beta 1 antibody comprising at least one, two, three, four, five, or six HVRs selected from:
(a) HVR-H1 comprising the amino acid sequence of SEQ ID NO: 38;
(b) HVR-H2 comprising the amino acid sequence of SEQ ID NO: 39;
(c) HVR-H3 comprising the amino acid sequence of SEQ ID NO: 40;
(d) HVR-L1 comprising the amino acid sequence of SEQ ID NO: 41;
(e) HVR-L2 comprising the amino acid sequence of SEQ ID NO: 42; and
(f) HVR-L3 comprising the amino acid sequence of SEQ ID NO: 43.

In one aspect, the invention provides an anti-latent TGF-beta 1 antibody comprising:
(a) HVR-H1 comprising the amino acid sequence of SEQ ID NO: 20;
(b) HVR-H2 comprising the amino acid sequence of SEQ ID NO: 21;
(c) HVR-H3 comprising the amino acid sequence of SEQ ID NO: 22;
(d) HVR-L1 comprising the amino acid sequence of SEQ ID NO: 23;
(e) HVR-L2 comprising the amino acid sequence of SEQ ID NO: 24; and
(f) HVR-L3 comprising the amino acid sequence of SEQ ID NO: 25.

In one aspect, the invention provides an anti-latent TGF-beta 1 antibody comprising:
(a) HVR-H1 comprising the amino acid sequence of SEQ ID NO: 26;
(b) HVR-H2 comprising the amino acid sequence of SEQ ID NO: 27;
(c) HVR-H3 comprising the amino acid sequence of SEQ ID NO: 28;
(d) HVR-L1 comprising the amino acid sequence of SEQ ID NO: 29;
(e) HVR-L2 comprising the amino acid sequence of SEQ ID NO: 30; and
(f) HVR-L3 comprising the amino acid sequence of SEQ ID NO: 31.

In one aspect, the invention provides an anti-latent TGF-beta 1 antibody comprising:
(a) HVR-H1 comprising the amino acid sequence of SEQ ID NO: 32;
(b) HVR-H2 comprising the amino acid sequence of SEQ ID NO: 33;
(c) HVR-H3 comprising the amino acid sequence of SEQ ID NO: 34;
(d) HVR-L1 comprising the amino acid sequence of SEQ ID NO: 35;
(e) HVR-L2 comprising the amino acid sequence of SEQ ID NO: 36; and
(f) HVR-L3 comprising the amino acid sequence of SEQ ID NO: 37.

In one aspect, the invention provides an anti-latent TGF-beta 1 antibody comprising:
(a) HVR-H1 comprising the amino acid sequence of SEQ ID NO: 38;
(b) HVR-H2 comprising the amino acid sequence of SEQ ID NO: 39;
(c) HVR-H3 comprising the amino acid sequence of SEQ ID NO: 40;
(d) HVR-L1 comprising the amino acid sequence of SEQ ID NO: 41;
(e) HVR-L2 comprising the amino acid sequence of SEQ ID NO: 42; and
(f) HVR-L3 comprising the amino acid sequence of SEQ ID NO: 43.

In one aspect, the invention provides an anti-Latent TGF-beta 1 antibody comprising HVR-H1, HVR-H2 and HVR-H3 of the VH sequence set forth in SEQ ID NO: 12, and HVR-L1, HVR-L2 and HVR-L3 of the VL sequence set forth in SEQ ID NO: 13, wherein the HVRs are defined by (a) Chothia; (b) Kabat; (c) MacCallum; or (d) combinations of (a), (b) and/or (c).

In one aspect, the invention provides an anti-Latent TGF-beta 1 antibody comprising HVR-H1, HVR-H2 and HVR-H3 of the VH sequence set forth in SEQ ID NO: 14, and HVR-L1, HVR-L2 and HVR-L3 of the VL sequence set forth in SEQ ID NO: 15, wherein the HVRs are defined by (a) Chothia; (b) Kabat; (c) MacCallum; or (d) combinations of (a), (b) and/or (c).

In one aspect, the invention provides an anti-Latent TGF-beta 1 antibody comprising HVR-H1, HVR-H2 and HVR-H3 of the VH sequence set forth in SEQ ID NO: 16, and HVR-L1, HVR-L2 and HVR-L3 of the VL sequence set forth in SEQ ID NO: 17, wherein the HVRs are defined by (a) Chothia; (b) Kabat; (c) MacCallum; or (d) combinations of (a), (b) and/or (c).

In one aspect, the invention provides an anti-Latent TGF-beta 1 antibody comprising HVR-H1, HVR-H2 and HVR-H3 of the VH sequence set forth in SEQ ID NO: 18, and HVR-L1, HVR-L2 and HVR-L3 of the VL sequence set forth in SEQ ID NO: 19, wherein the HVRs are defined by (a) Chothia; (b) Kabat; (c) MacCallum; or (d) combinations of (a), (b) and/or (c).

In any of the above embodiments, an anti-latent TGF-beta 1 antibody is humanized. In one embodiment, an anti-latent TGF-beta 1 antibody comprises HVRs as in any of the above embodiments, and further comprises an acceptor human framework, e.g. a human immunoglobulin framework or a human consensus framework.

In another aspect, an anti-latent TGF-beta 1 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 12, 14, 16 or 18. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-latent TGF-beta 1 antibody comprising that sequence retains the ability to bind to latent TGF-beta 1. In certain embodiments, a total of 1 to 10 amino acids have been substituted, inserted and/or deleted in SEQ ID NO: 12, 14, 16 or 18. In certain embodiments, substitutions, insertions, or deletions occur in regions outside the HVRs (i.e., in the FRs). Optionally, the anti-latent TGF-beta 1 antibody comprises the VH sequence in SEQ ID NO: 12, 14, 16 or 18, including post-translational modifications of that sequence. In a particular embodiment, the VH comprises one, two or three HVRs selected from: (a) HVR-H1 comprising the amino acid sequence of SEQ ID NO: 20, 26, 32 or 38, (b) HVR-H2 comprising the amino acid sequence of SEQ ID NO: 21, 27, 33 or 39, and (c) HVR-H3 comprising the amino acid sequence of SEQ ID NO: 22, 28, 34 or 40. Post-translational modifications include but are not limited to a modification of glutamine or glutamate in N-terminal of heavy chain or light chain to pyroglutamic acid by pyroglutamylation.

In another aspect, an anti-Latent TGF-beta 1 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 13, 15, 17 or 19. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-latent TGF-beta 1 antibody comprising that sequence retains the ability to bind to latent TGF-beta 1. In certain embodiments, a total of 1 to 10 amino acids have been substituted, inserted and/or deleted in SEQ ID NO: 13, 15, 17 or 19. In certain embodiments, the substitutions, insertions, or deletions occur in regions outside the HVRs (i.e., in the FRs). Optionally, the anti-latent TGF-beta 1 antibody comprises the VL sequence in SEQ ID NO: 13, 15, 17 or 19, including post-translational modifications of that sequence. In a particular embodiment, the VL comprises one, two or three HVRs selected from (a) HVR-L1 comprising the amino acid sequence of SEQ ID NO: 23, 29, 35 or 41; (b) HVR-L2 comprising the amino acid sequence of SEQ ID NO: 24, 30, 36 or 42; and (c) HVR-L3 comprising the amino acid sequence of SEQ ID NO: 25, 31, 37 or 43. Post-translational modifications include but are not limited to a modification of glutamine or glutamate in N-terminal of heavy chain or light chain to pyroglutamic acid by pyroglutamylation.

In another aspect, an anti-latent TGF-beta 1 antibody is provided, wherein the antibody comprises a VH as in any of the embodiments provided above, and a VL as in any of the embodiments provided above. In one embodiment, the antibody comprises the VH and VL sequences set forth in SEQ ID NO: 12 and SEQ ID NO: 13, respectively, including post-translational modifications of those sequences. Post-translational modifications include but are not limited to a modification of glutamine or glutamate in N-terminal of heavy chain or light chain to pyroglutamic acid by pyroglutamylation.

In one embodiment, the antibody comprises the VH and VL sequences set forth in SEQ ID NO: 14 and SEQ ID NO: 15, respectively, including post-translational modifications of those sequences. Post-translational modifications include but are not limited to a modification of glutamine or glutamate in N-terminal of heavy chain or light chain to pyroglutamic acid by pyroglutamylation.

In one embodiment, the antibody comprises the VH and VL sequences set forth in SEQ ID NO: 16 and SEQ ID NO: 17, respectively, including post-translational modifications of those sequences. Post-translational modifications include but are not limited to a modification of glutamine or glutamate in N-terminal of heavy chain or light chain to pyroglutamic acid by pyroglutamylation.

In one embodiment, the antibody comprises the VH and VL sequences set forth in SEQ ID NO: 18 and SEQ ID NO: 19, respectively, including post-translational modifications of those sequences. Post-translational modifications include but are not limited to a modification of glutamine or glutamate in N-terminal of heavy chain or light chain to pyroglutamic acid by pyroglutamylation.

In a further aspect, the invention provides an antibody that binds to the same epitope as an anti-latent TGF-beta 1 antibody provided herein. For example, in certain embodiments, an antibody is provided that binds to the same epitope as:

(1) An anti-latent TGF-beta 1 antibody comprising:
  (a) HVR-H1 comprising the amino acid sequence of SEQ ID NO: 20,
  (b) HVR-H2 comprising the amino acid sequence of SEQ ID NO: 21,
  (c) HVR-H3 comprising the amino acid sequence of SEQ ID NO: 22,
  (d) HVR-L1 comprising the amino acid sequence of SEQ ID NO: 23,
  (e) HVR-L2 comprising the amino acid sequence of SEQ ID NO: 24, and
  (f) HVR-L3 comprising the amino acid sequence of SEQ ID NO: 25;

(2) An anti-latent TGF-beta 1 antibody comprising:
  (a) HVR-H1 comprising the amino acid sequence of SEQ ID NO: 26,
  (b) HVR-H2 comprising the amino acid sequence of SEQ ID NO: 27,
  (c) HVR-H3 comprising the amino acid sequence of SEQ ID NO: 28,
  (d) HVR-L1 comprising the amino acid sequence of SEQ ID NO: 29,
  (e) HVR-L2 comprising the amino acid sequence of SEQ ID NO: 30, and
  (f) HVR-L3 comprising the amino acid sequence of SEQ ID NO: 31;

(3) An anti-latent TGF-beta 1 antibody comprising:
  (a) HVR-H1 comprising the amino acid sequence of SEQ ID NO: 32,
  (b) HVR-H2 comprising the amino acid sequence of SEQ ID NO: 33,
  (c) HVR-H3 comprising the amino acid sequence of SEQ ID NO: 34,
  (d) HVR-L1 comprising the amino acid sequence of SEQ ID NO: 35,
  (e) HVR-L2 comprising the amino acid sequence of SEQ ID NO: 36, and
  (f) HVR-L3 comprising the amino acid sequence of SEQ ID NO: 37; or (4) An anti-latent TGF-beta 1 antibody comprising:
  (a) HVR-H1 comprising the amino acid sequence of SEQ ID NO: 38,
  (b) HVR-H2 comprising the amino acid sequence of SEQ ID NO: 39, (c) HVR-H3 comprising the amino acid sequence of SEQ ID NO: 40,
(d) HVR-L1 comprising the amino acid sequence of SEQ ID NO: 41,
(e) HVR-L2 comprising the amino acid sequence of SEQ ID NO: 42, and
(f) HVR-L3 comprising the amino acid sequence of SEQ ID NO: 43.

In a further aspect, the invention provides an antibody that binds to latent TGF-beta 1 of human, monkey, mouse, and/or rat. In certain embodiments, the invention provides an antibody that binds to latent TGF-beta 1 of human, monkey and mouse. In certain embodiments, the invention provides an antibody which binds to latent TGF-beta 1 forming SLC of human, monkey and mouse. In certain embodiments, the invention provides an antibody which binds to latent TGF-beta 1 forming LLC of human, monkey and mouse. In certain embodiments, the invention provides an antibody which binds to latent TGF-beta 1 forming LLC of human, monkey and mouse. In certain embodiments, the invention provides an antibody which binds to latent TGF-beta 1 forming complex with GARP or LRRC33 of human, monkey and mouse. In certain embodiments, the invention provides an antibody which binds to cell surface latent TGF-beta 1 of human, monkey and mouse.

In a further aspect, the invention provides an antibody that binds to the same epitope as any one of the anti-latent TGF-beta 1 antibodies provided herein. The epitope may exist on TGF-beta 1 of human, monkey, mouse and/or rat. For example, in certain embodiments, the invention provides an antibody that binds the same epitope as a reference antibody, wherein the reference antibody is:

(1) An anti-latent TGF-beta 1 antibody comprising:
   (a) HVR-H1 comprising the amino acid sequence of SEQ ID NO: 20,
   (b) HVR-H2 comprising the amino acid sequence of SEQ ID NO: 21,
   (c) HVR-H3 comprising the amino acid sequence of SEQ ID NO: 22,
   (d) HVR-L1 comprising the amino acid sequence of SEQ ID NO: 23,
   (e) HVR-L2 comprising the amino acid sequence of SEQ ID NO: 24, and
   (f) HVR-L3 comprising the amino acid sequence of SEQ ID NO: 25;
(2) An anti-latent TGF-beta 1 antibody comprising:
   (a) HVR-H1 comprising the amino acid sequence of SEQ ID NO: 26,
   (b) HVR-H2 comprising the amino acid sequence of SEQ ID NO: 27,
   (c) HVR-H3 comprising the amino acid sequence of SEQ ID NO: 28,
   (d) HVR-L1 comprising the amino acid sequence of SEQ ID NO: 29,
   (e) HVR-L2 comprising the amino acid sequence of SEQ ID NO: 30, and
   (f) HVR-L3 comprising the amino acid sequence of SEQ ID NO: 31;
(3) An anti-latent TGF-beta 1 antibody comprising:
   (a) HVR-H1 comprising the amino acid sequence of SEQ ID NO: 32,
   (b) HVR-H2 comprising the amino acid sequence of SEQ ID NO: 33,
   (c) HVR-H3 comprising the amino acid sequence of SEQ ID NO: 34,
   (d) HVR-L1 comprising the amino acid sequence of SEQ ID NO: 35,
   (e) HVR-L2 comprising the amino acid sequence of SEQ ID NO: 36, and
   (f) HVR-L3 comprising the amino acid sequence of SEQ ID NO: 37; or
(4) An anti-latent TGF-beta 1 antibody comprising:
   (a) HVR-H1 comprising the amino acid sequence of SEQ ID NO: 38,
   (b) HVR-H2 comprising the amino acid sequence of SEQ ID NO: 39,
   (c) HVR-H3 comprising the amino acid sequence of SEQ ID NO: 40,
   (d) HVR-L1 comprising the amino acid sequence of SEQ ID NO: 41,
   (e) HVR-L2 comprising the amino acid sequence of SEQ ID NO: 42, and
   (f) HVR-L3 comprising the amino acid sequence of SEQ ID NO: 43.

In a further aspect, the invention provides an antibody that competes with an anti-latent TGF-beta 1 antibody provided herein for binding to TGF-beta 1 of human, monkey, mouse and/or rat. For example, in certain embodiments, an antibody is provided that competes for binding to TGF-beta 1 of human, monkey, mouse and/or rat with:

(1) An anti-latent TGF-beta 1 antibody comprising:
   (a) HVR-H1 comprising the amino acid sequence of SEQ ID NO: 20,
   (b) HVR-H2 comprising the amino acid sequence of SEQ ID NO: 21,
   (c) HVR-H3 comprising the amino acid sequence of SEQ ID NO: 22,
   (d) HVR-L1 comprising the amino acid sequence of SEQ ID NO: 23,
   (e) HVR-L2 comprising the amino acid sequence of SEQ ID NO: 24, and
   (f) HVR-L3 comprising the amino acid sequence of SEQ ID NO: 25;
(2) An anti-latent TGF-beta 1 antibody comprising:
   (a) HVR-H1 comprising the amino acid sequence of SEQ ID NO: 26,
   (b) HVR-H2 comprising the amino acid sequence of SEQ ID NO: 27,
   (c) HVR-H3 comprising the amino acid sequence of SEQ ID NO: 28,
   (d) HVR-L1 comprising the amino acid sequence of SEQ ID NO: 29,
   (e) HVR-L2 comprising the amino acid sequence of SEQ ID NO: 30, and
   (f) HVR-L3 comprising the amino acid sequence of SEQ ID NO: 31;
(3) An anti-latent TGF-beta 1 antibody comprising:
   (a) HVR-H1 comprising the amino acid sequence of SEQ ID NO: 32,
   (b) HVR-H2 comprising the amino acid sequence of SEQ ID NO: 33,
   (c) HVR-H3 comprising the amino acid sequence of SEQ ID NO: 34,
   (d) HVR-L1 comprising the amino acid sequence of SEQ ID NO: 35,
   (e) HVR-L2 comprising the amino acid sequence of SEQ ID NO: 36, and
   (f) HVR-L3 comprising the amino acid sequence of SEQ ID NO: 37; or
(4) An anti-latent TGF-beta 1 antibody comprising:
   (a) HVR-H1 comprising the amino acid sequence of SEQ ID NO: 38,
   (b) HVR-H2 comprising the amino acid sequence of SEQ ID NO: 39, (c) HVR-H3 comprising the amino acid sequence of SEQ ID NO: 40,
(d) HVR-L1 comprising the amino acid sequence of SEQ ID NO: 41,
(e) HVR-L2 comprising the amino acid sequence of SEQ ID NO: 42, and
(f) HVR-L3 comprising the amino acid sequence of SEQ ID NO: 43.

In a further aspect of the invention, an anti-latent TGF-beta 1 antibody according to any of the above embodiments is a monoclonal antibody, including a chimeric, humanized or human antibody. In one embodiment, an anti-latent TGF-beta 1 antibody is an antibody fragment, e.g., a Fv, Fab, Fab', scFv, diabody, or F(ab')2 fragment. In another embodiment, the antibody is a full length antibody, e.g., an intact IgG1, IgG2, IgG3 or IgG4 antibody or other antibody class or isotype as defined herein. In a further aspect, an anti-latent TGF-beta 1 antibody also includes any antigen binding molecule which comprises a variable heavy chain and/or variable light chain structure of immunoglobulin.

In a further aspect, an anti-latent TGF-beta 1 antibody according to any of the above embodiments may incorporate any of the features, singly or in combination, as described in Sections 1-7 below:

1. Antibody Binding Activity

In certain embodiments, an antibody provided herein has a dissociation constant (KD) of 1 micromolar or less, 100 nM or less, 10 nM or less, 1 nM or less, 0.1 nM or less, 0.01 nM or less, or 0.001 nM or less (e.g. 10-8 M or less, e.g. from 10-8 M to 10-13 M, e.g., from 10-9 M to 10-13 M).

In one embodiment, binding activity of an antibody is measured by a radiolabeled antigen binding assay (RIA) and represented by KD. In one embodiment, an RIA is performed with the Fab version of an antibody of interest and its antigen. For example, solution binding activity of Fabs for antigen is measured by equilibrating Fab with a minimal concentration of (125I)-labeled antigen in the presence of a titration series of unlabeled antigen, then capturing bound antigen with an anti-Fab antibody-coated plate (see, e.g., Chen et al., J. Mol. Biol. 293:865-881(1999)). To establish conditions for the assay, MICROTITER (registered trademark) multi-well plates (Thermo Scientific) are coated overnight with 5 microgram/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23 degrees Celsius (C)). In a non-adsorbent plate (Nunc #269620), 100 pM or 26 pM [125I]-antigen are mixed with serial dilutions of a Fab of interest (e.g., consistent with assessment of the anti-VEGF antibody, Fab-12, in Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20 (registered trademark)) in PBS. When the plates have dried, 150 microliter/well of scintillant (MICROSCINT-20 ™; Packard) is added, and the plates are counted on a TOPCOUNT™ gamma counter (Packard) for ten minutes. Concentrations of each Fab that give less than or equal to 20% of maximal binding are chosen for use in competitive binding assays.

In one embodiment, for measuring binding activity of an antibody, ligand-capturing methods, for example, using BIACORE (registered trademark) T200 or BIACORE (registered trademark) 4000 (GE Healthcare, Uppsala, Sweden), which rely upon surface plasmon resonance analysis methods as the measurement principle, are used. BIACORE (registered trademark) Control Software is used for operation of devices. In one embodiment, amine-coupling kit (GE Healthcare, Uppsala, Sweden) is used according to the manufacturer's instructions to let a molecule for ligand capturing, for example, an anti-tag antibody, an anti-IgG antibody, protein A, etc. fixed onto a sensor chip (GE Healthcare, Uppsala, Sweden) coated with carboxymethyl-dextran. The ligand-capturing molecule is diluted with a 10 mM sodium acetate solution at an appropriate pH and is injected at an appropriate flow rate and for an appropriate injection time. Binding activity measurements are measured using a 0.05% polysorbate 20 (in other name Tween (registered trademark)-20)-containing buffer as a measurement buffer, at a flow rate of 10-30 microliter/minute, and at a measurement temperature of preferably at 25 degrees C. or 37 degrees C. For the measurement carried out with an antibody captured by the ligand-capturing molecule as a ligand, an antibody is injected to let a target amount of the antibody captured, and then a serial dilution of an antigen and/or an Fc receptor (analyte) prepared using the measurement buffer is injected. For the measurement carried out with an antigen and/or an Fc receptor captured by the ligand-capturing molecule as a ligand, an antigen and/or an Fc receptor is injected to let a target amount thereof captured, and then a serial dilution of an antibody (analyte) prepared using the measurement buffer is injected.

In one embodiment, the measurement results are analyzed using BIACORE (registered trademark) Evaluation Software. Kinetics parameter calculation is carried out by fitting sensorgrams of association and dissociation at the same time using a 1:1 binding model, and an association rate (kon or ka), a dissociation rate (koff or kd), and an equilibrium dissociation constant (KD) may be calculated. For the case of weak binding activity, in particular, for the cases where dissociation is fast and kinetics parameters are difficult to calculate, the Steady state model may be used to calculate the equilibrium dissociation constant (KD). As additional parameters concerning binding activity, "binding amount of analyte per unit ligand amount" may be calculated by dividing a binding amount of analyte (resonance unit: RU) at a specific concentration by an amount of captured ligand.

2. Antibody Fragments

In certain embodiments, an antibody provided herein is an antibody fragment. Antibody fragments include, but are not limited to, Fab, Fab', Fab'-SH, F(ab')2, Fv, and scFv fragments, and other fragments described below. For a review of certain antibody fragments, see Hudson et al. Nat. Med. 9:129-134 (2003). For a review of scFv fragments, see, e.g., Pluckthun, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. E. coli or phage), as described herein.

The present invention also relates to antigen-binding molecules which bind to TGF-beta 1, which include, but are not limited to, for example, minibodies (low molecular weight antibodies), and scaffold proteins. In the present invention, any scaffold protein is acceptable as long as it is a peptide that has a stable three-dimensional structure and is capable of binding to at least an antigen. Such peptides include, for example, fragments of antibody variable regions, fibronectin, protein A domain, LDL receptor A domain, lipocalin, and other molecules described in Nygren et al. (Current Opinion in Structural Biology, (1997) 7:463-469; Journal of Immunol Methods, (2004) 290:3-28), Binz et al. (Nature Biotech. (2005) 23:1257-1266), and Hosse et al. (Protein Science, (2006) 15:14-27). When referring to such an antibody, e.g., "anti-latent TGF-beta 1 antibody" should be replaced with "anti-latent TGF-beta 1 antigen-binding molecule" in the context of the present specification.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and binding activity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or binding activity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENO-MOUSE™ technology; U.S. Pat. No. 5,770,429 describing HUMAB (registered trademark) technology; U.S. Pat. No. 7,041,870 describing K-M MOUSE (registered trademark) technology, and U.S. Patent Application Publication No. US 2007/0061900, describing VELOCIMOUSE (registered trademark) technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).) Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in Methods in Molecular Biology 178: 1-37 (O'Brien et al., ed., Human Press, Totowa, N.J., 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, N.J., 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., Ann. Rev. Immunol., 12: 433-455 (1994). Phage typically display antibody fragments, either as single-chain Fv (scFv) fragments or as Fab fragments. Libraries from immunized sources provide high-binding activity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., EMBO J, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, J. Mol. Biol., 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for TGF-beta 1 and the other is for any other antigen. In certain embodiments, bispecific antibodies may bind to two different epitopes of TGF-beta 1. Bispecific antibodies may also be used to localize cytotoxic agents to cells which express TGF-beta 1. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, Nature 305: 537 (1983)), WO 93/08829, and Traunecker et al., EMBO J. 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (scFv) dimers (see, e.g. Gruber et al., J. Immunol., 152:5368 (1994)); and preparing trispecific antibodies as described, e.g., in Tutt et al. J. Immunol. 147: 60 (1991).

Engineered antibodies with three or more functional antigen binding sites, including "Octopus antibodies," are also included herein (see, e.g. US 2006/0025576A1).

The antibody or fragment herein also includes a "Dual Acting Fab" or "DAF" comprising an antigen binding site that binds to TGF-beta 1 as well as another, different antigen (see, US 2008/0069820, for example).

7. Antibody Variants

In certain embodiments, amino acid sequence variants of the antibodies provided herein are contemplated. For example, it may be desirable to improve the binding activity and/or other biological properties of the antibody Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |

TABLE 1-continued

| Original Residue | Exemplary Substitutions | Preferred Substitutions |
|---|---|---|
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.
Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased binding activity, reduced immunogenicity) relative to the parent antibody and/or will have substantially retained certain biological properties of the parent antibody. An exemplary substitutional variant is a binding activity matured antibody, which may be conveniently generated, e.g., using phage display-based binding activity maturation techniques such as those described herein. Briefly, one or more HVR residues are mutated and the variant antibodies displayed on phage and screened for a particular biological activity (e.g. binding activity).

Alterations (e.g., substitutions) may be made in HVRs, e.g., to improve antibody binding activity. Such alterations may be made in HVR "hotspots," i.e., residues encoded by codons that undergo mutation at high frequency during the somatic maturation process (see, e.g., Chowdhury, Methods Mol. Biol. 207:179-196 (2008)), and/or residues that contact antigen, with the resulting variant VH or VL being tested for binding activity. Binding activity maturation by constructing and reselecting from secondary libraries has been described, e.g., in Hoogenboom et al. in Methods in Molecular Biology 178:1-37 (O'Brien et al., ed., Human Press, Totowa, N.J., (2001).) In some embodiments of binding activity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired binding activity. Another method to introduce diversity involves HVR-directed approaches, in which several HVR residues (e.g., 4-6 residues at a time) are randomized HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding activity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex may be analyzed to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion of an enzyme (e.g. for ADEPT) or a polypeptide which increases the plasma half-life of the antibody to the N- or C-terminus of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about +/−3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. Biotech. Bioeng. 87: 614 (2004). Examples of cell lines capable of producing defucosylated antibodies include Lec13 CHO cells deficient in protein fucosylation (Ripka et al. Arch. Biochem. Biophys. 249: 533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

(c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions. In another embodiment, a human Fc variant may comprise a chimeric human Fc region sequence (e.g., a human IgG1/4 or human IgG2/4 Fc region), or a chimeric human Fc region sequence which further comprises an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks Fc gamma R binding (hence likely lacking ADCC activity), but retains FcRn binding ability. The primary cells for mediating ADCC, NK cells, express Fc gamma RIII only, whereas monocytes express Fc gamma RI, Fc gamma RII and Fc gamma RIII. FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g. Hellstrom, I. et al. Proc. Nat'l Acad. Sci. USA 83:7059-7063 (1986)) and Hellstrom, I et al., Proc. Nat'l Acad. Sci. USA 82:1499-1502 (1985); U.S. Pat. No. 5,821,337 (see Bruggemann, M. et al., J. Exp. Med. 166:1351-1361 (1987)). Alternatively, non-radioactive assays methods may be employed (see, for example, ACT1™ non-radioactive cytotoxicity assay for flow cytometry (CellTechnology, Inc. Mountain View, Calif.; and CytoTox 96 (registered trademark) non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. Proc. Nat'l Acad. Sci. USA 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., J. Immunol. Methods 202:163 (1996); Cragg, M. S. et al., Blood 101:1045-1052 (2003); and Cragg, M. S. and M. J. Glennie, Blood 103:2738-2743 (2004)). FcRn binding and in vivo clearance/half life determinations can also be performed using methods known in the art (see, e.g., Petkova, S. B. et al., Intl. Immunol. 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with increased or decreased binding to FcRs are described. (See, e.g., U.S. Pat. No. 6,737,056; WO 2004/056312, and Shields et al., J. Biol. Chem. 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either increased or decreased) C1q binding and/or Complement Dependent Cytotoxicity (CDC), e.g., as described in U.S. Pat. No. 6,194,551, WO 99/51642, and Idusogie et al. J. Immunol. 164: 4178-4184 (2000).

Antibodies with increased half lives and increased binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). Those antibodies comprise an Fc region with one or more substitutions therein which increase binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, Nature 322:738-40 (1988); U.S. Pat. Nos. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, polypropylene glycol homopolymers, polypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-latent TGF-beta 1 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp2/0 cell). In one embodiment, a method of making an anti-latent TGF-beta 1 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-latent TGF-beta 1 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in E. coli.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22:1409-1414 (2004), and Li et al., Nat. Biotech. 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK); buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR⁻ CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

C. Assays

Anti-latent TGF-beta 1 antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, surface plasmon resonance (e.g. BIA-CORE(registered trademark)) or a similar technique (e.g. KinExa or OCTET(registered trademark)), etc.

In another aspect, competition assays may be used to identify an antibody that competes with any anti-latent TGF-beta 1 antibodies described herein, preferably hT0947AE04-SG191, hT0947AE07-SG191, hT0947AE08-SG191 or hT0947AE09-SG191 for binding to latent TGF-beta 1. In certain embodiments, such a competing antibody binds to the same epitope (e.g., a linear or a conformational epitope) that is bound by any anti-latent TGF-beta 1 antibodies described herein, preferably hT0947AE04-SG191, hT0947AE07-SG191, hT0947AE08-SG191 or hT0947AE09-SG191. Detailed exemplary methods for mapping an epitope to which an antibody binds are provided in Morris (1996) "Epitope Mapping Protocols," in Methods in Molecular Biology vol. 66 (Humana Press, Totowa, N.J.). Methods for mapping an epitope include but not limited to, X-ray crystallography and alanine scanning mutagenesis methods.

In certain embodiments, when such a competing antibody is present in excess, it blocks (e.g., reduces) the binding of a reference antibody to latent TGF-beta 1 by at least 10%, 15%, 20%, 25%, 30%, 35%, 40%, 45%, 50%, 55%, 60%, 65%, 70%, 75% or more. In some instances, binding is inhibited by at least 80%, 85%, 90%, 95%, or more. In certain embodiments, such a competing antibody binds to the same epitope (e.g., a linear epitope or a conformational epitope) that is bound by an anti-latent TGF-beta 1 antibody described herein. In further aspects, the reference antibody is hT0947AE04-SG191, hT0947AE07-SG191, hT0947AE08-SG191 or hT0947AE09-SG191.

In an exemplary competition assay, immobilized latent TGF-beta 1 is incubated in a solution comprising a first labeled antibody (a reference antibody) that binds to latent TGF-beta 1 (e.g., hT0947AE04-SG191, hT0947AE07-SG191, hT0947AE08-SG191 or hT0947AE09-SG191.) and a second unlabeled antibody that is being tested for its ability to compete with the first antibody for binding to latent TGF-beta 1. The second antibody may be present in a hybridoma supernatant. As a control, immobilized latent TGF-beta 1 is incubated in a solution comprising the first labeled antibody but not the second unlabeled antibody. After incubation under conditions permissive for binding of the first antibody to latent TGF-beta 1, excess unbound antibody is removed, and the amount of label associated with immobilized latent TGF-beta 1 is measured. If the amount of label associated with immobilized latent TGF-beta 1 is substantially reduced in the test sample relative to the control sample, then that indicates that the second antibody is competing with the first antibody for binding to latent TGF-beta 1. See Harlow and Lane (1988) Antibodies: A Laboratory Manual ch. 14 (Cold Spring Harbor Laboratory, Cold Spring Harbor, N.Y.).

In certain embodiments, binding of an anti-latent TGF-beta 1 antibody to a cell surface latent TGF-beta 1 can be tested by known methods such as ELISA, Western blot, BIAcore, Flow cytometry, etc. For example, cells expressing latent TGF-beta 1 can be brought into contact with either anti-latent TGF-beta 1 antibodies directly conjugated with PE- or APC-, or unconjugated anti-latent TGF-beta 1 antibodies followed by PE- or APC-conjugated secondary antibodies, and the staining of cell surface latent TGF-beta 1 can be detected. See, e.g., Oida et al., PLoS One. 2010 Nov. 24; 5(11):e15523; Su et al, Hum Mol Genet. 2015 Jul. 15; 24(14):4024-36.

2. Activity Assays

In one aspect, assays are provided for identifying anti-latent TGF-beta 1 antibodies thereof having biological activity. Biological activity may include, e.g., inhibiting activation of latent TGF-beta 1, inhibiting the release of mature TGF-beta 1 from latent TGF-beta 1, inhibiting protease mediated release of mature TGF-beta 1 from latent TGF-beta 1, inhibiting protease mediated release of mature TGF-beta 1 from latent TGF-beta 1 without inhibiting protease mediated cleavage of the LAP region of latent TGF-beta 1, inhibiting protease mediated release of mature TGF-beta 1 from latent TGF-beta 1 without blocking access of a protease to latent TGF-beta 1, inhibiting protease mediated release of mature TGF-beta 1 from latent TGF-beta 1 while allowing a protease to cleave the LAP region of the latent TGF-beta 1, inhibiting protease mediated release of mature TGF-beta 1 from latent TGF-beta 1 without inhibiting or with partially inhibiting integrin mediated TGF-beta 1 activation, etc. Antibodies having such biological activity in vivo and/or in vitro are also provided.

In certain embodiments, an antibody of the invention is tested for such biological activity.

In some embodiments, whether a test antibody inhibits activation of latent TGF-beta 1, i.e., inhibits the release of mature TGF-beta 1 from latent TGF-beta 1, is determined by detecting mature TGF-beta 1 using a method known in the art such as electrophoresis, chromatography, immunoblot analysis, an enzyme-linked immunosorbent assay (ELISA), or mass spectrometry, after an activator of latent TGF-beta 1 (e.g., protease, integrin, other non-protease activator, etc.) is contacted with latent TGF-beta 1 in the presence or absence of the test antibody. In one example, an activator can be isolated (e.g., isolated protease or integrin) and/or non-isolated (e.g, mouse, monkey or human PBMC comprising integrin). It is also known that the activation latent TGF-beta 1, i.e., the release of mature TGF-beta 1 from latent TGF-beta 1, also occurs in the absence of an activator (spontaneous activation of latent TGF-beta 1). In some embodiments, whether a test antibody inhibits spontaneous activation of latent TGF-beta 1 is determined by detecting mature TGF-beta 1 using the method described above, after latent TGF-beta 1 is incubated with or without the test antibody. In some embodiments, where a decreased amount of mature TGF-beta 1 is detected in the presence of (or following contact with) the test antibody as compared to the amount detected in the absence of the test antibody, the test antibody is identified as an antibody that can inhibit the activation of latent TGF-beta 1. In an example, the amount of mature TGF-beta 1, either decreased or increased, can be measured in terms of concentration of mature TGF-beta 1 (for example, g/ml, mg/ml, microgram/ml, ng/ml, or pg/ml, etc.). In another example, the amount of mature TGF-beta, either decreased or increased, can be measured in terms of optical density (O.D.) (for example, at a wavelength in mm or nm, etc.) of a label directly or indirectly associated with mature TGF-beta.

In certain embodiments, inhibition of TGF-beta 1 activation includes at least a 5%, 10%, 15%, 20%, 25%, 30%, 35%, or 40% or greater decrease in the amount of mature TGF-beta 1 in the assay as compared to a negative control under similar conditions. In some embodiments, it refers to the inhibition of TGF-beta 1 activation i.e., the inhibition of the release of mature TGF-beta 1 of at least 45%, 50%, 55%, 60%, 65%, 70%, 75%, 80%, 85%, 90%, or 95% or greater.

In some embodiments, whether a test antibody inhibits activation of latent TGF-beta 1, i.e., inhibits the release of mature TGF-beta 1 from latent TGF-beta 1, is also determined by detecting mature TGF-beta 1 activity, for example, the activity of binding to TGF-beta 1 receptor, or the activity of mediating signal transduction in a cell expressing TGF-beta 1 receptor, etc. In some embodiments, binding of mature TGF-beta 1 to TGF-beta 1 receptor can be detected using a receptor binding assay. In some embodiments, the activity of mediating TGF-beta 1 signal transduction can be determined by detecting the activation of the TGF-beta 1/Smad pathway. Cells useful for such an assay can be those that express endogenous TGF-beta 1 receptor or that were generated by transfection of cells with a TGF-beta 1 receptor gene. For example, HEK-Blue™ TGF-beta cell which was used in the working examples described herein, or those that are genetically modified, transiently or stably, to express a transgene encoding TGF-beta 1 receptor can be used. TGF-beta 1 mediated signal transduction can be detected at any level in the signal transduction pathway, for example, by examining phosphorylation of Smad polypeptide, examining expression of a TGF-beta 1 regulated gene including a reporter gene, or measuring proliferation of a TGF-beta 1-dependent cell.

In some embodiments, the activity of mediating TGF-beta 1 signal transduction can also be determined by detecting the activation of the TGF-beta 1/Smad pathway, by examining phosphorylation of Smad polypeptide (see, e.g., Fukasawa et. al., Kidney International. 65(1):63-74 (2004), and Ganapathy et al., Molecular Cancer 26; 9:122 (2010)). In other embodiments, the activity of mediating TGF-beta 1 signal transduction can be determined by examining the ability of TGF-beta to inhibit cell migration in "wounded" monolayer cultures of BAE cells, examining the ability of TGF-beta to inhibit cell growth, examining the ability of TGF-beta to suppress plasminogen activator (PA) activity, examining the ability of TGF-beta to upregulate plasminogen activator inhibitor-1 (PAI-1), etc. (see Mazzieri et. al., Methods in Molecular Biology 142:13-27(2000))

Inhibition of TGF-beta 1 activation can also be detected and/or measured using the methods set forth and exemplified in the working examples. Using assays of these or other suitable types, test antibodies can be screened for those capable of inhibiting the activation of TGF-beta 1. In certain embodiments, inhibition of TGF-beta 1 activation includes at least a 5%, 10%, 15%, 20%, 25%, 30%, 35%, or 40% or greater decrease in TGF-beta 1 activation in the assay as compared to a negative control under similar conditions. In some embodiments, it refers to the inhibition of TGF-beta 1 activation of at least 45%, 50%, 55%, 60%, 65%, 70%, 75%, 80%, 85%, 90%, or 95% or greater. In certain embodiments, inhibition of TGF-beta 1 activation includes at least a 5%, 10%, 15%, 20%, 25%, 30%, 35%, or 40% or greater decrease in the amount of mature TGF-beta 1 detected in the assay as compared to a negative control under similar conditions. In some embodiments, it refers to the decrease in the amount of mature TGF-beta 1 of at least 45%, 50%, 55%, 60%, 65%, 70%, 75%, 80%, 85%, 90%, or 95% or greater.

In some embodiments, whether a test antibody inhibits the cleavage of the LAP portion of latent TGF-beta 1 is determined by detecting the cleavage product of latent TGF-beta 1 and/or non-cleaved latent TGF-beta 1 using various methods known in the art such as electrophoresis, chromatography, immunoblot analysis, an enzyme-linked immunosorbent assay (ELISA), or mass spectrometry, after a protease is contacted with latent TGF-beta 1 in the presence or absence of the test antibody. For example, where a protein tag (e.g., FLAG-tag, etc.) is added to N-terminal of the LAP region of latent TGF-beta 1, the portion to which the protein tag added is cut off when the protease mediated cleavage occurs. Therefore, the cleavage product of latent TGF-beta 1 can be detected by detecting latent TGF-beta 1 (or LAP region of latent TGF-beta 1) without the protein tag, and/or the non-cleaved latent TGF-beta 1 can be detected by detecting latent TGF-beta 1 with the protein tag.

For another example, where a protein tag (e.g., FLAG-tag, etc.) is added to the N-terminal of the LAP region of latent TGF-beta 1, and where the location of cleavage site by a protease is not near the N-terminal of the LAP region of latent TGF-beta 1, the LAP region with the protein tag becomes shortened when the protease mediated cleavage occurs. Therefore, the cleavage product of latent TGF-beta 1 can be detected by detecting latent TGF-beta 1 having a shortened LAP region (or shortened LAP region of latent TGF-beta 1) with the protein tag.

In some embodiments, where a decreased amount of the cleavage product of latent TGF-beta 1 is detected in the presence of (or following contact with) the test antibody as compared to the amount detected in the absence of the test antibody, the test antibody is identified as an antibody that can inhibit the cleavage of latent TGF-beta 1. Conversely, where the amount of the cleavage product of latent TGF-beta 1 is not significantly decreased in the presence of (or following contact with) the test antibody as compared to the amount detected in the absence of the test antibody, the test antibody is identified as an antibody that does not inhibit the cleavage of latent TGF-beta 1. In some embodiments, where an increased amount of the non-cleaved latent TGF-beta 1 is detected in the presence of (or following contact with) the test antibody as compared to the amount detected in the absence of the test antibody, the test antibody is identified as an antibody that can inhibit the cleavage of latent TGF-beta 1. Conversely, where an amount of non-cleaved latent TGF-beta 1 is not significantly increased in the presence of (or following contact with) the test antibody as compared to the amount detected in the absence of the test antibody, the test antibody is identified as an antibody that does not inhibit the cleavage of latent TGF-beta 1. In certain embodiments, whether a test antibody blocks access of a protease to latent TGF-beta 1 is determined by methods for the detection of protein interactions between the protease and latent TGF-beta 1, e.g., ELISA or surface plasmon resonance (e.g. BIACORE(registered trademark)) or a similar technique (e.g. KinExa or OCTET(registered trademark)). Where a decreased interaction between the protease and latent TGF-beta 1 is detected in the presence of (or following contact with) the test antibody as compared to the interaction detected in the absence of the test antibody, the test antibody is identified as an antibody that can block access of the protease to latent TGF-beta 1.

In certain embodiments, non-inhibition of the cleavage of latent TGF-beta 1 includes at least a 5%, 10%, 15%, 20%, 25%, 30%, 35%, or 40% or greater increase in the amount of the cleavage product of latent TGF-beta 1 in the assay as compared to a negative control under similar conditions. In some embodiments, non-inhibition of the cleavage of latent TGF-beta 1 includes at least 50% or less, 45% or less, 40% or less, 35% or less, 30% or less, 25% or less, 20% or less, 15% or less, 10% or less, 5% or less increase in the amount of the non-cleaved latent TGF-beta 1 in the assay as compared to a negative control under similar conditions.

In some embodiments, an anti-latent TGF-beta 1 antibody may be subjected to other biological activity assays, e.g., in order to evaluate its effectiveness as a therapeutic. Such assays are known in the art and depend on the target antigen and intended use for the antibody. For example, the biological effects of TGF-beta 1 blockade by the anti-latent TGF-beta 1 antibody can be assessed in a Unilateral Ureteral Obstruction (UUO) induced mouse renal fibrosis model (e.g., as described in Chevalier R L et al., Ureteral obstruction as a model of renal interstitial fibrosis and obstructive nephropathy. Kidney Int. 2009 June; 75(11):1145-1152.), a choline-deficient, L-amino acid-defined, high-fat diet (CDAHFD)-induced NASH/liver fibrosis mouse model, a bleomycin (BLM)-induced lung fibrosis mouse model, and/or a syngeneic tumor model (e.g., as described in Mariathasan S et al., TGF-beta attenuates tumour response to PD-L1 blockade by contributing to exclusion of T cells. Nature. 2018 Feb. 22; 554(7693):544-548.). In further embodiments, the anti-latent TGF-beta 1 antibody may be subject to biological activity assays described herein.

3. Methods for Screening

In one aspect, a method for screening an antibody of the invention comprises various assays described herein and known in the art. For example, a method for screening an anti-latent TGF-beta 1 antibody comprises:
(a) contacting a biological sample comprising latent TGF-beta 1 and a protease with a test antibody;
(b) detecting (i) whether a test antibody inhibits the cleavage of the LAP region of latent TGF-beta 1 and (ii) whether a test antibody inhibits activation of latent TGF-beta 1; and
(c) selecting the test antibody that inhibits activation of latent TGF-beta 1 without inhibiting protease mediated cleavage of the LAP portion of latent TGF-beta 1.

Alternatively, rather than steps (b) and (c) above, the method for screening an anti-latent TGF-beta 1 antibody comprises, e.g., steps (b) and (c) below:
(b) measuring (i) the amount of non-cleaved latent TGF-beta 1 and (ii) the amount of mature TGF-beta 1; and
(c) selecting the test antibody that inhibits a protease mediated release of mature TGF-beta 1 from latent TGF-beta 1 without inhibiting a protease mediated cleavage of the LAP region of latent TGF-beta 1, if the amount of non-cleaved latent TGF-beta 1 is not significantly increased and the amount of mature-TGF-beta 1 is decreased as compared to when the test antibody is absent.

Alternatively, rather than steps (b) and (c) above, the method for screening an anti-latent TGF-beta 1 antibody comprises, e.g., steps (b) and (c) below:
(b) measuring (i) the amount of cleavage product of latent TGF-beta 1 and (ii) the level of mature TGF-beta 1 activity; and
(c) selecting the test antibody that inhibits a protease mediated activation of latent TGF-beta 1 without inhibiting a protease mediated cleavage of the LAP region of latent TGF-beta 1, if the amount of cleavage product is not significantly decreased and the level of mature-TGF-beta 1 activity is decreased as compared to when the test antibody is absent.

Furthermore, the present invention provides a method for producing an anti-latent TGF-beta 1 antibody, which comprises, e.g., steps (d) and (e) below in addition to steps (a) to (c) above:
(d) obtaining amino acid sequence information of the anti-latent TGF-beta 1 antibody selected in step (c); and
(e) introducing a gene encoding the anti-latent TGF-beta 1 antibody into a host cell.

In this context, the term "not significantly increased/decreased", e.g., in the phrases "the amount of non-cleaved latent TGF-beta 1 is not significantly increased" and "the amount of cleavage product (of latent TGF-beta 1) is not significantly decreased" means that the level/degree of the increase/decrease may be zero, or may not be zero but near zero, or may be very low enough to be able to be technically neglected or realistically/substantially considered to be zero by those skilled in the art. For example, in an immunoblotting analysis, when a researcher cannot detect or observe any significant signal/band (or a relatively high or strong signal) for non-cleaved latent TGF-beta 1, it is considered that the amount of non-cleaved latent TGF-beta 1 is "not significantly increased", or the amount of cleavage product (of latent TGF-beta 1) is "not significantly decreased". In addition, the term "not significantly increased/decreased" is interchangeably used with the term "not substantially increased/decreased".

In some embodiments, whether a test antibody inhibits the cleavage of the LAP region of latent TGF-beta 1, and whether a test antibody inhibits activation of latent TGF-beta 1 can be determined by various assays described herein and known in the art.

D. Immunoconjugates

The invention also provides immunoconjugates comprising an anti-latent TGF-beta 1 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., Cancer Res. 53:3336-3342 (1993); and Lode et al., Cancer Res. 58:2925-2928 (1998)); an anthracycline such as daunomycin or doxorubicin (see Kratz et al., Current Med. Chem. 13:477-523 (2006); Jeffrey et al., Bioorganic & Med. Chem. Letters 16:358-362 (2006); Torgov et al., Bioconj. Chem. 16:717-721 (2005); Nagy et al., Proc. Natl. Acad. Sci. USA 97:829-834 (2000); Dubowchik et al., Bioorg. & Med. Chem. Letters 12:1529-1532 (2002); King et al., J. Med. Chem. 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S), *Momordica charantia* inhibitor, curcin, crotin, *Saponaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $^{211}$At, $^{131}$I, $^{125}$I, $^{90}$Y, $^{186}$Re, $^{188}$Re, $^{153}$Sm, $^{212}$Bi, $^{32}$P, $^{212}$Pb and radioactive isotopes of Lu. When the radioconjugate is used for detection, it may comprise a radioactive atom for scintigraphic studies, for example Tc-99m or $^{123}$I, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionuclide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Methods and Compositions for Diagnostics and Detection

In certain embodiments, any of the anti-latent TGF-beta 1 antibodies provided herein is useful for detecting the presence of TGF-beta 1, e.g., latent TGF-beta 1 in a biological sample. The term "detecting" as used herein encompasses quantitative or qualitative detection/measurement. In certain embodiments, a biological sample comprises a cell or tissue, such as serum, whole blood, plasma, biopsy sample, tissue sample, cell suspension, saliva, sputum, oral fluid, cerebrospinal fluid, amniotic fluid, ascites fluid, milk, colostrums, mammary gland secretion, lymph, urine, sweat, lacrimal fluid, gastric fluid, synovial fluid, peritoneal fluid, ocular lens fluid and mucus.

In one embodiment, an anti-latent TGF-beta 1 antibody for use in a method of diagnosis or detection is provided. In a further aspect, a method of detecting the presence of TGF-beta 1, e.g., latent TGF-beta 1 in a biological sample is provided. For example, the method of detecting the presence of latent TGF-beta 1 comprises:

(a) contacting a biological sample with an anti-latent TGF-beta 1 antibody of the present invention described herein under conditions permissive for binding of the anti-latent TGF-beta 1 antibody to latent TGF-beta 1; and (b) detecting whether a complex is formed between the anti-latent TGF-beta 1 antibody and latent TGF-beta 1.

Such a method may be an in vitro or in vivo method. In one embodiment, an anti-latent TGF-beta 1 antibody is used to select subjects eligible for therapy with an anti-latent TGF-beta 1 antibody, e.g., where TGF-beta 1, e.g., latent TGF-beta 1 is a biomarker for selection of patients. That is, the anti-latent TGF-beta 1 antibody is useful as a diagnostic agent in targeting TGF-beta 1.

More specifically, the anti-latent TGF-beta 1 antibody is useful for the diagnosis of fibrosis, preferably myocardial fibrosis, pulmonary/lung fibrosis, liver fibrosis, renal fibrosis, skin fibrosis, ocular fibrosis and myelofibrosis. Anti-latent TGF-beta 1 antibodies of the invention are also useful for the diagnosis of cancer.

In some embodiments, the present invention provides a method of inhibiting release of mature TGF-beta 1 from latent TGF-beta 1 without inhibiting a cleavage of the LAP region of latent TGF-beta 1 mediated by protease in a biological sample, comprising contacting the biological sample containing latent TGF-beta 1 with the anti-latent TGF-beta 1 antibody of the present invention under conditions permissive for binding of the antibody to latent TGF-beta 1.

In certain embodiments, e.g., for the detection/diagnosis purposes, labeled anti-latent TGF-beta 1 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, beta-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-latent TGF-beta 1 antibody as described herein are prepared by mixing such an antibody having the desired degree of purity with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX (registered trademark), Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

In one aspect, the invention provides pharmaceutical formulations comprising an anti-latent TGF-beta 1 antibody for treatment of fibrosis, preferably myocardial fibrosis, pulmonary fibrosis, liver fibrosis, renal fibrosis, skin fibrosis, ocular fibrosis and myelofibrosis. The invention also provides pharmaceutical formulations comprising an anti-latent TGF-beta 1 antibody for treatment of cancer.

The formulation herein may also contain more than one active ingredients as necessary for the particular indication being treated, preferably those with complementary activities that do not adversely affect each other. For example, it may be desirable to further provide immune checkpoint inhibitors, which are described in "III. COMBINATION THERAPIES" below.

Active ingredients may be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-latent TGF-beta 1 antibodies provided herein may be used in therapeutic methods. In one aspect, an anti-latent TGF-beta 1 antibody for use as a medicament is provided. In further aspects, an anti-latent TGF-beta 1 antibody for use in treating cancer or fibrosis (such as liver fibrosis, renal fibrosis, or lung fibrosis), etc., is provided. In certain embodiments, an anti-latent TGF-beta 1 antibody for use in a method of treatment is provided. In certain embodiments, the invention provides an anti-latent TGF-beta 1 antibody for use in a method of treating an individual having cancer or fibrosis (such as liver fibrosis, renal fibrosis, or lung fibrosis), etc., comprising administering to the individual an effective amount of the anti-latent TGF-beta 1 antibody. In one such embodiment, the method further comprises administering to the individual an effective amount of at least one additional therapeutic agent, e.g., as described below. In further embodiments, the invention provides an anti-latent TGF-beta 1 antibody for use in inhibiting protease mediated activation of latent TGF-beta 1. In certain embodiments, the invention provides an anti-latent TGF-beta 1 antibody for use in a method of inhibiting protease mediated activation of latent TGF-beta 1 in an individual comprising administering to the individual an effective of the anti-latent TGF-beta 1 antibody to inhibit protease mediated activation of latent TGF-beta 1. An "individual" according to any of the above embodiments is preferably a human.

In a further aspect, the invention provides for the use of an anti-latent TGF-beta 1 antibody in the manufacture or preparation of a medicament. In one embodiment, the medicament is for treatment of cancer or fibrosis (such as liver fibrosis, renal fibrosis, or lung fibrosis), etc. In a further embodiment, the medicament is for use in a method of treating cancer or fibrosis (such as liver fibrosis, renal fibrosis, or lung fibrosis), etc., comprising administering to an individual having cancer or fibrosis (such as liver fibrosis, renal fibrosis, or lung fibrosis), etc., an effective amount of the medicament. In one such embodiment, the method further comprises administering to the individual an effective amount of at least one additional therapeutic agent, e.g., as described below. In a further embodiment, the medicament is for inhibiting protease mediated activation of latent TGF-beta 1. In a further embodiment, the medicament is for use in a method of inhibiting protease mediated activation of latent TGF-beta 1 in an individual comprising administering to the individual an amount effective of the medicament to inhibit protease mediated activation of latent TGF-beta 1. An "individual" according to any of the above embodiments may be a human.

In a further aspect, the invention provides a method for treating a cancer or fibrosis (such as liver fibrosis, renal fibrosis, or lung fibrosis), etc. In one embodiment, the method comprises administering to an individual having such cancer or fibrosis (such as liver fibrosis, renal fibrosis, or lung fibrosis), etc., an effective amount of an anti-latent TGF-beta 1 antibody. In one such embodiment, the method further comprises administering to the individual an effective amount of at least one additional therapeutic agent, as described below. In some embodiments, the administration of the antibody and the agent is concomitant. An "individual" according to any of the above embodiments may be a human.

In a further aspect, the invention provides a method for inhibiting protease mediated activation of latent TGF-beta 1 in an individual. In one embodiment, the method comprises administering to the individual an effective amount of an anti-latent TGF-beta 1 antibody to inhibit protease mediated activation of latent TGF-beta 1. In one embodiment, an "individual" is a human.

In a further aspect, the invention provides pharmaceutical formulations comprising any of the anti-latent TGF-beta 1 antibodies provided herein, e.g., for use in any of the above therapeutic methods. In one embodiment, a pharmaceutical formulation comprises any of the anti-latent TGF-beta 1 antibodies provided herein and a pharmaceutically acceptable carrier. In another embodiment, a pharmaceutical formulation comprises any of the anti-latent TGF-beta 1 antibodies provided herein and at least one additional therapeutic agent, e.g., as described below.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

It is understood that any of the articles of manufacture described herein may include an immunoconjugate of the invention in place of or in addition to an anti-latent TGF-beta 1 antibody.

III. Combination Therapies

Anti-latent TGF beta-1 antibodies of the invention can be used either alone or in combination with other agents in a therapy, preferably for the treatment of cancer or fibrosis, more preferably for the treatment of cancer. For instance, an antibody of the invention may be co-administered with at least one additional therapeutic agent. In some embodiments, the administration of the antibody and the agent is concomitant. In certain embodiments, an additional therapeutic agent is one or more immune checkpoint inhibitors, e.g., an inhibitor of CTLA-4, PD-1, PD-L1, PD-L2, CD160, CD57, CD244, LAG-3, CD272, KLRG1, CD26, CD39, CD73, CD305, TIGIT, TIM-3, and/or VISTA. In some embodiments, immune checkpoint inhibitors are, e.g., an anti-CTLA-4 antibody, an anti-PD-1 antibody, an anti-PD-L1 antibody, an anti-PD-L2 antibody, an anti-CD160 antibody, an anti-CD57 antibody, an anti-CD244 antibody, an anti-LAG-3 antibody, an anti-CD272 antibody, an anti-KLRG1 antibody, an anti-CD26 antibody, an anti-CD39 antibody, an anti-CD73 antibody, an anti-CD305 antibody, an anti-TIGIT antibody, an anti-TIM-3 antibody, and/or an anti-VISTA antibody. Preferably, the immune checkpoint inhibitor is a PD-1 axis binding antagonist. More preferably, the immune checkpoint inhibitor is an anti-PD-1 antibody or an anti-PD-L1 antibody. In some embodiments, the anti-PD-1 antibody is Nivolumab, Pembrolizumab, or Cemiplimab. In some embodiments, the anti-PD-L1 antibody is Atezolizumab, Avelumab, or Durvalumab, preferably Atezolizumab. Preferably, a combination therapy comprises an anti-latent TGF beta-1 antibody of the invention and Atezolizumab. In some embodiments, a combination therapy comprising an anti-latent TGF beta-1 antibody of the invention and one or more immune checkpoint inhibitors has additive or synergistic efficacy, e.g., additive, combinatorial or synergistic antitumor effect, compared to the anti-TGF beta antibody monotherapy or the immune checkpoint inhibitor monotherapy.

In one aspect, combination therapies of the invention are for treatment of cancer or fibrosis, preferably cancer. In one embodiment, cancer is resistant to immune checkpoint inhibitors and/or shows limited response to immune-checkpoint inhibitors. Without being bound by any theory, lack of response of some immune checkpoint resistant cancer and/or shows limited response to immune-checkpoint inhibitors are associated with a signature of TGF-beta signaling in fibroblasts, particularly in patients with CD8+ T cells that are excluded from the tumour parenchyma and instead found in the fibroblast- and collagen-rich peritumoural stroma. Therefore, an anti-latent TGF-beta 1 antibody in combination with immune checkpoint inhibitors can reduce TGF-beta signalling in stromal cells, promote T cell penetration into the centre of the tumour, and can exhibit enhanced anti-tumor activity.

Programmed cell death protein 1 (PD-1; also known as CD274 or B7-H1) is a type I membrane protein which belongs to the CD28/CTLA-4 family of T cell regulators. PD-1 has two ligands, i.e., PD-L1 and PD-L2 which belong to the B7 family. It is thought that PD-1 and the ligands negatively regulate immune responses such as T cell responses. PD-L1 and PD-1 are highly expressed in several types of cancers, and thought to have a role in cancer immune evasion. Inhibitors such as "(immune) checkpoint inhibitors" which inhibit, for example, the interaction between PD-1 and PD-L1 can enhance T-cell responses and increase antitumor activity.

The term "PD-1 axis binding antagonist" refers to a molecule that inhibits the interaction of a PD-1 axis binding partner with either one or more of its binding partner, so as to remove T-cell dysfunction resulting from signaling on the PD-1 signaling axis—with a result being to restore or enhance T-cell function (e.g., proliferation, cytokine production, target cell killing). As used herein, a PD-1 axis binding antagonist includes a PD-1 binding antagonist, a PD-L1 binding antagonist and a PD-L2 binding antagonist The term "PD-1 binding antagonist" refers to a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to one or more of its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In a specific aspect, a PD-1 binding antagonist is MDX-1106 (nivolumab), MK-3475 (lambrolizumab), CT-011 (pidilizumab), or AMP-224 or AMP-514 (MEDI0680). In another specific aspect, a PD-1 antagonist is selected from the group consisting of PDR001, REGN2810, BGB A317 and SHR-1210.

The term "PD-L1 binding antagonist" refers to a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. In a specific aspect, an anti-PD-L1 antibody is YW243.55.S70 (Atezolizumab), MDX-1105, avelumab, MPDL3280A, or MEDI4736 (durvalumab).

The term "PD-L2 binding antagonist" refers to a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to one or more of its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative costimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-latent TGF-beta 1 antibody and administration of an additional therapeutic agent occur within about one month, or within about one, two or three weeks, or within about one, two, three, four, five, or six days, of each other. Antibodies of the invention can also be used in combination with radiation therapy.

In one aspect, when the combination therapies noted above encompass combined administration and two or more therapeutic agents are included in the same the pharmaceutical formulation, the pharmaceutical formulation herein comprises, for example, an anti-latent TGF beta-1 antibody of the invention and one or more immune checkpoint inhibitors described above. Preferably, the pharmaceutical formulation herein comprises an anti-latent TGF beta-1 antibody of the invention, a PD-1 axis binding antagonist (preferably an anti-PD-L1 antibody, more preferably Atezolizumab) and a pharmaceutically acceptable carrier.

In one aspect, the invention provides an anti-latent TGF-beta 1 antibody for use in combination with additional therapeutic agents, for the treatment of one or more diseases. In another aspect, the invention provides a pharmaceutical formulation comprising an anti-latent TGF-beta 1 antibody for use in combination with additional therapeutic agents, for the treatment of one or more diseases. In one embodiment, the one or more diseases are cancer and/or fibrosis, preferably cancer. In one embodiment the additional therapeutic agents are one or more one or more immune checkpoint inhibitors described above. Preferably, the invention provides the anti-latent TGF-beta 1 antibody for use in combination with a PD-1 axis binding antagonist (preferably an anti-PD-L1 antibody, more preferably Atezolizumab), for the treatment of cancer.

In one aspect, the invention provides a PD-1 axis binding antagonist (preferably an anti-PD-L1 antibody, more preferably Atezolizumab) for use in combination with an anti-latent TGF-beta 1 antibody, for the treatment of one or more diseases. In another aspect, the invention provides a pharmaceutical formulation comprising a PD-1 axis binding antagonist (preferably an anti-PD-L1 antibody, more preferably Atezolizumab) for use in combination with an anti-latent TGF-beta 1 antibody, for the treatment of one or more diseases. In one embodiment, the one or more diseases are cancer and/or fibrosis, preferably cancer.

IV. Articles of Manufacture, Kits

A. Articles of Manufacture

In another aspect of the invention, an article of manufacture containing materials useful for the treatment, prevention and/or diagnosis of the disorders described above (e.g., fibrosis and cancer) is provided. The article of manufacture comprises a container and a label on or a package insert associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition (e.g., fibrosis and cancer) and may have a sterile access port (for example the container may be an intravenous solution bag or a vial having a stopper pierceable by a hypodermic injection needle). At least one active ingredient in the composition is an antibody or immunoconjugate of the invention. The label or package insert indicates that the composition is used for treating the condition of choice (e.g., fibrosis and cancer). Moreover, the article of manufacture may comprise (a) a first container with a composition contained therein, wherein the composition comprises an antibody/immunoconjugate of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition (e.g., fibrosis and cancer). Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-latent TGF-beta 1 antibody.

B. Kits

The present disclosure provides kits for use in a method for the treatment, prevention and/or diagnosis of the disorders described herein, in particular, treatment of an individual having fibrosis or cancer, which contain an anti-latent TGF-beta 1 antibody, an immunoconjugate comprising the anti-latent TGF-beta 1 antibody, an isolated nucleic acid encoding the anti-latent TGF-beta 1 antibody, or a vector comprising the nucleic acid of the present disclosure, or produced by a method of the present disclosure. The kits may additionally contain any therapeutic agents exemplified in "III. COMBINATION THERAPIES" herein, such as an immune checkpoint inhibitor including an anti-PD-L1 antibody. The kits may be packaged with an additional pharmaceutically acceptable carrier or medium disclosed herein, or instruction manual describing how to use the kits, etc. As with the article of manufacture described herein, the kit may contain materials useful for the treatment of fibrosis or cancer; a container and a label on or a package insert associated with the container; a composition which is by itself or combined with another composition effective for treating fibrosis or cancer; a sterile access port, etc. The kits may further comprise a label or package insert indicating that the compositions can be used to treat fibrosis or cancer. Alternatively, or additionally, the kits may further comprise a second (or third) container comprising a pharmaceutically-acceptable buffer, such as bacteriostatic water for injection (BWFI), phosphate-buffered saline, Ringer's solution and dextrose solution. The kits may further include other materials desirable from a commercial and user standpoint, including other buffers, diluents, filters, needles, and syringes.

EXAMPLES

The following are examples of methods and compositions of the invention. It is understood that various other embodiments may be practiced, given the general description provided above.

Example 1: Expression and Purification of Antigens (1-1) Expression and Purification of Latent TGF-Beta 1

The sequences used for expression and purification were: flag-tagged human latent TGF-beta 1 (SEQ ID NO: 1, 2) and flag-tagged mouse latent TGF-beta 1 (SEQ ID NO: 3, 4), and flag-tagged cynomolgus monkey latent TGF-beta 1 (SEQ ID NO: 5, 6). Each of these flag-tagged latent TGF-beta 1 has, from its N-terminus to C-terminus, a signal sequence derived from rat serum albumin (SEQ ID NO: 7), a Flag-tag, and a sequence of latent TGF-beta 1. The Cys residue at the thirtieth (30th) position in each of these flag-tagged latent TGF-beta 1 was substituted with Ser, which corresponds to 'C33S mutation' (see, e.g., Yoshinaga K, et al. Perturbation of transforming growth factor (TGF)-beta1 association with latent TGF-beta binding protein yields inflammation and tumors. Proc Natl Acad Sci USA. 2008; 105(48):18758-18763).

Flag-tagged human latent TGF-beta 1 (hereinafter called "human latent TGF-beta 1 (SLC)" or "human latent TGF-beta 1"), flag-tagged mouse latent TGF-beta 1 (hereinafter called "mouse latent TGF-beta 1 (SLC)" or "mouse latent TGF-beta 1"), or flag-tagged cynomolgus monkey latent TGF-beta 1 (hereinafter called "monkey latent TGF-beta 1 (SLC)" or "monkey latent TGF-beta 1") was expressed transiently using FreeStyle293-F or Expi293F cell line (Thermo Fisher Schientific). Conditioned media expressing human, mouse or monkey latent TGF-beta 1 (SLC) was applied to a column packed with anti-Flag M2 affinity resin (Sigma), and latent TGF-beta 1 (SLC) was eluted with a Flag peptide (Sigma). Fractions containing human, mouse or monkey latent TGF-beta 1 (SLC) were collected and subsequently subjected to a Superdex 200 gel filtration column (GE healthcare) equilibrated with 1×PBS. Fractions containing human, mouse or monkey latent TGF-beta 1 (SLC) were then pooled and stored at −80 degrees C.

(1-2) Expression and Purification of Mouse Latency Associated Peptide (LAP)

The sequence used for expression and purification was: flag-tagged mouse LAP (SEQ ID NO: 8, 9), which has, from its N-terminus to C terminus, a signal sequence derived from rat serum albumin (SEQ ID NO: 7), a Flag-tag, and a sequence of latency associated protein (LAP). The Cys residue at the thirtieth (30th) position in flag-tagged LAP was substituted with Ser, which corresponds to 'C33S mutation'. Expression and purification of Flag-tagged mouse LAP (SEQ ID NO: 8, 9) (hereinafter called "recombinant mouse latency associated protein (LAP)") were performed exactly the same way as described in EXAMPLE (1-1).

Example 2. Humanization and Optimization of Anti-TGF-Beta 1 Antibody (2-1) Humanization A parent anti-TGF-beta antibody TBA0947, chimeric antibody, was humanized as follows. First, variable regions of the heavy and light chains of humanized antibodies were designed using variable regions of TBA0947 and human germline frameworks. Then, the polynucleotides of each designed heavy variable region and light chain variable region were cloned into expression vectors containing the heavy chain constant region SG181 sequence (SEQ ID NO: 10) and the light chain constant region SK1 sequence (SEQ ID NO: 11), respectively. Humanized antibodies were transiently expressed in FreeStyle 293-F Cells (Thermo Fisher Scientific), and Biacore analysis was carried out. A humanized antibody that showed at least similar Biacore binding activity as the parent antibody was selected.

(2-2) Optimization

The humanized antibody obtained in Example (2-1) was optimized to hT0947AE04, hT0947AE07, hT0947AE08, and hT0947AE09 with improved binding activity towards latent TGF-beta 1 (SLC). Briefly, comprehensive mutagenesis was performed for all residues in the complementarity-determining regions (CDRs) of both heavy and light chain. Each amino acid was substituted with 18 other naturally occurring amino acids, excluding the original amino acid and cysteine. The variants were transiently expressed in FreeStyle 293-F Cells (Thermo Fisher Scientific), and purified from culture supernatants for assessment by Biacore. Variants of interest with improved binding activity to both human and murine latent TGF-beta 1 (SLC) were selected. Antibodies with a combination of these mutations in the CDRs were then generated.

(2-3) Amino Acid Sequence of Optimized Antibody

The amino acid sequences of the variable regions of hT0947AE04, hT0947AE07, hT0947AE08, and hT0947AE09 were identified as follows:

The heavy chain variable region of hT0947AE04 comprises an amino acid sequence of SEQ ID NO: 12 (hT0947AE04H), and the light chain variable region of hT0947AE04 comprises an amino acid sequence of SEQ ID NO: 13 (hT0947AE04L).

The heavy chain variable region of hT0947AE07 comprises an amino acid sequence of SEQ ID NO: 14 (hT0947AE07H), and the light chain variable region of hT0947AE07 comprises an amino acid sequence of SEQ ID NO: 15 (hT0947AE07L).

The heavy chain variable region of hT0947AE08 comprises an amino acid sequence of SEQ ID NO: 16 (hT0947AE08H) and the light chain variable region of hT0947AE08 comprises an amino acid sequence of SEQ ID NO: 17 (hT0947AE08L).

The heavy chain variable region of hT0947AE09 comprises an amino acid sequence of SEQ ID NO: 18 (hT0947AE09H), and the light chain variable region of hT0947AE09 comprises an amino acid sequence of SEQ ID NO: 19 (hT0947AE09L).

The amino acid sequences of the CDRs (HVRs) of hT0947AE04, hT0947AE07, hT0947AE08, and hT0947AE09 were identified as follows according to Kabat:

hT0947AE04 comprises the heavy chain CDR1, CDR2 and CDR3 which comprise amino acid sequences of SEQ ID NOs: 20, 21 and 22, respectively, and the light chain CDR1, CDR2 and CDR3 which comprise amino acid sequences of SEQ ID NOs: 23, 24 and 25, respectively.

hT0947AE07 comprises the heavy chain CDR1, CDR2 and CDR3 which comprise amino acid sequences of SEQ ID NOs: 26, 27 and 28, respectively, and the light chain CDR1, CDR2 and CDR3 which comprise amino acid sequences of SEQ ID NOs: 29, 30 and 31, respectively.

hT0947AE08 comprises the heavy chain CDR1, CDR2 and CDR3 which comprise amino acid sequences of SEQ ID NOs: 32, 33 and 34, respectively, and the light chain CDR1, CDR2 and CDR3 which comprise amino acid sequences of SEQ ID NOs: 35, 36 and 37, respectively.

hT0947AE09 comprises the heavy chain CDR1, CDR2 and CDR3 which comprise amino acid sequences of SEQ ID NOs: 38, 39 and 40, respectively, and the light chain CDR1, CDR2 and CDR3 which comprise amino acid sequences of SEQ ID NOs: 41, 42 and 43, respectively.

(2-4) Creation of the Full-Length Heavy and Light Chain

Multiple amino acid substitutions were introduced to a heavy chain constant region SG1 (SEQ ID NO: 44). SG1 is a wild-type human IgG1 heavy chain constant region with the deletion of the last two C-terminal amino acids, Gly-Lys (GK). As a result, SG181 (SEQ ID NO: 10) and SG191 (SEQ ID NO: 45) were generated. SG181 includes amino acid substitutions L235R/G236R (amino acid substitutions to reduce effector function), and K214R, according to the EU index. SG191 includes amino acid substitutions L235R/G236R (amino acid substitutions to reduce effector function), M428L/N434A (amino acid substitutions to enhance binding activity to FcRn), Q438R/S440E (amino acid substitutions to reduce binding to rheumatoid factor), and K214R, according to the EU index. Further, mF18 (SEQ ID NO: 46), a mouse IgG heavy chain constant region which includes P235K/S239K (amino acid substitutions to reduce effector function), was generated.

Each of the heavy chain variable regions was combined with a heavy chain constant region SG181 (SEQ ID NO: 10), SG191 (SEQ ID NO: 45), or mF18 (SEQ ID NO: 46). Thus, the full-length heavy chain sequences having the following amino acid sequences were created:

(a1) The full-length heavy chain comprising an amino acid sequence of SEQ ID NO: 47, which comprises hT0947AE04H (heavy chain variable region) and SG181 (heavy chain constant region)

(a2) The full-length heavy chain comprising an amino acid sequence of SEQ ID NO: 48, which comprises hT0947AE07H (heavy chain variable region) and SG181 (heavy chain constant region)

(a3) The full-length heavy chain comprising an amino acid sequence of SEQ ID NO: 49, which comprises hT0947AE08H (heavy chain variable region) and SG181 (heavy chain constant region)

(a4) The full-length heavy chain comprising an amino acid sequence of SEQ ID NO: 50, which comprises hT0947AE09H (heavy chain variable region) and SG181 (heavy chain constant region)

(b1) The full-length heavy chain comprising an amino acid sequence of SEQ ID NO: 51, which comprises hT0947AE04H (heavy chain variable region) and SG191 (heavy chain constant region)

(b2) The full-length heavy chain comprising an amino acid sequence of SEQ ID NO: 52, which comprises hT0947AE07H (heavy chain variable region) and SG191 (heavy chain constant region)

(b3) The full-length heavy chain comprising an amino acid sequence of SEQ ID NO: 53, which comprises hT0947AE08H (heavy chain variable region) and SG191 (heavy chain constant region)

(b4) The full-length heavy chain comprising an amino acid sequence of SEQ ID NO: 54, which comprises hT0947AE09H (heavy chain variable region) and SG191 (heavy chain constant region)

(c1) The full-length heavy chain comprising an amino acid sequence of SEQ ID NO: 55, which comprises hT0947AE04H (heavy chain variable region) and mF18 (heavy chain constant region)
(c2) The full-length heavy chain comprising an amino acid sequence of SEQ ID NO: 56, which comprises hT0947AE07H (heavy chain variable region) and mF18 (heavy chain constant region)
(c3) The full-length heavy chain comprising an amino acid sequence of SEQ ID NO: 57, which comprises hT0947AE08H (heavy chain variable region) and mF18 (heavy chain constant region)
(c4) The full-length heavy chain comprising an amino acid sequence of SEQ ID NO: 58, which comprises hT0947AE09H (heavy chain variable region) and mF18 (heavy chain constant region)

Each of the light chain variable regions was combined with a human IgG light chain constant region (kappa) SK1 (SEQ ID NO: 11), or a mouse IgG light chain constant region (kappa) mk1 (SEQ ID NO: 59). Thus, the full-length light chain sequences having the following amino acid sequences were created:
(d1) The full-length light chain comprising an amino acid sequence of SEQ ID NO: 60, which comprises hT0947AE04L (light chain variable region) and SK1 (light chain constant region)
(d2) The full-length light chain comprising an amino acid sequence of SEQ ID NO: 61, which comprises hT0947AE07L (light chain variable region) and SK1 (light chain constant region)
(d3) The full-length light chain comprising an amino acid sequence of SEQ ID NO: 62, which comprises hT0947AE08L (light chain variable region) and SK1 (light chain constant region)
(d4) The full-length light chain comprising an amino acid sequence of SEQ ID NO: 63, which comprises hT0947AE09L (light chain variable region) and SK1 (light chain constant region)
(e1) The full-length light chain comprising an amino acid sequence of SEQ ID NO: 64, which comprises hT0947AE04L (light chain variable region) and mk1 (light chain constant region)
(e2) The full-length light chain comprising an amino acid sequence of SEQ ID NO: 65, which comprises hT0947AE07L (light chain variable region) and mk1 (light chain constant region)
(e3) The full-length light chain comprising an amino acid sequence of SEQ ID NO: 66, which comprises hT0947AE08L (light chain variable region) and mk1 (light chain constant region)
(e4) The full-length light chain comprising an amino acid sequence of SEQ ID NO: 67, which comprises hT0947AE09L (light chain variable region) and mk1 (light chain constant region)

Then, the respective full-length heavy chains and light chains were combined, and the antibodies shown in Table 2 were created. The antibodies created were named as shown in Table 2, and are referred to as their respective names in the present description.

TABLE 2

| Antibody name | Heavy chain | Light chain |
| --- | --- | --- |
| hT0947AE04-SG181 | SEQ ID NO: 47 (hT0947AE04H and SG181) | SEQ ID NO: 60 (hT0947AE04L and SK1) |
| hT0947AE07-SG181 | SEQ ID NO: 48 (hT0947AE07H and SG181) | SEQ ID NO: 61 (hT0947AE07L and SK1) |
| hT0947AE08-SG181 | SEQ ID NO: 49 (hT0947AE08H and SG181) | SEQ ID NO: 62 (hT0947AE08L and SK1) |
| hT0947AE09-SG181 | SEQ ID NO: 50 (hT0947AE09H and SG181) | SEQ ID NO: 63 (hT0947AE09L and SK1) |
| hT0947AE04-SG191 | SEQ ID NO: 51 (hT0947AE04H and SG191) | SEQ ID NO: 60 (hT0947AE04L and SK1) |
| hT0947AE07-SG191 | SEQ ID NO: 52 (hT0947AE07H and SG191) | SEQ ID NO: 61 (hT0947AE07L and SK1) |
| hT0947AE08-SG191 | SEQ ID NO: 53 (hT0947AE08H and SG191) | SEQ ID NO: 62 (hT0947AE08L and SK1) |
| hT0947AE09-SG191 | SEQ ID NO: 54 (hT0947AE09H and SG191) | SEQ ID NO: 63 (hT0947AE09L and SK1) |
| hT0947AE04-mF18 | SEQ ID NO: 55 (hT0947AE04H and mF18) | SEQ ID NO: 64 (hT0947AE04L and mk1) |
| hT0947AE07-mF18 | SEQ ID NO: 56 (hT0947AE07H and mF18) | SEQ ID NO: 65 (hT0947AE07L and mk1) |
| hT0947AE08-mF18 | SEQ ID NO: 57 (hT0947AE08H and mF18) | SEQ ID NO: 66 (hT0947AE08L and mk1) |
| hT0947AE09-mF18 | SEQ ID NO: 58 (hT0947AE09H and mF18) | SEQ ID NO: 67 (hT0947AE09L and mk1) |

Example 3. BIACORE™ Analysis for Binding Activity Evaluation of Anti-Latent TGF-Beta 1 Antibodies Binding activities of anti-latent TGF-beta 1 antibodies (hT0947AE04-SG191, hT0947AE07-SG191, hT0947AE08-SG191, and hT0947AE09-SG191) towards latent TGF-beta 1 (SLC) of human, cynomolgus monkey, or mouse were measured using Biacore 8k instrument (GE Healthcare). Mouse anti-human Ig kappa light chain antibody (BD Pharmingen) was immobilized onto all flow cells of a CM5 sensor chip using amine coupling kit (GE Healthcare). Antibodies were captured onto the anti-kappa sensor surfaces at a capture level around 20RU (resonance unit), then latent TGF-beta 1 (SLC) of human, cynomolgus monkey, or mouse, which was prepared in Example (1-1), was injected over the flow cell. All antibodies and analytes were prepared in ACES pH 7.4 containing 20 mM ACES, 150 mM NaCl, 0.05% Tween 20, 0.005% NaN$_3$. Assay temperature was set at 37 degrees C. Sensor surface was regenerated each cycle with 10 mM Glycine-HCl, pH2.1. Binding activity was determined by processing and fitting the data to 1:1 binding model using Biacore Insight Software, version 1.1.1.7442 (GE Healthcare).

Binding activities (ka, kd and KD) of anti-latent TGF-beta 1 antibodies towards latent TGF-beta 1 of human, cynomolgus monkey, or mouse are shown in Table 3.

TABLE 3

| Antibody name | Human latent TGF-beta 1 | | | Cyno latent TGF-beta 1 | | | Mouse latent TGF-beta 1 | | |
|---|---|---|---|---|---|---|---|---|---|
| | ka ($M^{-1}s^{-1}$) | kd ($s^{-1}$) | KD (M) | ka ($M^{-1}s^{-1}$) | kd ($s^{-1}$) | KD (M) | ka ($M^{-1}s^{-1}$) | kd ($s^{-1}$) | KD (M) |
| hT0947AE04-SG191 | 1.83E+05 | 6.76E-04 | 3.69E-09 | 1.64E+05 | 5.80E-04 | 3.54E-09 | 1.43E+05 | 2.71E-04 | 1.89E-09 |
| hT0947AE07-SG191 | 3.58E+05 | 5.74E-04 | 1.60E-09 | 3.21E+05 | 4.90E-04 | 1.53E-09 | 3.22E+05 | 4.31E-04 | 1.34E-09 |
| hT0947AE08-SG191 | 3.81E+05 | 4.30E-04 | 1.13E-09 | 3.25E+05 | 3.26E-04 | 1.00E-09 | 2.92E+05 | 3.19E-04 | 1.10E-09 |
| hT0947AE09-SG191 | 3.39E+05 | 7.27E-04 | 2.15E-09 | 2.94E+05 | 6.59E-04 | 2.24E-09 | 2.43E+05 | 3.88E-04 | 1.60E-09 |

Example 4. Characterization of Anti-Latent TGF-Beta 1 Antibody (4-1) Anti-Latent TGF-Beta 1 Antibody Bound to Cell Surface Latent TGF-Beta 1

Figure 1B:
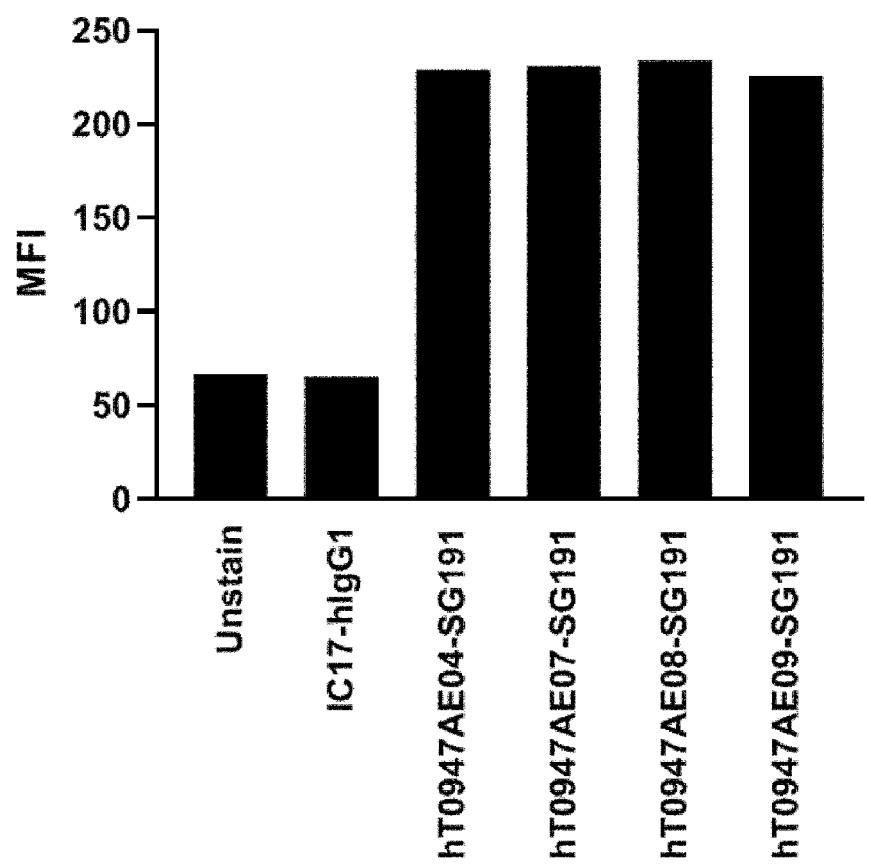
FIG. 1B shows the results of antibody binding to cell surface latent TGF-beta 1 on FreeStyle™ 293-F cells. IC17-hIgG1 represents an anti-KLH antibody as a negative control. hT0947AE04-SG191, hT0947AE07-SG191, hT0947AE08-SG191, and hT0947AE09-SG191 represent anti-latent TGF-beta 1 antibodies.

Binding activities of anti-latent TGF-beta 1 antibodies (hT0947AE04-SG191, hT0947AE07-SG191, hT0947AE08-SG191, or hT0947AE09-SG191) to cell surface latent TGF-beta 1 were tested by FACS using Ba/F3 cells expressing mouse latent TGF-beta 1 or FreeStyle™ 293-F cells expressing human latent TGF-beta 1 (ThermoFisher). The anti-latent TGF-beta 1 antibodies (10 microgram/mL each) were incubated with each cell line for 30 minutes at 4 degree C. and washed with FACS buffer (2% FBS, 2 mM EDTA in PBS). Anti-KLH antibody having human IgG1 Fc region (IC17-hIgG1), which does not bind to mouse latent TGF-beta 1 nor human latent TGF-beta 1, was used as a negative control antibody. Goat F(ab')2 anti-Human IgG, Mouse ads-PE (Southern Biotech, Cat. 2043-09) was then added and incubated for 30 minutes at 4 degree C. and washed with FACS buffer. Data acquisition was performed on an FACS Verse (Becton Dickinson), followed by analysis and calculation of Mean Fluorescence intensity (MFI), using FlowJo software (Tree Star) and GraphPad Prism software (GraphPad). As shown in FIG. 1, all anti-latent TGF-beta 1 antibodies bound to mouse cell surface latent TGF-beta 1 expressed on Ba/F3 cells and human cell surface latent TGF-beta 1 expressed on FreeStyle™ 293-F cells.

Figure 2A:
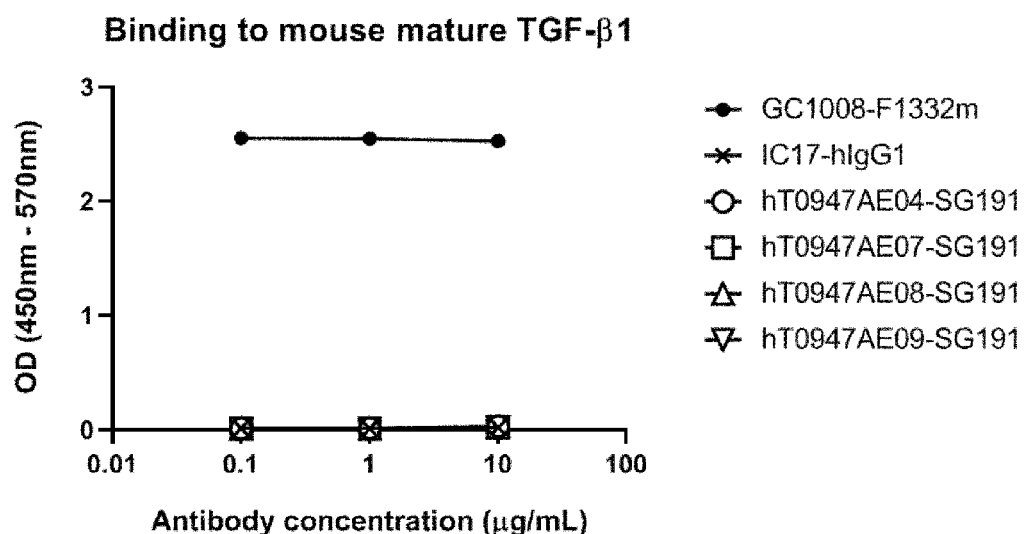
FIG. 2A shows the results of antibody binding to mouse mature TGF-beta 1. GC1008-F1332m represents an anti-mature TGF-beta antibody as a positive control. IC17-hIgG1 represents an anti-KLH antibody as a negative control. hT0947AE04-SG191, hT0947AE07-SG191, hT0947AE08-SG191, and hT0947AE09-SG191 represent anti-latent TGF-beta 1 antibodies.
Figure 2B:
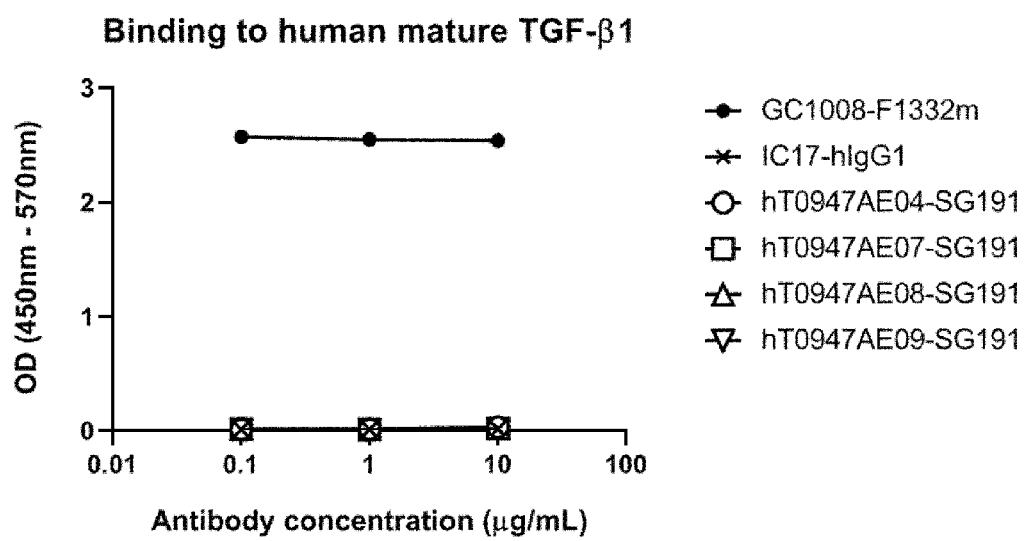
FIG. 2B shows the results of antibody binding to human mature TGF-beta 1. GC1008-F1332m represents an anti-mature TGF-beta antibody as a positive control. IC17-hIgG1 represents an anti-KLH antibody as a negative control. hT0947AE04-SG191, hT0947AE07-SG191, hT0947AE08-SG191, and hT0947AE09-SG191 represent anti-latent TGF-beta 1 antibodies.

(4-2) Anti-Latent TGF-Beta 1 Antibody Did not Bind to Mature TGF-Beta 1 but Bound to Mouse LAP Binding activities of anti-latent TGF-beta 1 antibodies (hT0947AE04-SG191, hT0947AE07-SG191, hT0947AE08-SG191, or hT0947AE09-SG191) to mature TGF-beta 1 were tested by ELISA. 384-well plate was coated with mouse or human mature TGF-beta 1 for overnight at 4 degree C., and then washed four times with PBS-T. After washing, the plate was blocked with blocking buffer (1×TBS/Tween-20+0.5% BSA+1× Block ace) for at least 1 hour at room temperature, and then washed four times with PBS-T. After washing, an antibody solution was added to the plate and incubated for 2 hours at room temperature, and then washed four times with PBS-T. After washing, diluted secondary antibody (goat anti-human IgG-HRP, Abcam, Cat. ab98624) was added to the plate and incubated for 1 hour at room temperature, and then washed four times with PBS-T. After washing, TMB solution was added to the plate and incubated for 15 minutes at room temperature, then 1N sulfuric acid was added to stop the reaction. The absorbance (optical density; OD) was measured at 450 nm/570 nm. Anti-KLH antibody (IC17-IgG1) was used as a negative control antibody, and anti-mature TGF-beta antibody GC1008 (as described in U.S. Pat. No. 8,383,780) having human IgG1 Fc region (GC1008-F1332m) was used as a positive control antibody. As shown in FIGS. 2A and 2B, anti-latent TGF-beta 1 antibodies did not bind to mouse mature TGF-beta 1 nor human mature TGF-beta 1.

Figure 2C:
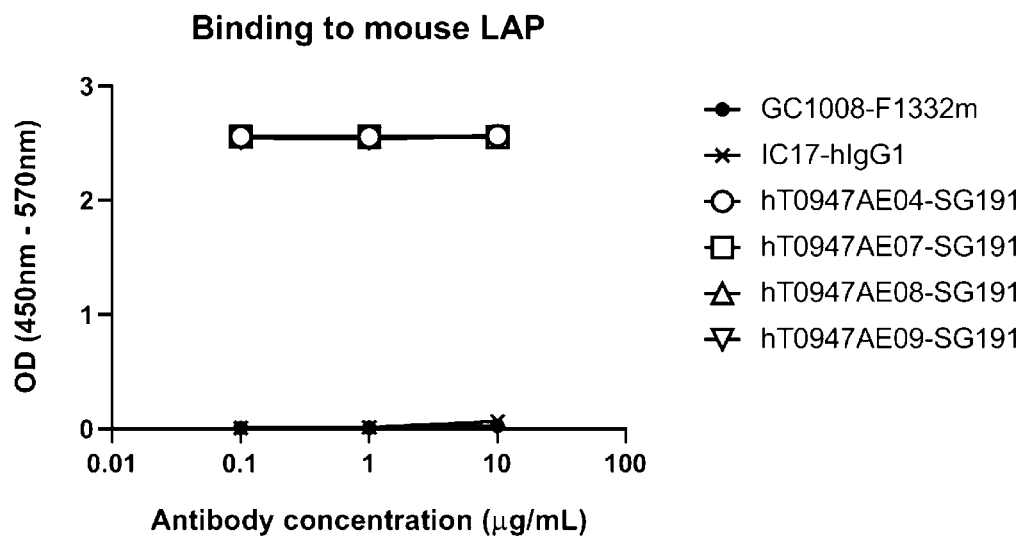
FIG. 2C shows the result of antibody binding to mouse LAP. GC1008-F1332m represents an anti-mature TGF-beta antibody. IC17-hIgG1 represents an anti-KLH antibody as a negative control. hT0947AE04-SG191, hT0947AE07-SG191, hT0947AE08-SG191, and hT0947AE09-SG191 represent anti-latent TGF-beta 1 antibodies.

Further, binding activities of anti-latent TGF-beta 1 antibodies (hT0947AE04-SG191, hT0947AE07-SG191, hT0947AE08-SG191, or hT0947A09-SG191) to mouse latency associated protein (LAP) were tested by ELISA as described above. As shown in FIG. 2C, anti-latent TGF-beta 1 antibodies bound to mouse LAP.

(4-3) Anti-Latent TGF-Beta 1 Antibody Inhibited Spontaneous Latent TGF-Beta 1 Activation Mouse latent TGF-beta 1 (mSLC) and human latent TGF-beta 1 (hSLC), which were prepared in Example (1-1), were each incubated with or without the presence of anti-latent TGF-beta 1 antibody (hT0947AE04-SG191, hT0947AE07-SG191, hT0947AE08-SG191, or hT0947AE09-SG191) at 37 degree C. for 1 hour. The anti-KLH antibody (IC17-IgG1) was used as a negative control. Spontaneous latent TGF-beta 1 activation and antibody mediated inhibition of the spontaneous latent TGF-beta 1 activation were analyzed by mature TGF-beta 1 ELISA (Human TGF-beta 1 Quantikine ELISA Kit, R&D systems) according to manufacturer's procedure.

Figure 3A:
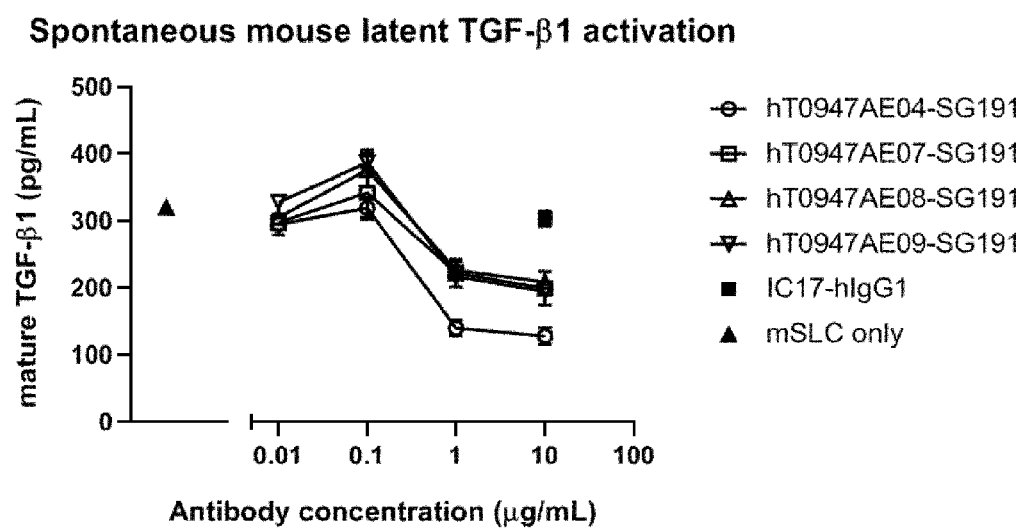
FIG. 3A shows the results of antibody activity against spontaneous mouse latent TGF-beta 1 activation. mSLC represents recombinant mouse latent TGF-beta 1. IC17-hIgG1 represents an anti-KLH antibody as a negative control. hT0947AE04-SG191, hT0947AE07-SG191, hT0947AE08-SG191, and hT0947AE09-SG191 represent anti-latent TGF-beta 1 antibodies.
Figure 3B:
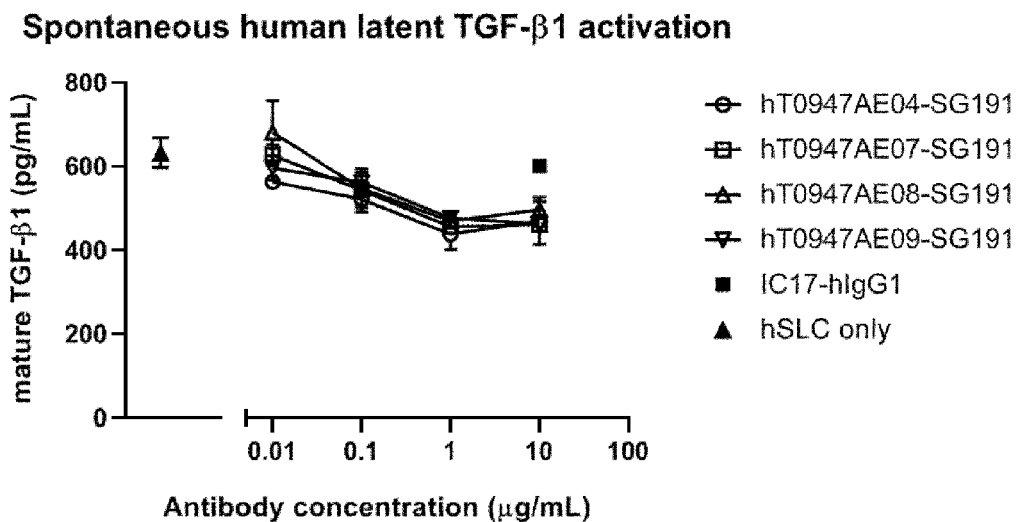
FIG. 3B shows the results of antibody activity against spontaneous human latent TGF-beta 1 activation. hSLC represents recombinant human latent TGF-beta 1. IC17-hIgG1 represents an anti-KLH antibody as a negative control. hT0947AE04-SG191, hT0947AE07-SG191, hT0947AE08-SG191, and hT0947AE09-SG191 represent anti-latent TGF-beta 1 antibodies.

As shown in FIG. 3, spontaneous activation of latent TGF-beta 1 was suppressed by anti-latent TGF-beta 1 antibodies.

Figure 4A:
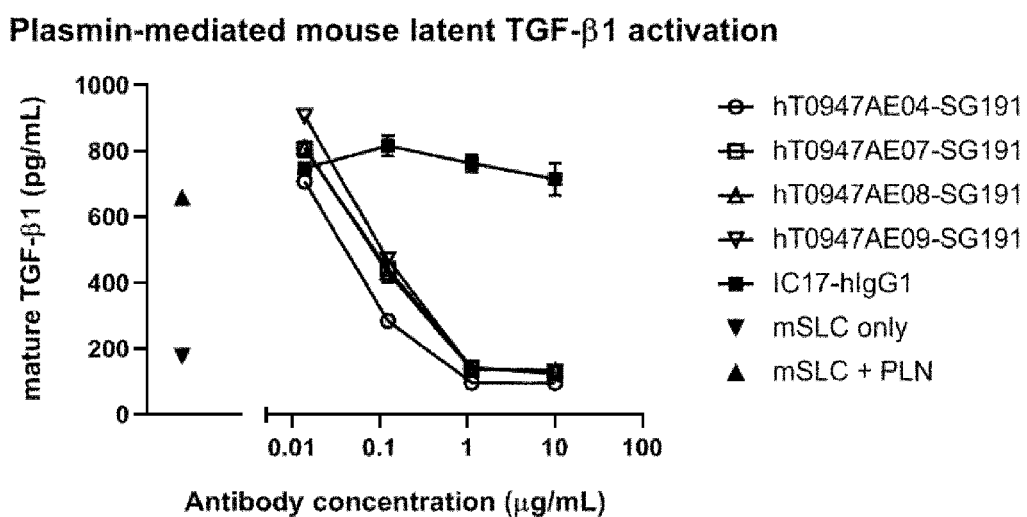
FIG. 4A shows the results of antibody activity against plasmin (PLN)-mediated mouse latent TGF-beta 1 activation. mSLC represents recombinant mouse latent TGF-beta 1. IC17-hIgG1 represents an anti-KLH antibody as a negative control. hT0947AE04-SG191, hT0947AE07-SG191, hT0947AE08-SG191, and hT0947AE09-SG191 represent anti-latent TGF-beta 1 antibodies.
Figure 4B:
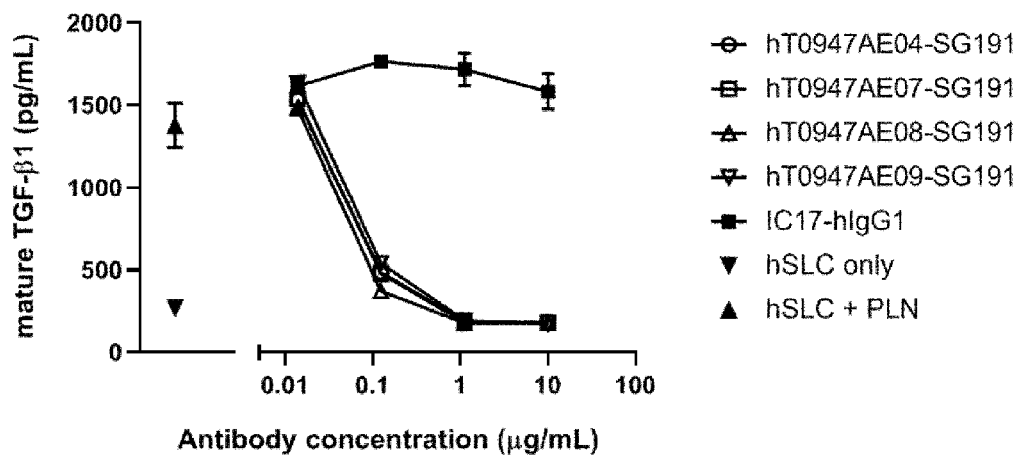
FIG. 4B shows the results of antibody activity against plasmin (PLN)-mediated human latent TGF-beta 1 activation. hSLC represents recombinant human latent TGF-beta 1. IC17-hIgG1 represents an anti-KLH antibody as a negative control. hT0947AE04-SG191, hT0947AE07-SG191, hT0947AE08-SG191, and hT0947AE09-SG191 represent anti-latent TGF-beta 1 antibodies.

(4-4) Anti-Latent TGF-Beta 1 Antibody Inhibited Plasmin (PLN)-Mediated Latent TGF-Beta 1 Activation Mouse latent TGF-beta 1 (mSLC) and human latent TGF-beta 1 (hSLC), which were prepared in Example (1-1), were each incubated with human plasmin (Calbiochem), with or without the presence of anti-latent TGF-beta 1 antibodies (hT0947AE04-SG191, hT0947AE07-SG191, hT0947AE08-SG191, or hT0947AE09-SG191) at 37 degree C. for 1 hour. Antibodies were pre-incubated with mouse or human latent TGF-beta 1 (SLC) for 30 minutes at room temperature before incubating with plasmin. Anti-KLH antibody (IC17-hIgG1) was used as a negative control. Plasmin-mediated latent TGF-beta 1 activation and antibody mediated inhibition were analyzed by mature TGF-beta 1 ELISA (Human TGF-beta 1 Quantikine ELISA Kit, R&D systems) according to manufacturer's procedure. As shown in FIG. 4, plasmin-mediated latent TGF-beta 1 activation was suppressed by anti-latent TGF-beta 1 antibodies.

Figure 5A:
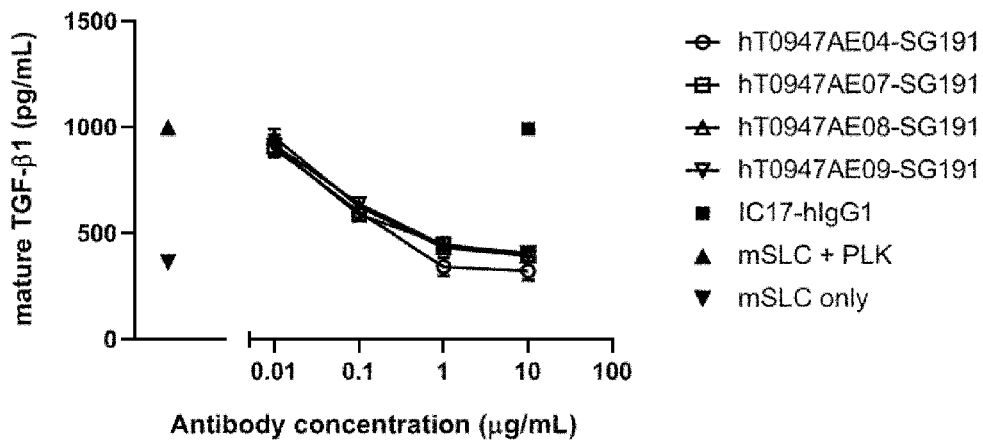
FIG. 5A shows the results of antibody activity against kallikrein (PLK)-mediated mouse latent TGF-beta 1 activation. mSLC represents recombinant mouse latent TGF-beta 1. IC17-hIgG1 represents an anti-KLH antibody as a negative control. hT0947AE04-SG191, hT0947AE07-SG191, hT0947AE08-SG191, and hT0947AE09-SG191 represent anti-latent TGF-beta 1 antibodies.
Figure 5B:
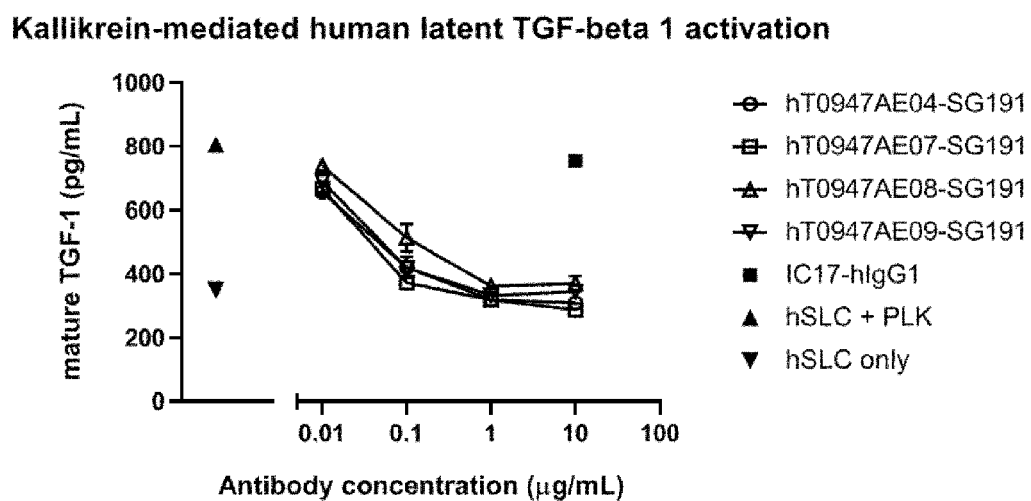
FIG. 5B shows the results of antibody activity against kallikrein (PLK)-mediated human latent TGF-beta 1 activation. hSLC represents recombinant human latent TGF-beta 1. IC17-hIgG1 represents an anti-KLH antibody as a negative control. hT0947AE04-SG191, hT0947AE07-SG191, hT0947AE08-SG191, and hT0947AE09-SG191 represent anti-latent TGF-beta 1 antibodies.

(4-5) Anti-Latent TGF-Beta 1 Antibody Inhibited Plasma Kallikrein (PLK)-Mediated Latent TGF-Beta 1 Activation Mouse latent TGF-beta 1 (mSLC) and human latent TGF-beta 1 (hSLC), which were prepared in Example (1-1), were each incubated with human kallikrein (Enzyme Research Laboratories), with or without the presence of anti-latent TGF-beta 1 antibodies (hT0947AE04-SG191, hT0947AE07-SG191, hT0947AE08-SG191, or hT0947AE09-SG191) at 37 degree C. for 2 hours. Antibodies were pre-incubated with mouse or human latent TGF-beta 1 (SLC) for 30 minutes at room temperature before incubating with kallicrein. Anti-KLH antibody (IC17-hIgG1) was used as a negative control. Kallikrein-mediated latent TGF-beta 1 activation and antibody mediated inhibition was analyzed by mature TGF-beta 1 ELISA (Human TGF-beta 1 Quantikine ELISA Kit, R&D systems) according to manufacturer's procedure. As shown in FIG. 5, kallikrein-mediated latent TGF-beta 1 activation was suppressed by anti-latent TGF-beta 1 antibodies.

Figure 6A:
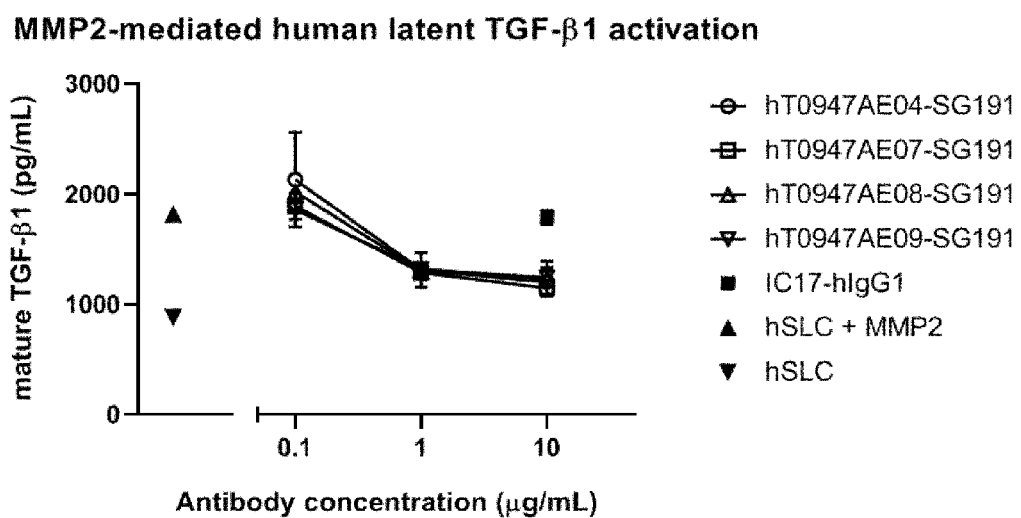
FIG. 6A shows the results of antibody activity against matrix metalloproteinase (MMP) 2-mediated human latent TGF-beta 1 activation. hSLC represents recombinant human latent TGF-beta 1. IC17-hIgG1 represents an anti-KLH antibody as a negative control. hT0947AE04-SG191, hT0947AE07-SG191, hT0947AE08-SG191, and hT0947AE09-SG191 represent anti-latent TGF-beta 1 antibodies.
Figure 6B:
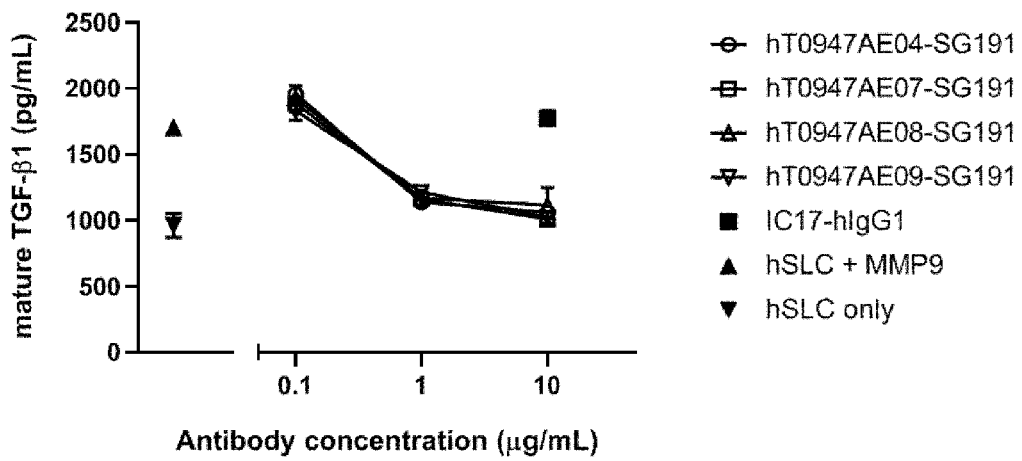
FIG. 6B shows the results of antibody activity against matrix metalloproteinase (MMP) 9-mediated human latent TGF-beta 1 activation. hSLC represents recombinant human latent TGF-beta 1. IC17-hIgG1 represents an anti-KLH antibody as a negative control. hT0947AE04-SG191, hT0947AE07-SG191, hT0947AE08-SG191, and hT0947AE09-SG191 represent anti-latent TGF-beta 1 antibodies.

(4-6) Anti-Latent TGF-Beta 1 Antibody Inhibited MMP2 and MMP9-Mediated Human Latent TGF-Beta 1 Activation Human latent TGF-beta 1 (SLC), which were prepared in Example (1-1), was incubated with activated metalloproteinase 2 (MMP2) or MMP9 (R&D systems), with or without the presence of anti-latent TGF-beta 1 antibodies (hT0947AE04-SG191, hT0947AE07-SG191, hT0947AE08-SG191, or hT0947AE09-SG191) at 37 degree C. for 2 hours. Antibodies were pre-incubated with human latent TGF-beta 1 (SLC) for 30 minutes at room temperature before incubating with MMP2 or MMP9. Anti-KLH antibody (IC17-hIgG1) was used as a negative control. MMP2 and MMP9-mediated human latent TGF-beta 1 activation and antibody mediated inhibition was analyzed by mature TGF-beta 1 ELISA (Human TGF-beta 1 Quantikine ELISA Kit, R&D systems) according to the manufacturer's procedure. As shown in FIG. 6, both MMP2-mediated human latent TGF-beta 1 activation and MMP9-mediated human latent TGF-beta 1 activation were suppressed by anti-latent TGF-beta 1 antibodies.

(4-7) Anti-Latent TGF-Beta 1 Antibody Inhibited Latent TGF-Beta 1 Activation without Preventing Latent TGF-Beta 1 Propeptide Cleavage Via Plasmin (PLN)

Mouse latent TGF-beta 1 (mSLC) and human latent TGF-beta 1 (hSLC), which were prepared in Example (1-1), were each incubated with human plasmin (Calbiochem), with or without the presence of anti-latent TGF-beta 1 antibodies (hT0947AE04-SG191, hT0947AE07-SG191, hT0947AE08-SG191, or hT0947AE09-SG191) at 37 degree C. for 1 hour. Antibodies were pre-incubated with mouse or human latent TGF-beta 1 (SLC) for 30 minutes at room temperature before incubating with plasmin. Camostat mesylate (TOCRIS), which is one of serine protease inhibitor and known to inhibit the activity of plasmin, was used as a control. The samples were mixed with 4×SDS-PAGE sample buffer (Wako), then heated at 95 degrees C. for 5 minutes, and then loaded for SDS gel electrophoresis. Proteins were transferred to membrane by Trans-Blot (registered trademark) Turbo™ Transfer System (Bio-rad). Latent TGF-beta 1 propeptide was detected using mouse anti-FLAG, M2-HRP antibody (Sigma-Aldrich). The membrane was incubated with ECL substrate, and image was taken by ImageQuant LAS 4000 (GE Healthcare).

Figure 7A:
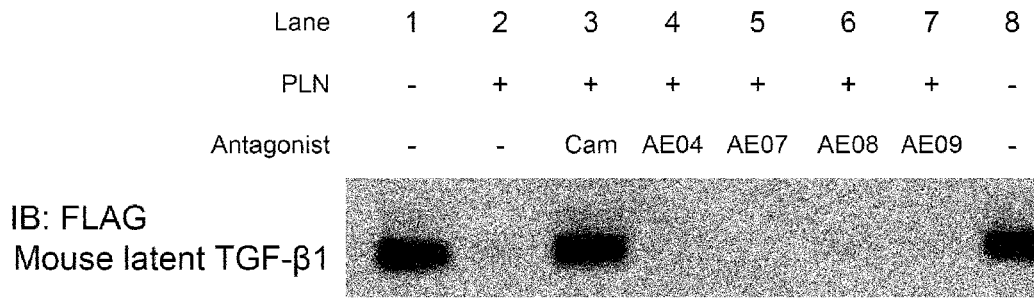
FIG. 7A shows the results of antibody activity against plasmin (PLN)-mediated mouse latent TGF-beta 1 cleavage. Cam represents camostat which is a protease inhibitor used as a control. AE04 (hT0947AE04-SG191), AE07 (hT0947AE07-SG191), AE08 (hT0947AE08-SG191), and AE09 (hT0947AE09-SG191) represent anti-latent TGF-beta 1 antibodies.
Figure 7B:
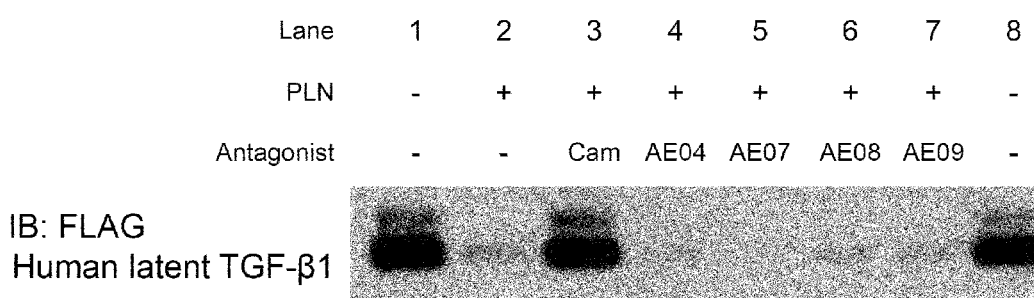
FIG. 7B shows the results of antibody activity against plasmin (PLN)-mediated human latent TGF-beta 1 cleavage. Cam represents camostat which is a protease inhibitor used as a control. AE04 (hT0947AE04-SG191), AE07 (hT0947AE07-SG191), AE08 (hT0947AE08-SG191), and AE09 (hT0947AE09-SG191) represent anti-latent TGF-beta 1 antibodies.

As shown in FIG. 7, latent TGF-beta 1 propeptide cleavage via plasmin was not inhibited by anti-latent TGF-beta 1 antibodies.

(4-8) Anti-Latent TGF-Beta 1 Antibody Did not Significantly Inhibit Integrin-Mediated Latent TGF-Beta 1 Activation in Mouse PBMC Mouse PBMC and HEK-Blue™ TGF-beta cell co-culture assay was conducted to detect integrin-mediated latent TGF-beta 1 activation. Mouse PBMC was isolated from mouse blood by using Histopaque-1083 density gradient medium (Sigma-Aldrich). HEK-Blue™ TGF-beta cells (Invivogen), which express Smad3/4-binding elements (SBE)-inducible SEAP reporter genes, allow the detection of bioactive TGF-beta 1 (both mouse TGF-beta 1 and human TGF-beta 1) by monitoring the activation of Smad3/4. Active TGF-beta 1 stimulates the production of SEAP and its secretion into cell supernatant. The quantity of SEAP secreted was assessed by using QUANTI-Blue™ reagent (Invivogen).

HEK-Blue™ TGF-beta cells were maintained in DMEM medium (Gibco) supplemented with 10% fetal bovine serum, 50 U/mL streptomycin, 50 microgram/mL penicillin, 100 microgram/mL Normocin, 30 microgram/mL of Blasticidin, 200 microgram/mL of HygroGold and 100 microgram/mL of Zeocin. During functional assay, the medium for cells was changed to assay medium (RPMI1640 with 10% FBS) and seeded to 96-well plate. Then the anti-latent TGF-beta 1 antibodies (hT0947AE04-SG191, hT0947AE07-SG191, hT0947AE08-SG191, or hT0947AE09-SG191) and mouse PBMC were applied to the wells and incubated together with HEK-Blue™ TGF-beta cells overnight. Then the cell supernatant was mixed with QUANTI-Blue™ and the optical density (OD) at 620 nm was measured in a colorimetric plate reader. RGD peptide (GRRGDLATIH, GenScript) is known to bind to integrins and serve as a decoy integrin ligand to suppress integrin-mediated TGF-beta 1 activation. Therefore, RGD peptide was used as a positive control. Furthermore, RGE control peptide (GRRGELATIH, GenScript), which is known not to serve as a decoy integrin ligand, was used as a negative control. Anti-KLH antibody (IC17-hIgG1) was used as a negative control. Anti-mature TGF-beta 1 antibody (GC1008-F1332m) was used as a positive control. F1332m is a human IgG1 heavy chain constant region which includes amino acid substitutions to reduce effector function.

Figure 8:
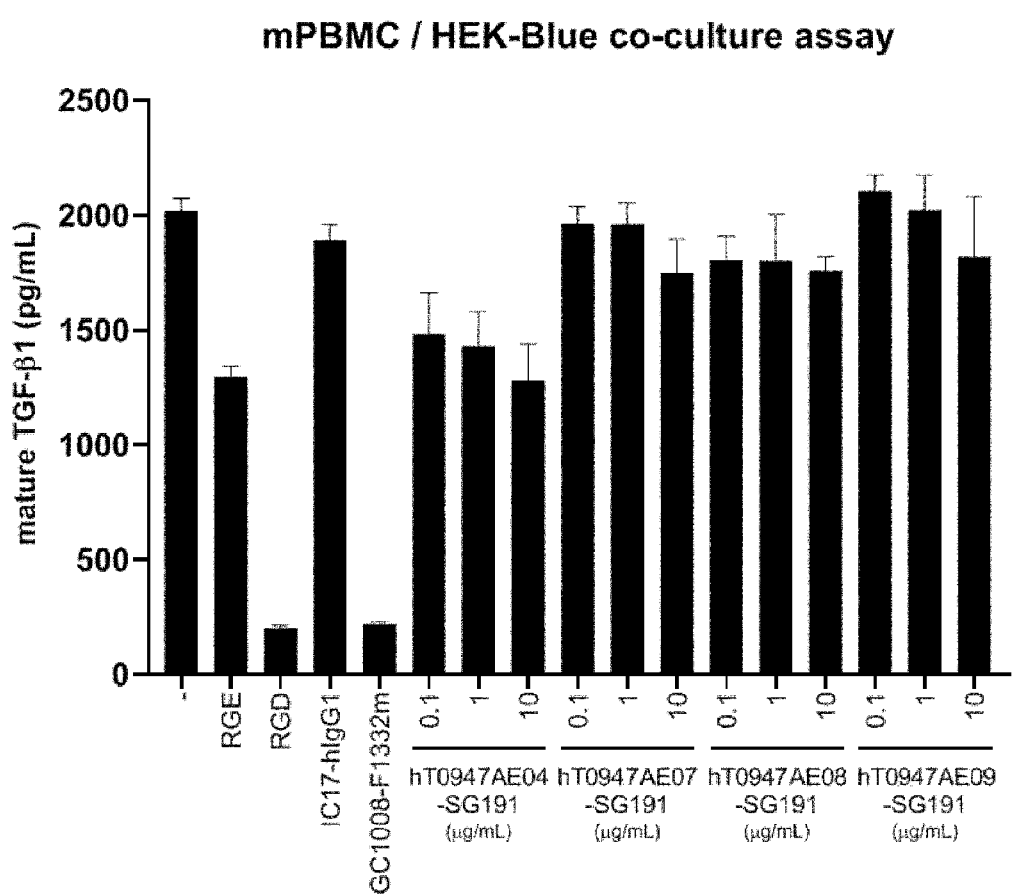
FIG. 8 shows the result of antibody activity against integrin-mediated mouse TGF-beta 1 activation in mouse PBMC. IC17-hIgG1 represents an anti-KLH antibody as a negative control. GC1008-F1332m represents anti-mature TGF-beta antibody as a positive control. RGE represents RGE peptide. RGD represents RGD peptide as a positive control. hT0947AE04-SG191, hT0947AE07-SG191, hT0947AE08-SG191, and hT0947AE09-SG191 represent anti-latent TGF-beta 1 antibodies.

As shown in FIG. 8, anti-latent TGF-beta 1 antibodies did not significantly inhibited integrin-mediated TGF-beta 1 activation in mouse PBMC.

Example 5. Antitumor Activity of the Anti-Latent TGF-Beta 1 Antibody (1)

The in vivo efficacy of anti-latent TGF-beta 1 monoclonal antibody hT0947AE04-mF18 alone or in combination with an anti-PD-L1 antibody were evaluated in a mouse syngeneic model with EMT6 murine mammary carcinoma cells and Balb/c mice, in which immune checkpoint inhibitor treatment alone has shown limited effects on tumor growth and survival (See, Nature. 2018 Feb. 22; 554(7693):544-548.).

(5-1) Establishment of Mouse Syngeneic Model

The EMT6 murine mammary carcinoma cell line was obtained from American Type Culture Collection (ATCC CRL-2755). Cells were cultured in RPMI-1640 medium (SIGMA) plus 2 mM L-glutamine (SIGMA) with 10% fetal bovine serum (FBS; SIGMA). Specific pathogen-free Balb/c female mice of 6 weeks of age were purchased from Japan Charles River Inc. and were acclimated for 2 week before the inoculation. EMT6 cells in log-phase growth were harvested and washed with Hank's balanced salt solution (HBSS; SIGMA), re-suspended in 50% HBSS and 50% Matrigel (CORNING) at a concentration of $1 \times 10^6$ cells/mL. Mice were inoculated in the left mammary fat pad #5 with $1 \times 10^5$ EMT6 cells in 100 microliter of HBSS:Matrigel (1:1).

When mean tumor volume reached about 100-300 mm$^3$ (7 days after inoculation), mice were randomized into groups based on tumor volume and body weight. Tumor volume was measured with caliper, and tumor volume was calculated as follows:

Tumor volume (mm$^3$)=(½)×length (mm)×width (mm)$^2$ (5-2) Evaluation of Antitumor Activity Following the establishment of the mouse model in Example (5-1), mice were treated with isotype control antibodies (mouse IgG1 antibody in combination with rat IgG2b antibody, purchased from Bio X Cell), anti-mouse PD-L1 antibody (rat IgG2b clone 10F.9G2, purchased from Bio X Cell), hT0947AE04-mF18 or a combination of hT0947AE04-mF18 with the anti-mouse PD-L1 antibody, as shown in Table 4. Antibodies were administered 3 times a week for 3 weeks. The first dose was administered intravenously, and the second dose and thereafter were administered intraperitoneally.

TABLE 4

| Group | Number of animals | Pharmaceutical agent | Dose [mg/kg] |
| --- | --- | --- | --- |
| 1 | 10 | Mouse IgG1 isotype control antibody Rat IgG2b isotype control antibody | Mouse IgG1 isotype control antibody: 10 mg/kg Rat IgG2b isotype control antibody: 10 mg/kg (first dose), 5 mg/kg (second dose and thereafter) |
| 2 | 10 | Mouse IgG1 isotype control antibody Anti-mouse PD-L1 antibody (10F.9G2) | Mouse IgG1 isotype control antibody: 10 mg/kg Anti-mouse PD-L1 antibody: 10 mg/kg (first dose), 5 mg/kg (second dose and thereafter) |
| 3 | 10 | hT0947AE04-mF18 Rat IgG2b isotype control antibody | hT0947AE04-mF18: 10 mg/kg Rat IgG2b isotype control antibody: 10 mg/kg (first dose), 5 mg/kg (second dose and thereafter) |
| 4 | 10 | hT0947AE04-mF18 Anti-mouse PD-L1 antibody (10F.9G2) | hT0947AE04-mF18: 10 mg/kg anti-mouse PD-L1 antibody: 10 mg/kg (first dose), 5 mg/kg (second dose and thereafter) |

Figure 9:
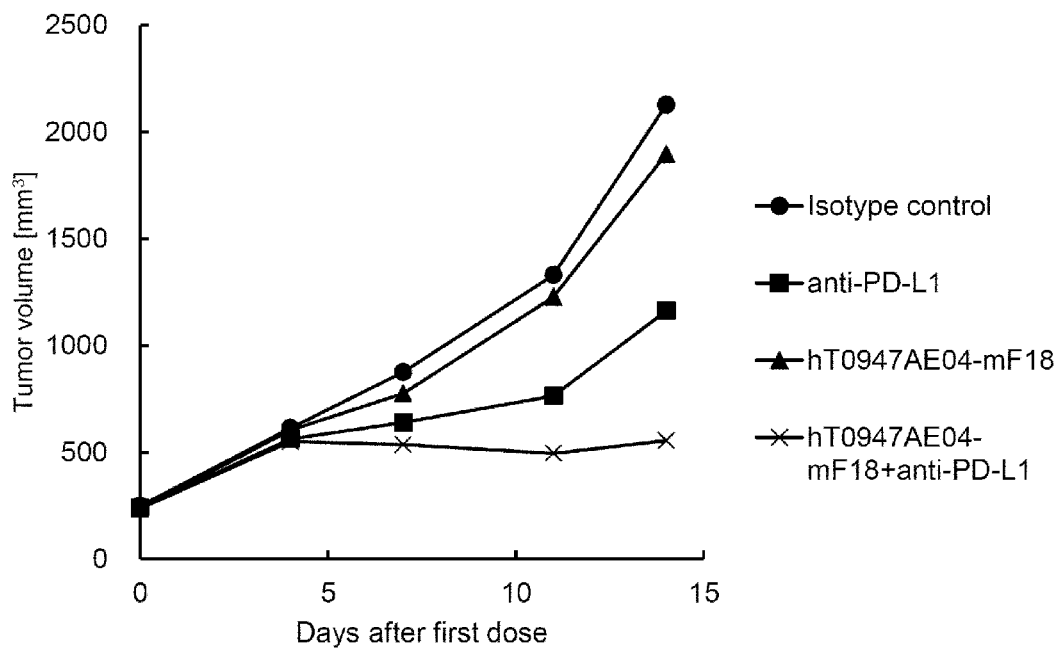
FIG. 9 shows the tumor growth curves of isotype control treated group (closed circle), anti-PD-L1 treated group (closed square), hT0947AE04-mF18 treated group (closed triangle) and hT0947AE04-mF18 plus anti-PD-L1 treated group (cross). Each point represents the mean tumor volume of each group. (N=10)

Tumor volume was measured twice weekly. The result was shown in FIG. 9.

Anti-tumor activity was also evaluated by tumor growth inhibition (TGI[%]). TGI[%] of a specific Group on a specific day was calculated as follows:

TGI[%]={1−(T−T0)/(C−C0)}×100 wherein 'T' is the mean tumor volume of the Group on the day of measurement, 'T0' is the mean tumor volume of the Group on the day of randomization, 'C' is the mean tumor volume of Group 1 (isotype control) on the day of measurement, and 'C0' is the mean tumor volume of the Group 1 (isotype control) on the day of randomization.

As a result, values of TGI[%] of anti-mouse PD-L1 antibody (Group 2), hT0947AE04-mF18 (Group 3) and the combination of hT0947AE04-mF18 with anti-mouse PD-L1 antibody (Group 4) on the 14th day after the first dose were 51, 12 and 83, respectively. Therefore, synergistic antitumor effect between anti-latent TGF-beta 1 (hT0947AE04-mF18) and anti-PD-L1 antibody was observed.

Figure 10:
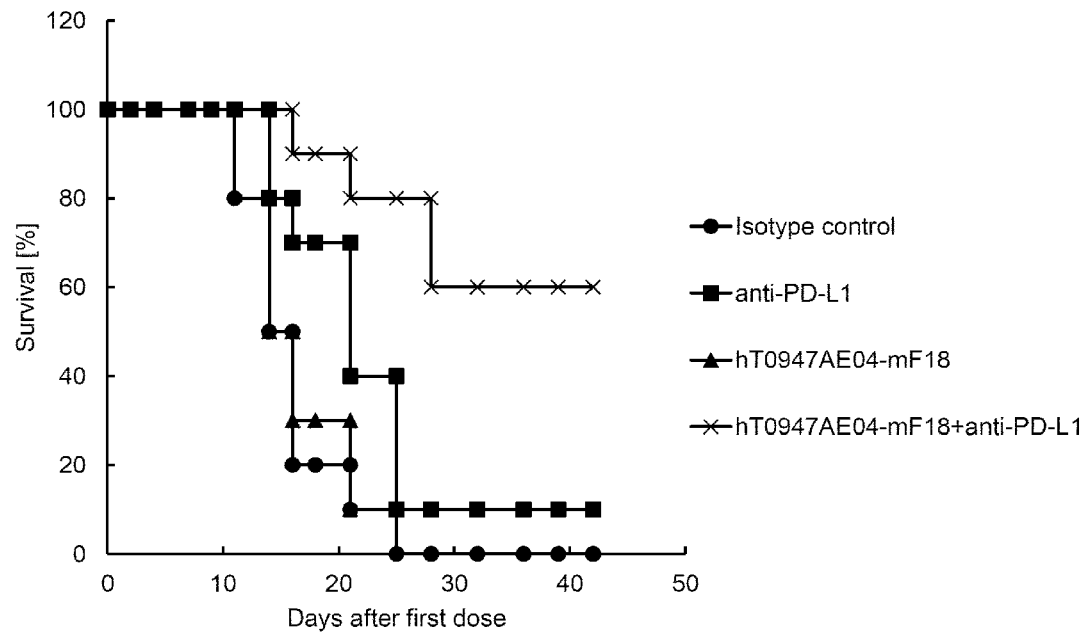
FIG. 10 shows the tumor growth curves of isotype control treated group (closed circle), anti-PD-L1 treated group (closed square), hT0947AE04-mF18 treated group (closed triangle) and hT0947AE04-mF18 plus anti-PD-L1 treated group (cross). Each point represents the mean tumor volume of each group. (N=10)

Survival curves were also plotted to evaluate the survival of each group. The definition of "survived" mouse is as follows: its tumor volume did not exceed 1955 mm$^3$. As shown in FIG. 10, the combination treatment of hT0947AE04-mF18 with anti-mouse PD-L1 antibody (Group 4) significantly increased survival of the mice compared with that of the anti-mouse PD-L1 antibody treated mice (Group 2) and hT0947AE04-mF18 treated mice (Group 3).

Example 6. Antitumor Activity of the Anti-Latent TGF-Beta 1 Antibody (2)

The in vivo efficacies of anti-latent TGF-beta 1 monoclonal antibodies hT0947AE04-mF18, hT0947AE07-SG181 or hT0947AE08-SG181 in combination with an anti-PD-L1 antibody were evaluated in a mouse syngeneic model with EMT6 murine mammary carcinoma cells and Balb/c mice.

(6-1) Establishment of Mouse Syngeneic Model

The EMT6 murine mammary carcinoma cell line was obtained from American Type Culture Collection (ATCC CRL-2755). Cells were cultured in RPMI-1640 medium (SIGMA) plus 2 mM L-glutamine (SIGMA) with 10% fetal bovine serum (FBS; SIGMA). Specific pathogen-free Balb/c female mice of 7 weeks of age were purchased from Japan Charles River Inc. and were acclimated for 1 week before the inoculation. EMT6 cells in log-phase growth were harvested and washed with Hank's balanced salt solution (HBSS; SIGMA), resuspended in 50% HBSS and 50% Matrigel (CORNING) at a concentration of 1×10$^6$ cells/mL. Mice were inoculated in the left mammary fat pad #5 with 1×10$^5$ EMT6 cells in 100 microliter of HBSS:Matrigel (1:1).

When mean tumor volume reached about 100-300 mm$^3$ (7 days after inoculation), mice were randomized into groups based on tumor volume and body weight. Tumor volume was measured with caliper, and tumor volume was calculated as follows:

Tumor volume (mm$^3$)=(½)×length (mm)×width (mm)$^2$ (6-2) Evaluation of Antitumor Activity Following the establishment of the mouse model in Example (6-1), mice were treated with vehicle (150 mM NaCl/20 mM His-HCl buffer pH6.0), anti-mouse PD-L1 antibody (rat IgG2b clone 10F.9G2, purchased from Bio X Cell), a combination of hT0947AE04-mF18 with the anti-mouse PD-L1 antibody, a combination of hT0947AE07-SG181 with the anti-mouse PD-L1 antibody or a combination of hT0947AE08-SG181 with the anti-mouse PD-L1 antibody as shown in Table 5. Antibodies were administered 3 times a week for 3 weeks. The first dose was administered intravenously, and the second dose and thereafter were administered intraperitoneally.

TABLE 5

| Group | Number of animals | Pharmaceutical agent | Dose [mg/kg] |
| --- | --- | --- | --- |
| 1 | 10 | vehicle | — |
| 2 | 10 | Anti-mouse PD-L1 antibody (10F.9G2) | 10 mg/kg (first dose), 5 mg/kg (second dose and thereafter) |
| 3 | 10 | hT0947AE04-mF18 in combination with anti-mouse PD-L1 antibody (10F.9G2) | hT0947AE04-mF18: 10 mg/kg anti-mouse PD-L1 antibody: 10 mg/kg (first dose), 5 mg/kg (second dose and thereafter) |
| 4 | 10 | hT0947AE07-SG181 in combination with anti-mouse PD-L1 antibody (10F.9G2) | hT0947AE04-SG181: 10 mg/kg anti-mouse PD-L1 antibody: 10 mg/kg (first dose), 5 mg/kg (second dose and thereafter) |

TABLE 5-continued

| Group | Number of animals | Pharmaceutical agent | Dose [mg/kg] |
|---|---|---|---|
| 5 | 10 | hT0947AE08-SG181 in combination with anti-mouse PD-L1 antibody (10F.9G2) | hT0947AE08-SG181: 10 mg/kg anti-mouse PD-L1 antibody: 10 mg/kg (first dose), 5 mg/kg (second dose and thereafter) |

Figure 11:
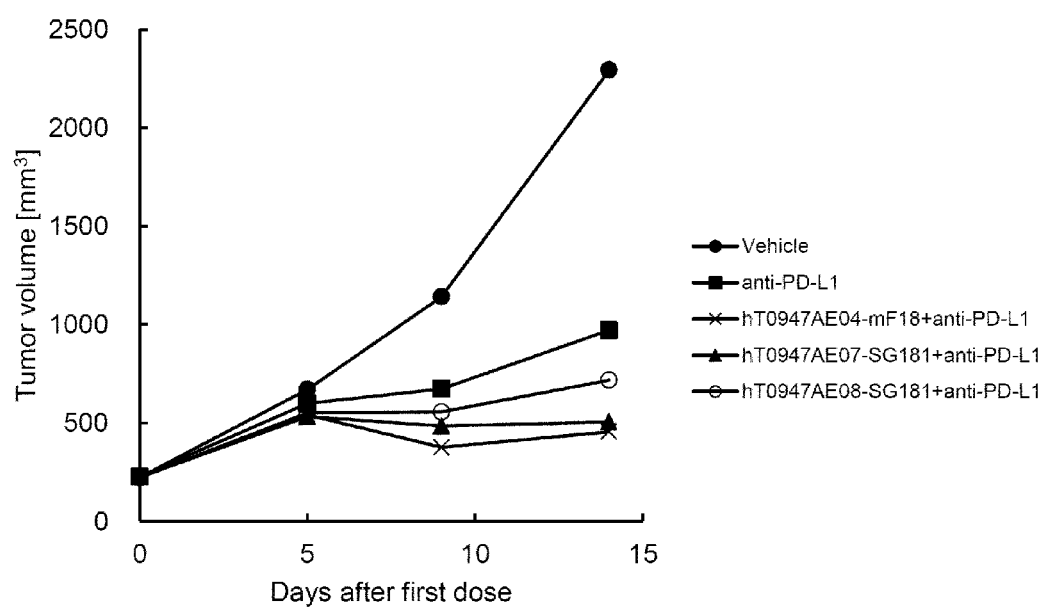
FIG. 11 shows the tumor growth curves of vehicle treated group (closed circle), anti-PD-L1 treated group (closed square), hT0947AE04-mF18 plus anti-PD-L1 treated group (X) hT0947AE07-SG181 plus anti-PD-L1 treated group (closed triangle) and hT0947AE08-SG181 plus anti-PD-L1 treated group (open circle). Each point represents the mean tumor volume of each group. (N=10)

Tumor volume was measured twice weekly. The result is shown in FIG. 11.

Anti-tumor activity was also evaluated by tumor growth inhibition (TGI[%]). (TGI[%]) was calculated as $\{1-(T-T0)/(C-C0)\} \times 100$, which is the same as in Example (5-2).

TGI[%] of anti-mouse PD-L1 antibody alone (Group 2), the combination of hT0947AE04-mF18 with anti-mouse PD-L1 antibody (Group 3), the combination of hT0947AE07-SG181 with anti-mouse PD-L1 antibody (Group 4) and the combination of hT0947AE08-SG181 with anti-mouse PD-L1 antibody (Group 5) on the 14th day after the first dose were 64, 89, 86 and 76, respectively. Therefore, anti-latent TGF-beta 1 antibodies showed combinatorial efficacy with anti-PD-L1 antibody.

Example 7. In Vivo Efficacy of Anti-Latent TGF-Beta 1 Antibodies in UUO Induced Mouse Renal Fibrosis Model The in vivo efficacy of monoclonal antibodies hT0947AE04-SG191, hT0947AE07-SG191, and hT0947AE08-SG191 were evaluated in Unilateral Ureteral Obstruction (UUO) mouse model which is known to induce a progressive renal fibrosis.

(7-1) Establishment of UUO Induced Mouse Renal Fibrosis Model

The in vivo efficacies of monoclonal antibodies hT0947AE04-SG191, hT0947AE07-SG191, and hT0947AE08-SG191 were evaluated in Unilateral Ureteral Obstruction (UUO) mouse model which induces a progressive renal fibrosis.

Specific pathogen-free C57BL/6NTac male mice of 6 weeks of age were purchased from Invivos Pte Ltd (Singapore) and were acclimated for 1 weeks before the start of treatments. Animals were maintained at 20 to 26 degree C. with a 12:12 hour light/dark cycle and fed with a commercial standard diet (5P75; PMI Nutrition INT'L (LabDiet), Missouri, United States) and tap water ad libitum.

UUO surgery was operated under isoflurane anesthetized condition. The left side of the abdomen was shaved and a vertical incision was made through the skin. A second incision was made through the peritoneum and that skin was also retracted to reveal the kidney. Using forceps, the kidney was brought to the surface and the left ureter was tied with surgical silk, twice, below the kidney. The ligated kidney was placed gently back into its correct anatomical position then peritoneum and skin were sutured. Analgesic agent was added to reduce animal affliction. In the sham operated group, peritoneum and skin were only incised and sutured.

(7-2) Evaluation of In Vivo Efficacy

All monoclonal antibodies were administered at 15 mg/kg by intravenous injection three times a week starting from one day before the surgical operation. Anti-KLH antibody (IC17dk-SG181) was used as a negative control in this study. The sham operated group was administered Anti-KLH antibody (IC17dk-SG181). The animals were weighed and then killed by exsanguination under isoflurane anaesthesia 7 days after operation. Blood samples were collected from the heart cavities or the postcaval vein and maintained at −80 degree C. until assayed. The kidney was quickly removed. Part of the kidney tissue was snap-frozen in liquid nitrogen or on dry ice for molecular analyses.

Figure 12:
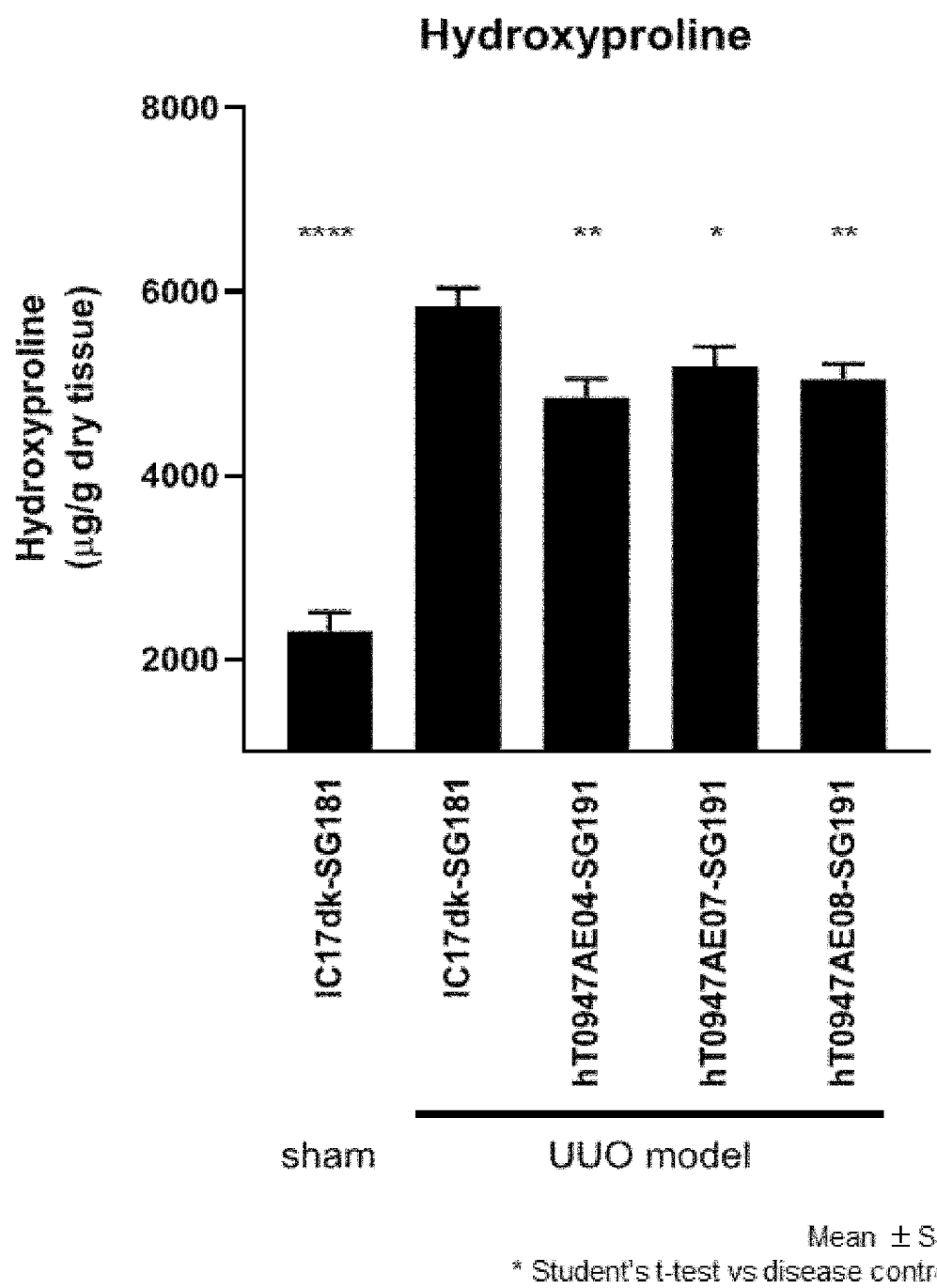
FIG. 12 shows the result of hydroxyproline content in kidney. Monoclonal antibodies were evaluated in Unilateral Ureteral Obstruction (UUO) induced mouse renal fibrosis model. Sham operated group represents as non-disease induced control. IC17dk-SG181 is an anti-KLH antibody used as a negative control. hT0947AE04-SG191, hT0947AE07-SG191, and hT0947AE08-SG191 represent anti-latent TGF-beta 1 antibodies.

The hydroxyproline contents in kidney, which is one of the amino acids included in collagen, was measured to evaluate the extramatrix deposition to the tissue. Wet kidney tissues were dried up at 95 degree C. for 3 hours and weighed. Then, 6N HCl (100 microliter/1 mg dry tissue) was added to the dried tissue and boiled at overnight. Samples were cleaned up by the filter and 10 microliter of each sample was plated into the 96-well plate. The plate with samples was dried out at 60 degree C. and hydroxyproline was measured using hydroxyproline assay kit (BioVision). The results of this experiment are shown in FIG. 12. Significant increase in hydroxyproline content was observed in disease induced kidney, and all antibodies (hT0947AE04-SG191, hT0947AE07-SG191, and hT0947AE08-SG191) inhibited kidney fibrosis. Data are presented as mean+/− standard error of the mean (SEM). Statistical analysis was performed using analysis of Student's t-test. When P values were <0.05, differences were considered significant.

Example 8. Toxicity Evaluation of Anti-Latent TGF-Beta 1 Antibodies

Potential toxicity of anti-latent TGF-beta 1 antibody were evaluated in repeat-dose toxicity study in normal mice and cynomolgus monkeys compared with anti-mature TGF-beta antibody GC1008-mF18 (anti-mature TGF-beta antibody GC1008 (as described in U.S. Pat. No. 8,383,780) having mouse IgG Fc region mF18). Because the anti-latent TGF-beta 1 antibody cross-reacted in mouse and cynomolgus monkey, mouse and cynomolgus monkey were selected as the animal species for evaluations in the in vivo toxicology studies. For a summary of all toxicology studies, see Table 6.

TABLE 6

Summary of Toxicology Studies

| Study Type | Species/ Test System | Treatment/ Duration | Animals/ Group | Dose (mg/kg) |
|---|---|---|---|---|
| Repeat-dose toxicity: | | | | |
| 3-month study | Mouse (BALB/c; 6 weeks of age) | IV, 3 months (3 months recovery), Q2D, 46 doses in total | [hT0947AE04-mF18 or GC1008-mF18] Main: 10/female Recovery: 10/female TK: 6/female | 0 [a], 5 [b], 20 |
| 6-week study | Cynomolgus monkey (3 to 4 years of age) | IV, 6 weeks, Q2W, 4 doses in total | [hT0947AE07-SG191] 1/sex | 0 [c], 10, 30, 100 [b] |

IV = intravenous; Q2D = once per 2 days; Q2W = once per 2 weeks; NOAEL = no observed adverse effect level;
[a] - Vehicle, 150 mmol/L NaCl, 20 mmol/L histidine-HCL, pH 6.0
[b] - NOAEL is underlined
[c] - Vehicle, 20 mmol/L histidine, 150 mmol/L arginine-aspartate, pH 6.0

In the mouse 3-month study (IV; 5, or 20 mg/kg, Q2D, 46 doses in total), anemic changes (at 20 mg/kg in the hT0947AE04-mF18 group; at 5 and 20 mg/kg in GC1008-mF18 groups) and cardiac lesions (at 5 and 20 mg/kg in GC1008-mF18 groups; see Table 7) were observed. These findings were considered to be caused by on-target toxicities of TGF-beta inhibition. Considering the on-target toxicities in the mouse 3-month study, the NOAEL for hT0947AE04-mF18 was 5 mg/kg IV Q2D. In addition, because the adverse effects for GC1008-mF18 at 5 mg/kg group, the NOAEL for GC1008-mF18 was not determined in the condition of the mouse 3-month study.

TABLE 7

Major Findings in Histopathology of Mouse 3-month Toxicity Study

| | | Control (Vehicle; n = 20/dose) | GC1008-mF18 (n = 26/dose) | | hT0947AE04-mF18 (n = 26/dose) | |
|---|---|---|---|---|---|---|
| | | | Dose (mg/kg Q2D) | | | |
| | Major | 0 | 5 | 20 | 5 | 20 |
| Organs | findings | | Death/Moribund | | | |
| | | 0 | 6 | 12 | 0 | 0 |
| Heart | Mesenchymal cell, aortic root/valve | 2 (±) | 3 (+~2+) | 11 (+~2+) | 0 | 1[a] (±) |
| | Cell infiltration in aortic root/valve | 2 (±) | 4 (±~2+) | 11 (+~2+) | 0 | 1[a] (±) |
| | Hemorrhage, aortic root/valve | 0 | 2 (±) | 7 (±) | 0 | 0 |
| Lung | Hemorrhage, bronchus | 0 | 0 | 7 | NE | 0 |

NE = not examined; ± = minimal; + = mild; 2+ = moderate.
[a] -hT0947AE04-mF18-unrelated changes based on same findings/degrees in the vehicle control group (minimal changes in 2 mice)

In the monkey 6-week study (IV; 10, 30, or 100 mg/kg, Q2W, 4 doses in total), no toxicologically relevant changes attributable to IV administration of hT0947AE07-SG191 were observed, and the NOAEL was the highest tested dose of 100 mg/kg Q2W.

Example 9. Antitumor Activity of the Anti-Latent TGF-Beta 1 Antibody (3)

The in vivo efficacy of anti-latent TGF-beta 1 monoclonal antibody hT0947AE07-SG191 in combination with an anti-mouse PD-L1 antibody were evaluated in the EMT6 murine mammary carcinoma Balb/c mouse syngeneic model.

The EMT6 murine mammary carcinoma cell line was obtained from American Type Culture Collection. Cells were cultured in RPMI-1640 medium (SIGMA) with 10% fetal bovine serum (FBS; Nichirei Biosciences Inc). Specific pathogen-free Balb/c female mice of 6 weeks of age were purchased from Japan Charles River Inc. and were acclimated for 1 week before the inoculation. EMT6 cells in log-phase growth were harvested and washed with Hank's balanced salt solution (HBSS; SIGMA), resuspended in 50% HBSS and 50% Matrigel (CORNING) at a concentration of $1 \times 10^6$ cells/mL. Mice were inoculated in the left mammary fat pad #5 with $1 \times 10^5$ EMT6 cells in 100 micro L of HBSS:Matrigel (1:1).

When mean tumor volume reached about 100-300 mm³ (7 days after inoculation), mice were randomized into groups based on tumor volume and body weight. Tumor volume was measured with caliper, and tumor volume was calculated as $\frac{1}{2} \times 1 \times w^2$, l=length, w=width.

Mice were treated with vehicle (150 mM NaCl/20 mM His-HCl buffer pH6.0), anti-mouse PD-L1 antibody (rat IgG2b clone 10F.9G2, purchased from Bio X cell, 10 mg/kg first dose followed by 5 mg/kg thereafter), a combination of hT0947AE07-SG191 (10 mg/kg) with anti-mouse PD-L1 antibody or a combination of hT0947AE07-SG191 (30 mg/kg) with anti-mouse PD-L1 antibody. Antibodies were administered 3 times a week for 2 weeks, intravenously for the first dose and intraperitoneally thereafter.

Tumor volume was measured twice a week. Anti-tumor activity was evaluated by tumor growth inhibition (TGI[%]) which was calculated as $\{1-(T-T0)/(C-C0)\} \times 100$, where the mean tumor volumes for the groups were T on the day of measurement and T0 on the day of randomization, likewise represented by C and C0 for the vehicle control group.

Figure 13:
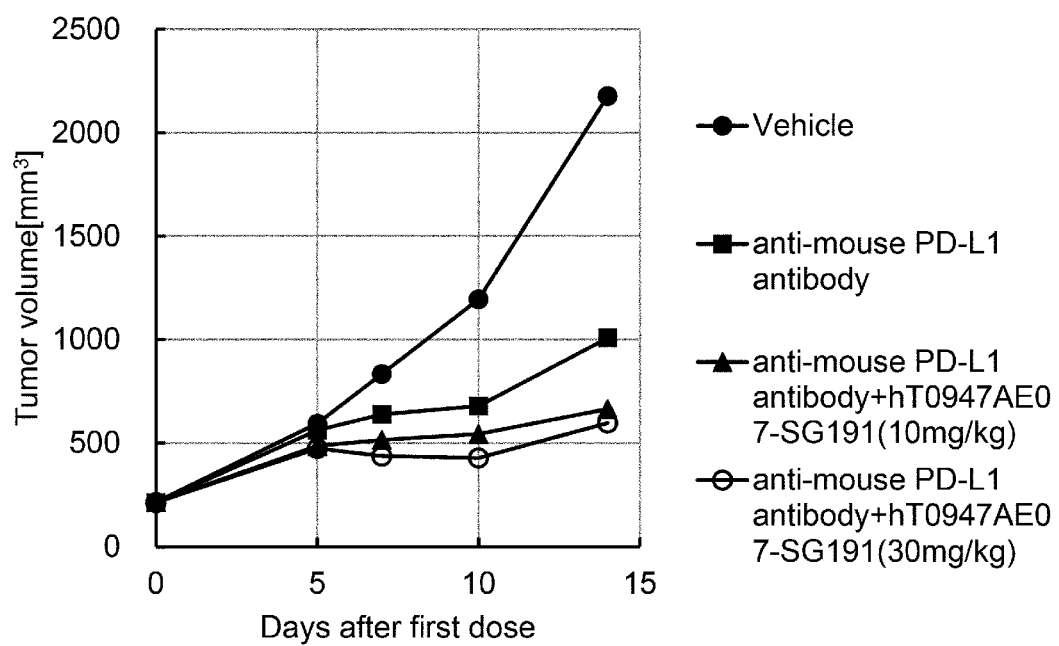
FIG. 13 shows the tumor growth curves of vehicle treated group (closed circle), anti-mouse PD-L1 antibody treated group (closed square), hT0947AE07-SG191 (10 mg/kg) plus anti-mouse PD-L1 antibody treated group (closed triangle) and hT0947AE07-SG191 (30 mg/kg) plus anti-mouse PD-L1 antibody treated group (open circle). Each point represents the mean tumor volume of corresponding group. (N=10 in each group)

The results of this experiment is shown in FIG. 13.

TGI[%] of anti-mouse PD-L1 antibody alone, combination of hT0947AE07-SG191(10 mg/kg) with anti-mouse PD-L1 antibody, and combination of hT0947AE07-SG191(30 mg/kg) with anti-mouse PD-L1 antibody on 14 days after first dose were 60, 77 and 80, respectively. hT0947AE07-SG191 showed combinatorial efficacy with anti-mouse PD-L1 antibody.

Although the present invention is described herein in some detail by way of illustration and example for purposes of clarity of understanding, the descriptions and examples should not be construed as limiting the scope of the invention. The disclosures of all patent and scientific literature cited herein are expressly incorporated in their entirety by reference.

INDUSTRIAL APPLICABILITY

The present invention provides cross-species anti-latent TGF-beta 1 antibodies which inhibit a protease mediated activation of latent TGF-beta 1 without inhibiting integrin mediated activation of latent TGF-beta 1. The invention also provides combination therapies comprising an anti-latent TGF-beta 1 antibody and a checkpoint inhibitor. The anti-latent TGF-beta 1 antibodies of the present invention, which may be administered in combination with a checkpoint inhibitor, are expected to be useful for treating TGF-beta 1-related diseases such as fibrosis and cancer.

Sequence Listing

The invention claimed is:

1. An anti-latent TGF-beta 1 antibody comprising:
(a) HVR-H1, HVR-H2 and HVR-H3 comprising the amino acid sequences of SEQ ID NO:20, 21 and 22, respectively, and HVR-L1, HVR-L2 and HVR-L3 comprising the amino acid sequences of SEQ ID NO:23, 24 and 25, respectively;
(b) HVR-H1, HVR-H2 and HVR-H3 comprising the amino acid sequences of SEQ ID NO:26, 27 and 28, respectively, and HVR-L1, HVR-L2 and HVR-L3 comprising the amino acid sequences of SEQ ID NO:29, 30 and 31, respectively;
(c) HVR-H1, HVR-H2 and HVR-H3 comprising the amino acid sequences of SEQ ID NO:32, 33 and 34, respectively, and HVR-L1, HVR-L2 and HVR-L3 comprising the amino acid sequences of SEQ ID NO:35, 36 and 37, respectively; or
(d) HVR-H1, HVR-H2 and HVR-H3 comprising the amino acid sequences of SEQ ID NO:38, 39 and 40, respectively, and HVR-L1, HVR-L2 and HVR-L3 comprising the amino acid sequences of SEQ ID NO:41, 42 and 43, respectively.

2. The anti-latent TGF-beta 1 antibody of claim 1, comprising:
(a) (i) a VH sequence having at least 95% sequence identity to the amino acid sequence of SEQ ID NO:12, and
(ii) a VL sequence having at least 95% sequence identity to the amino acid sequence of SEQ ID NO:13;
(b) (i) a VH sequence having at least 95% sequence identity to the amino acid sequence of SEQ ID NO:14, and
(ii) a VL sequence having at least 95% sequence identity to the amino acid sequence of SEQ ID NO:15;
(c) (i) a VH sequence having at least 95% sequence identity to the amino acid sequence of SEQ ID NO:16, and
(ii) a VL sequence having at least 95% sequence identity to the amino acid sequence of SEQ ID NO:17; or (d) (i) a VH sequence having at least 95% sequence identity to the amino acid sequence of SEQ ID NO:18, and
(ii) a VL sequence having at least 95% sequence identity to the amino acid sequence of SEQ ID NO:19.

3. The anti-latent TGF-beta 1 antibody of claim 1, comprising:
(a) a VH sequence of SEQ ID NO:12 and a VL sequence of SEQ ID NO:13;
(b) a VH sequence of SEQ ID NO:14 and a VL sequence of SEQ ID NO:15;
(c) a VH sequence of SEQ ID NO:16 and a VL sequence of SEQ ID NO:17; or
(d) a VH sequence of SEQ ID NO:18 and a VL sequence of SEQ ID NO:19.

4. The anti-latent TGF-beta 1 antibody of claim 1, which is a humanized or chimeric antibody.

5. The anti-latent TGF-beta 1 antibody of claim 1, which is a full length IgG antibody.

6. The anti-latent TGF-beta 1 antibody of claim 1, wherein the anti-latent TGF-beta 1 antibody comprises a modified IgG1 Fc region having reduced effector function compared with a wild type IgG1 Fc region.

7. The anti-latent TGF-beta 1 antibody of claim 1 comprising:
(a) a full length heavy chain sequence of SEQ ID NO:47 and a full length light chain sequence of SEQ ID NO:60;
(b) a full length heavy chain sequence of SEQ ID NO:48 and a full length light chain sequence of SEQ ID NO:61;
(c) a full length heavy chain sequence of SEQ ID NO:49 and a full length light chain sequence of SEQ ID NO:62;
(d) a full length heavy chain sequence of SEQ ID NO:50 and a full length light chain sequence of SEQ ID NO:63;
(e) a full length heavy chain sequence of SEQ ID NO:51 and a full length light chain sequence of SEQ ID NO:60;
(f) a full length heavy chain sequence of SEQ ID NO:52 and a full length light chain sequence of SEQ ID NO:61;
(g) a full length heavy chain sequence of SEQ ID NO:53 and a full length light chain sequence of SEQ ID NO:62; or
(h) a full length heavy chain sequence of SEQ ID NO:54 and a full length light chain sequence of SEQ ID NO:63.

8. An immunoconjugate comprising the anti-latent TGF beta-1 antibody of claim 1 and a cytotoxic agent.

9. An isolated nucleic acid encoding the anti-latent TGF beta-1 antibody of claim 1.

10. A vector comprising the nucleic acid of claim 9.

11. A host cell comprising the nucleic acid of claim 9.

12. A method of producing an anti-latent TGF beta-1 antibody comprising culturing the host cell of claim 11 so that the antibody is produced.

13. A pharmaceutical formulation comprising the anti-latent TGF beta-1 antibody of claim 1 and a pharmaceutically acceptable carrier.

14. The anti-latent TGF-beta 1 antibody of claim 1, which is a full length IgG1 antibody.

15. The anti-latent TGF-beta 1 antibody of claim 1, which binds to latent TGF-beta 1 forming SLC.

16. The anti-latent TGF-beta 1 antibody of claim 1, which binds to latent TGF-beta 1 forming LLC.

17. The anti-latent TGF-beta 1 antibody of claim 1, which binds to LAP region of latent TGF-beta 1.

18. A host cell comprising the vector of claim 10.

19. A pharmaceutical formulation comprising the immunoconjugate of claim 8 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 11,312,767 B2 | Page 1 of 1 |
| APPLICATION NO. | : 17/466509 | |
| DATED | : April 26, 2022 | |
| INVENTOR(S) | : Shimada et al. | |

It is certified that error appears in the above-identified patent and that said Letters Patent is hereby corrected as shown below:

On the Title Page

Assignees' item (73), please replace "Assignees: Chugai Seiyaku Kabushiki Kaisha, Tokyo (JP); Chugai Pharmabody Research Pte. Ltd., Singapore (SG)" with -- Assignee: Chugai Seiyaku Kabushiki Kaisha, Tokyo (JP) --.

Signed and Sealed this
Fifth Day of August, 2025

Coke Morgan Stewart
*Acting Director of the United States Patent and Trademark Office*

SEQUENCE LISTING

```
<160> NUMBER OF SEQ ID NOS: 73

<210> SEQ ID NO 1
<211> LENGTH: 387
<212> TYPE: PRT
<213> ORGANISM: Artificial Sequence
<220> FEATURE:
<223> OTHER INFORMATION: flag-tagged human latent TGF-beta 1

<400> SEQUENCE: 1
```

```
Met Lys Trp Val Thr Phe Leu Leu Leu Phe Ile Ser Gly Ser Ala
1               5                   10                  15
Phe Ser Asp Tyr Lys Asp Asp Asp Lys Leu Ser Thr Ser Lys Thr
            20                  25                  30
Ile Asp Met Glu Leu Val Lys Arg Lys Arg Ile Glu Ala Ile Arg Gly
        35                  40                  45
Gln Ile Leu Ser Lys Leu Arg Leu Ala Ser Pro Ser Gln Gly Glu
    50                  55                  60
Val Pro Pro Gly Pro Leu Pro Glu Ala Val Leu Ala Leu Tyr Asn Ser
65                  70                  75                  80
Thr Arg Asp Arg Val Ala Gly Glu Ser Ala Glu Pro Glu Pro Glu Pro
                85                  90                  95
Glu Ala Asp Tyr Tyr Ala Lys Glu Val Thr Arg Val Leu Met Val Glu
                100                 105                 110
Thr His Asn Glu Ile Tyr Asp Lys Phe Lys Gln Ser Thr His Ser Ile
                115                 120                 125
Tyr Met Phe Phe Asn Thr Ser Glu Leu Arg Glu Ala Val Pro Glu Pro
        130                 135                 140
Val Leu Leu Ser Arg Ala Glu Leu Arg Leu Leu Arg Leu Lys Leu Lys
145                 150                 155                 160
Val Glu Gln His Val Glu Leu Tyr Gln Lys Tyr Ser Asn Asn Ser Trp
                165                 170                 175
Arg Tyr Leu Ser Asn Arg Leu Leu Ala Pro Ser Asp Ser Pro Glu Trp
            180                 185                 190
Leu Ser Phe Asp Val Thr Gly Val Val Arg Gln Trp Leu Ser Arg Gly
        195                 200                 205
Gly Glu Ile Glu Gly Phe Arg Leu Ser Ala His Cys Ser Cys Asp Ser
210                 215                 220
Arg Asp Asn Thr Leu Gln Val Asp Ile Asn Gly Phe Thr Thr Gly Arg
225                 230                 235                 240
Arg Gly Asp Leu Ala Thr Ile His Gly Met Asn Arg Pro Phe Leu Leu
            245                 250                 255
Leu Met Ala Thr Pro Leu Glu Arg Ala Gln His Leu Gln Ser Ser Arg
        260                 265                 270
His Arg Arg Ala Leu Asp Thr Asn Tyr Cys Phe Ser Ser Thr Glu Lys
    275                 280                 285
Asn Cys Cys Val Arg Gln Leu Tyr Ile Asp Phe Arg Lys Asp Leu Gly
290                 295                 300
Trp Lys Trp Ile His Glu Pro Lys Gly Tyr His Ala Asn Phe Cys Leu
305                 310                 315                 320
Gly Pro Cys Pro Tyr Ile Trp Ser Leu Asp Thr Gln Tyr Ser Lys Val
                325                 330                 335
Leu Ala Leu Tyr Asn Gln His Asn Pro Gly Ala Ser Ala Ala Pro Cys
            340                 345                 350
Cys Val Pro Gln Ala Leu Glu Pro Leu Pro Ile Val Tyr Tyr Val Gly
        355                 360                 365
Arg Lys Pro Lys Val Glu Gln Leu Ser Asn Met Ile Val Arg Ser Cys
370                 375                 380
Lys Cys Ser
385
```

<210> SEQ ID NO 2
<211> LENGTH: 1167
<212> TYPE: DNA

<213> ORGANISM: Artificial Sequence
<220> FEATURE:
<223> OTHER INFORMATION: flag-tagged human latent TGF-beta 1

<400> SEQUENCE: 2

```
atgaagtggg taacctttct cctcctcctc ttcatctccg gttctgcctt ttccgactac    60
aaggatgacg atgacaagct atccacctcc aagactatcg acatggagct ggtgaagcgg   120
aagcgcatcg aggccatccg cggccagatc ctgtccaagc tgcggctcgc cagcccccg    180
agccagggg aggtgccgcc cggcccgctg cccgaggccg tgctcgccct gtacaacagc    240
acccgcgacc gggtggccgg ggagagtgca gaaccggagc ccgagcctga ggccgactac   300
tacgccaagg aggtcacccg cgtgctaatg gtggaaaccc acaacgaaat ctatgacaag   360
ttcaagcaga gtacacacag catatatatg ttcttcaaca catcagagct ccgagaagcg   420
gtacctgaac ccgtgttgct ctcccgggca gagctgcgtc tgctgaggct caagttaaaa   480
gtggagcagc acgtggagct gtaccagaaa tacagcaaca attcctggcg atacctcagc   540
aaccggctgc tggcacccag cgactcgcca gagtggttat cttttgatgt caccggagtt   600
gtgcggcagt ggttgagccg tggagggaa attgagggct ttcgccttag cgcccactgc   660
tcctgtgaca gcagggataa cacactgcaa gtggacatca acgggttcac taccggccgc   720
cgaggtgacc tggccaccat tcatggcatg aaccggcctt tcctgcttct catggccacc   780
ccgctggaga gggcccagca tctgcaaagc tcccggcacc gccagccct ggacaccaac    840
tattgcttca gctccacgga gaagaactgc tgcgtgcggc agctgtacat tgacttccgc   900
aaggaccctcg gctggaagtg gatccacgag cccaagggct accatgccaa cttctgcctc   960
gggccctgcc cctacatttg gagcctggac acgcagtaca gcaaggtcct ggccctgtac  1020
aaccagcata cccggggcgc ctcggcggcg ccgtgctgcg tgccgcaggc gctggagccg  1080
ctgcccatcg tgtactacgt gggccgcaag cccaaggtgg agcagctgtc caacatgatc  1140
gtgcgctcct gcaagtgcag ctgatga                                       1167
```

<210> SEQ ID NO 3
<211> LENGTH: 387
<212> TYPE: PRT
<213> ORGANISM: Artificial Sequence
<220> FEATURE:
<223> OTHER INFORMATION: flag-tagged mouse latent TGF-beta 1

<400> SEQUENCE: 3

```
Met Lys Trp Val Thr Phe Leu Leu Leu Leu Phe Ile Ser Gly Ser Ala
1               5                   10                  15

Phe Ser Asp Tyr Lys Asp Asp Asp Lys Leu Ser Thr Ser Lys Thr
            20                  25                  30

Ile Asp Met Glu Leu Val Lys Arg Lys Arg Ile Glu Ala Ile Arg Gly
        35                  40                  45

Gln Ile Leu Ser Lys Leu Arg Leu Ala Ser Pro Ser Gln Gly Glu
    50                  55                  60

Val Pro Pro Gly Pro Leu Pro Glu Ala Val Leu Ala Leu Tyr Asn Ser
65                  70                  75                  80

Thr Arg Asp Arg Val Ala Gly Glu Ser Ala Asp Pro Glu Pro Glu Pro
                85                  90                  95

Glu Ala Asp Tyr Tyr Ala Lys Glu Val Thr Arg Val Leu Met Val Asp
            100                 105                 110

Arg Asn Asn Ala Ile Tyr Glu Lys Thr Lys Asp Ile Ser His Ser Ile
        115                 120                 125
```

Tyr Met Phe Asn Thr Ser Asp Ile Arg Glu Ala Val Pro Glu Pro
    130                 135                 140

Pro Leu Leu Ser Arg Ala Glu Leu Arg Leu Gln Arg Leu Lys Ser Ser
145                 150                 155                 160

Val Glu Gln His Val Glu Leu Tyr Gln Lys Tyr Ser Asn Asn Ser Trp
                165                 170                 175

Arg Tyr Leu Gly Asn Arg Leu Leu Thr Pro Thr Asp Thr Pro Glu Trp
            180                 185                 190

Leu Ser Phe Asp Val Thr Gly Val Val Arg Gln Trp Leu Asn Gln Gly
        195                 200                 205

Asp Gly Ile Gln Gly Phe Arg Phe Ser Ala His Cys Ser Cys Asp Ser
    210                 215                 220

Lys Asp Asn Lys Leu His Val Glu Ile Asn Gly Ile Ser Pro Lys Arg
225                 230                 235                 240

Arg Gly Asp Leu Gly Thr Ile His Asp Met Asn Arg Pro Phe Leu Leu
                245                 250                 255

Leu Met Ala Thr Pro Leu Glu Arg Ala Gln His Leu His Ser Ser Arg
            260                 265                 270

His Arg Arg Ala Leu Asp Thr Asn Tyr Cys Phe Ser Ser Thr Glu Lys
        275                 280                 285

Asn Cys Cys Val Arg Gln Leu Tyr Ile Asp Phe Arg Lys Asp Leu Gly
    290                 295                 300

Trp Lys Trp Ile His Glu Pro Lys Gly Tyr His Ala Asn Phe Cys Leu
305                 310                 315                 320

Gly Pro Cys Pro Tyr Ile Trp Ser Leu Asp Thr Gln Tyr Ser Lys Val
                325                 330                 335

Leu Ala Leu Tyr Asn Gln His Asn Pro Gly Ala Ser Ala Ser Pro Cys
            340                 345                 350

Cys Val Pro Gln Ala Leu Glu Pro Leu Pro Ile Val Tyr Tyr Val Gly
        355                 360                 365

Arg Lys Pro Lys Val Glu Gln Leu Ser Asn Met Ile Val Arg Ser Cys
    370                 375                 380

Lys Cys Ser
385

<210> SEQ ID NO 4
<211> LENGTH: 1167
<212> TYPE: DNA
<213> ORGANISM: Artificial Sequence
<220> FEATURE:
<223> OTHER INFORMATION: flag-tagged mouse latent TGF-beta 1

<400> SEQUENCE: 4
atgaagtggg taacctttct cctcctcctc ttcatctccg gttctgcctt ttccgactac    60
aaggatgacg atgacaagct ctccacctcc aagaccatcg acatggagct ggtgaaacgg    120
aagcgcatcg aagccatccg tggccagatc ctgtccaaac taaggctcgc cagtccccca    180 agccagggg aggtaccgcc cggcccgctg cccgaggcgg tgctcgcttt gtacaacagc    240
acccgcgacc gggtggcagg cgagagcgcc gacccagagc ggagcccga agcggactac    300 tatgctaaag aggtcacccg cgtgctaatg gtggaccgca caacgccat ctatgagaaa    360 accaaagaca tctcacacag tatatatatg ttcttcaata cgtcagacat tcgggaagca    420
gtgcccgaac ccccattgct gtcccgtgca gagctgcgct tgcagagatt aaaatcaagt    480
gtggagcaac atgtggaact ctaccagaaa tatagcaaca attcctggcg ttaccttggt    540

```
aaccggctgc tgacccccac tgatacgcct gagtggctgt cttttgacgt cactggagtt    600
gtacggcagt ggctgaacca aggagacgga atacagggct ttcgattcag cgctcactgc    660
tcttgtgaca gcaaagataa caaactccac gtggaaatca acgggatcag ccccaaacgt    720
cggggcgacc tgggcaccat ccatgacatg aaccggccct tcctgctcct catggccacc    780
cccctggaaa gggcccagca cctgcacagc tcacggcacc ggagagccct ggataccaac    840
tattgcttca gctccacaga gaagaactgc tgtgtgcggc agctgtacat tgactttagg    900
aaggacctgg gttggaagtg gatccacgag cccaagggct accatgccaa cttctgtctg    960
ggaccctgcc cctatatttg gagcctggac acacagtaca gcaaggtcct tgccctctac   1020
aaccaacaca cccgggcgc ttcggcgtca ccgtgctgcg tgccgcaggc tttggagcca   1080
ctgcccatcg tctactacgt gggtcgcaag cccaaggtgg agcagttgtc caacatgatt   1140
gtgcgctcct gcaagtgcag ctgatga                                      1167

<210> SEQ ID NO 5
<211> LENGTH: 387
<212> TYPE: PRT
<213> ORGANISM: Artificial Sequence
<220> FEATURE:
<223> OTHER INFORMATION: flag-tagged cynomolgus monkey latent TGF-beta 1

<400> SEQUENCE: 5

Met Lys Trp Val Thr Phe Leu Leu Leu Phe Ile Ser Gly Ser Ala
1               5                   10                  15

Phe Ser Asp Tyr Lys Asp Asp Asp Lys Leu Ser Thr Ser Lys Thr
            20                  25                  30

Ile Asp Met Glu Leu Val Lys Arg Lys Arg Ile Glu Ala Ile Arg Gly
        35                  40                  45

Gln Ile Leu Ser Lys Leu Arg Leu Ala Ser Pro Pro Ser Gln Gly Glu
    50                  55                  60

Val Pro Pro Gly Pro Leu Pro Glu Ala Val Leu Ala Leu Tyr Asn Ser
65                  70                  75                  80

Thr Arg Asp Arg Val Ala Gly Glu Ser Ala Glu Pro Glu Pro Glu Pro
                85                  90                  95

Glu Ala Asp Tyr Tyr Ala Lys Glu Val Thr Arg Val Leu Met Val Glu
            100                 105                 110

Thr His Asn Glu Ile Tyr Asp Lys Phe Lys Gln Ser Thr His Ser Ile
        115                 120                 125

Tyr Met Phe Phe Asn Thr Ser Glu Leu Arg Glu Ala Val Pro Glu Pro
    130                 135                 140

Val Leu Leu Ser Arg Ala Glu Leu Arg Leu Leu Arg Leu Lys Leu Lys
145                 150                 155                 160

Val Glu Gln His Val Glu Leu Tyr Gln Lys Tyr Ser Asn Asn Ser Trp
                165                 170                 175

Arg Tyr Leu Ser Asn Arg Leu Leu Ala Pro Ser Asp Ser Pro Glu Trp
            180                 185                 190

Leu Ser Phe Asp Val Thr Gly Val Val Arg Gln Trp Leu Ser Arg Gly
        195                 200                 205

Gly Glu Ile Glu Gly Phe Arg Leu Ser Ala His Cys Ser Cys Asp Ser
    210                 215                 220

Lys Asp Asn Thr Leu Gln Val Asp Ile Asn Gly Phe Thr Thr Gly Arg
225                 230                 235                 240

Arg Gly Asp Leu Ala Thr Ile His Gly Met Asn Arg Pro Phe Leu Leu
```

```
                     245                 250                 255
Leu Met Ala Thr Pro Leu Glu Arg Ala Gln His Leu Gln Ser Ser Arg
            260                 265                 270

His Arg Arg Ala Leu Asp Thr Asn Tyr Cys Phe Ser Ser Thr Glu Lys
            275                 280                 285

Asn Cys Cys Val Arg Gln Leu Tyr Ile Asp Phe Arg Lys Asp Leu Gly
            290                 295                 300

Trp Lys Trp Ile His Glu Pro Lys Gly Tyr His Ala Asn Phe Cys Leu
305                 310                 315                 320

Gly Pro Cys Pro Tyr Ile Trp Ser Leu Asp Thr Gln Tyr Ser Lys Val
                325                 330                 335

Leu Ala Leu Tyr Asn Gln His Asn Pro Gly Ala Ser Ala Ala Pro Cys
            340                 345                 350

Cys Val Pro Gln Ala Leu Glu Pro Leu Pro Ile Val Tyr Tyr Val Gly
            355                 360                 365

Arg Lys Pro Lys Val Glu Gln Leu Ser Asn Met Ile Val Arg Ser Cys
            370                 375                 380

Lys Cys Ser
385

<210> SEQ ID NO 6
<211> LENGTH: 1167
<212> TYPE: DNA
<213> ORGANISM: Artificial Sequence
<220> FEATURE:
<223> OTHER INFORMATION: flag-tagged cynomolgus monkey latent TGF-beta 1

<400> SEQUENCE: 6
atgaagtggg taacctttct cctcctcctc ttcatctccg ttctgccctt ttccgactac     60
aaggatgacg atgacaagct atccacctcc aagactatcg acatggagct ggtgaagcgg    120
aagcgcatcg aggccatccg cggccagatc ctgtccaagc tgcggctcgc cagccccccg    180
agccaggggg aggtgccgcc cggcccgctg cccgaggccg tgctcgccct gtacaacagc    240
acccgcgacc gggtggccgg ggagagtgca gaaccggagc ccgagcctga ggccgactac    300
tacgccaagg aggtcacccg cgtgctaatg gtggaaaccc acaacgaaat ctatgacaag    360
ttcaagcaga gtacacacag catatatatg ttcttcaaca catcagagct ccgagaagcg    420
gtacctgaac ccgtgttgct ctcccgggca gagctgcgtc tgctgaggct caagttaaaa    480
gtggagcagc acgtggagct gtaccagaaa tacagcaaca attcctggcg ataccctcagc    540 aaccggctgc tggcacccag cgactcgcca gagtggttat cttttgatgt caccggagtt    600
gtgcggcagt ggttgagccg tggagggaa attgagggct ttcgccttag cgcccactgc    660
tcctgtgaca gcaaggataa cacactgcaa gtggacatca acgggttcac taccggccgc    720
cgaggtgacc tggccaccat tcatggcatg aaccggcctt tcctgcttct catggccacc    780
ccgctggaga gggcccagca tctgcaaagc tcccggcacc gccgagccct ggacaccaac    840
tattgcttca gctccacgga gaagaactgc tgcgtgcggc agctgtacat tgacttccgc    900
aaggacctcg gctggaagtg gatccacgag cccaagggct accatgccaa cttctgcctc    960
gggccctgcc cctacatttg gagcctggac acgcagtaca gcaaggtcct ggccctgtac   1020
aaccagcata accgggcgc ctcggcggcg ccgtgctgcg tgccgcaggc gctggagccg   1080
ctgcccatcg tgtactacgt gggccgcaag cccaaggtgg agcagctgtc caacatgatc   1140
gtgcgctcct gcaagtgcag ctgatga                                      1167
```

<210> SEQ ID NO 7
<211> LENGTH: 1824
<212> TYPE: DNA
<213> ORGANISM: Rattus norvegicus

<400> SEQUENCE: 7

```
atgaagtggg taacctttct cctcctcctc ttcatctccg gttctgcctt ttccaggggt      60
gtgtttcgcc gagaagcaca caagagtgag atcgcccatc ggtttaagga cttgggagaa     120
cagcatttca aaggcctagt cctgattgcc ttttcccagt atctccagaa atgcccatat     180
gaagagcata tcaaattggt gcaggaagta acagactttg caaaaacatg tgtcgctgat     240
gagaatgccg aaaactgtga caagtccatt cacactctct cggagacaa gttatgcgcc      300
attccaaagc ttcgcgacaa ctacggtgaa ctggctgact gctgtgcaaa caagagccc      360
gaaagaaacg agtgtttcct gcagcacaag gatgacaacc ccaacctgcc acccttccag     420
aggccggagg ctgaggccat gtgcacctcc ttccaggaga accctaccag ctttctggga     480
cactatttgc atgaagttgc caggagacat ccttatttct atgccccaga actccttac      540
tatgctgaga atacaatga ggttctgacc cagtgctgca cagagtctga caaagcagcc      600
tgcctgacac cgaagcttga tgccgtgaaa gagaaagcac tggtcgcagc tgtccgtcag     660
aggatgaagt gctccagtat gcagagattt ggagagagag ccttcaaagc ctgggcagta     720
gctcgtatga ccagcgatt ccccaatgct gagttcgcag aaatcaccaa attggcaaca      780
gacctcacca aaatcaacaa ggagtgctgt cacggcgacc tgttggaatg cgcggatgac     840
agggcggaac ttgccaagta catgtgtgag aaccaggcca ctatctccag caaactgcag     900
gcttgctgtg ataagccagt gctgcagaaa tcccagtgtc tcgctgagat agaacatgac     960
aacattcctg ccgatctgcc ctcaatagct gctgactttg ttgaggataa ggaagtgtgt    1020
aagaactatg ctgaggccaa ggatgtcttc ctgggcacgt ttttgtatga atattcaaga    1080
aggcaccccg attactccgt gtccctgctg ctgagacttg ctaagaaata tgaagccaca    1140
ctggagaagt gctgtgctga aggcgatcct cctgcctgct acggcacagt gcttgcagaa    1200
tttcagcctc ttgtagaaga acctaagaac ttggtcaaaa ctaactgtga gctttacgag    1260
aagcttggag agtatggatt ccaaaacgcc attctggttc gatacaccca gaaagcacct    1320
caggtgtcga ccccaactct cgtggaggca gcaagaaacc tgggaagagt gggcaccaag    1380
tgttgtaccc ttcctgaagc tcagagactg ccctgtgtgg aagactatct gtctgccatc    1440
ctgaaccgtc tgtgtgtgct gcatgagaag accccagtga gcgagaaggt caccaagtgc    1500
tgtagtgggt ccctggtgga aagacggcca tgtttctctg ctctgacagt tgacgagaca    1560
tatgtccccc aagagtttaa agctgagacc ttcaccttcc actctgatat ctgcacactc    1620
ccagacaagg agaagcagat aaagaagcaa acggctctcg ctgagctggt gaaacacaag    1680
cccaaggcca cagaagatca gctgaagacg gtgatgggtg acttcgcaca attcgtggac    1740
aagtgttgca aggctgccga caaggataac tgcttcgcca ctgaggggcc aaaccttgtt    1800
gctagaagca agaagccctt agcc                                           1824
```

<210> SEQ ID NO 8
<211> LENGTH: 275
<212> TYPE: PRT
<213> ORGANISM: Artificial Sequence
<220> FEATURE:
<223> OTHER INFORMATION: flag-tagged mouse LAP

<400> SEQUENCE: 8

Met Lys Trp Val Thr Phe Leu Leu Leu Phe Ile Ser Gly Ser Ala
1               5                   10                  15

Phe Ser Asp Tyr Lys Asp Asp Asp Lys Leu Ser Thr Ser Lys Thr
                20                  25                  30

Ile Asp Met Glu Leu Val Lys Arg Lys Arg Ile Glu Ala Ile Arg Gly
            35                  40                  45

Gln Ile Leu Ser Lys Leu Arg Leu Ala Ser Pro Pro Ser Gln Gly Glu
            50                  55                  60

Val Pro Pro Gly Pro Leu Pro Glu Ala Val Leu Ala Leu Tyr Asn Ser
65              70                  75                  80

Thr Arg Asp Arg Val Ala Gly Glu Ser Ala Asp Pro Glu Pro Glu Pro
                85                  90                  95

Glu Ala Asp Tyr Tyr Ala Lys Glu Val Thr Arg Val Leu Met Val Asp
                100                 105                 110

Arg Asn Asn Ala Ile Tyr Glu Lys Thr Lys Asp Ile Ser His Ser Ile
            115                 120                 125

Tyr Met Phe Phe Asn Thr Ser Asp Ile Arg Glu Ala Val Pro Glu Pro
    130                 135                 140

Pro Leu Leu Ser Arg Ala Glu Leu Arg Leu Gln Arg Leu Lys Ser Ser
145                 150                 155                 160

Val Glu Gln His Val Glu Leu Tyr Gln Lys Tyr Ser Asn Asn Ser Trp
                165                 170                 175

Arg Tyr Leu Gly Asn Arg Leu Leu Thr Pro Thr Asp Thr Pro Glu Trp
            180                 185                 190

Leu Ser Phe Asp Val Thr Gly Val Val Arg Gln Trp Leu Asn Gln Gly
            195                 200                 205

Asp Gly Ile Gln Gly Phe Arg Phe Ser Ala His Cys Ser Cys Asp Ser
    210                 215                 220

Lys Asp Asn Lys Leu His Val Glu Ile Asn Gly Ile Ser Pro Lys Arg
225                 230                 235                 240

Arg Gly Asp Leu Gly Thr Ile His Asp Met Asn Arg Pro Phe Leu Leu
            245                 250                 255

Leu Met Ala Thr Pro Leu Glu Arg Ala Gln His Leu His Ser Ser Arg
            260                 265                 270

His Arg Arg
        275

<210> SEQ ID NO 9
<211> LENGTH: 831
<212> TYPE: DNA
<213> ORGANISM: Artificial Sequence
<220> FEATURE:
<223> OTHER INFORMATION: flag-tagged mouse LAP

<400> SEQUENCE: 9
atgaagtggg taacctttct cctcctcctc ttcatctccg gttctgcctt ttccgactac    60
aaggatgacg atgacaagct ctccacctcc aagaccatcg acatggagct ggtgaaacgg   120
aagcgcatcg aagccatccg tggccagatc ctgtccaaac taaggctcgc cagtccccca   180
agccaggggg aggtaccgcc cggcccgctg cccgaggcgg tgctcgcttt gtacaacagc   240
acccgcgacc gggtggcagg cgagagcgcc gacccagagc cggagcccga agcggactac   300
tatgctaaag aggtcacccg cgtgctaatg gtggaccgca acaacgccat ctatgagaaa   360
accaaagaca tctcacacag tatatatatg ttcttcaata cgtcagacat tcgggaagca   420

```
gtgcccgaac ccccattgct gtcccgtgca gagctgcgct tgcagagatt aaaatcaagt    480
gtggagcaac atgtggaact ctaccagaaa tatagcaaca attcctggcg ttaccttggt    540
aaccggctgc tgaccccccac tgatacgcct gagtggctgt cttttgacgt cactggagtt   600
gtacggcagt ggctgaacca aggagacgga atacagggct ttcgattcag cgctcactgc    660
tcttgtgaca gcaaagataa caaactccac gtggaaatca acgggatcag ccccaaacgt    720
cggggcgacc tgggcaccat ccatgacatg aaccggccct tcctgctcct catggccacc    780
cccctggaaa gggcccagca cctgcacagc tcacggcacc ggagatgatg a             831
```

<210> SEQ ID NO 10
<211> LENGTH: 328
<212> TYPE: PRT
<213> ORGANISM: Artificial Sequence
<220> FEATURE:
<223> OTHER INFORMATION: SG181

<400> SEQUENCE: 10

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Arg Arg Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
```

```
                    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 11
<211> LENGTH: 107
<212> TYPE: PRT
<213> ORGANISM: Homo sapiens

<400> SEQUENCE: 11

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 12
<211> LENGTH: 122
<212> TYPE: PRT
<213> ORGANISM: Artificial Sequence
<220> FEATURE:
<223> OTHER INFORMATION: hT0947AE04H VH

<400> SEQUENCE: 12

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Asn Trp Ile Arg Gln Pro Pro Gly Lys Gly Leu Glu Trp Ile
        35                  40                  45

Gly Tyr Ile Tyr Thr Ser Gly Thr Thr Tyr His Ala Asn Trp Ala Arg
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Thr Phe Ile Trp Asp Tyr Tyr Tyr Trp Val Met Asp Leu Trp
            100                 105                 110

Gly Pro Gly Thr Leu Val Thr Val Ser Ser
        115                 120

<210> SEQ ID NO 13
<211> LENGTH: 108
<212> TYPE: PRT
<213> ORGANISM: Artificial Sequence
<220> FEATURE:
<223> OTHER INFORMATION: hT0947AE04L VL
```

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Tyr
            20                  25                  30

Leu Ala Trp Tyr Gln Gln Lys Pro Gly Gln Pro Pro Lys Leu Leu Ile
        35                  40                  45

Tyr Lys Ala Ser Thr Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Tyr Ser Asp Ala Asp Ser
                85                  90                  95

Val Gly Phe Gly Gln Gly Thr Lys Val Glu Ile Lys
            100                 105

<210> SEQ ID NO 14
<211> LENGTH: 122
<212> TYPE: PRT
<213> ORGANISM: Artificial Sequence
<220> FEATURE:
<223> OTHER INFORMATION: hT0947AE07H VH

<400> SEQUENCE: 14

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Glu
            20                  25                  30

Ala Met Asn Trp Ile Arg Gln Pro Pro Gly Lys Gly Leu Glu Trp Ile
        35                  40                  45

Gly Tyr Ile Tyr Thr Ser Gly Thr Thr Tyr Arg Ala Asn Trp Ala Arg
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Thr Gly Ile Tyr Asp Tyr Tyr Tyr Trp Val Met Asp Leu Trp
            100                 105                 110

Gly Pro Gly Thr Leu Val Thr Val Ser Ser
        115                 120

<210> SEQ ID NO 15
<211> LENGTH: 108
<212> TYPE: PRT
<213> ORGANISM: Artificial Sequence
<220> FEATURE:
<223> OTHER INFORMATION: hT0947AE07L VL

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Tyr
            20                  25                  30

Leu Ala Trp Tyr Gln Gln Lys Pro Gly Gln Pro Pro Lys Leu Leu Ile
        35                  40                  45

Tyr Ala Ala Ser Thr Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Tyr Ser Asp Gly Asp Ser
                85                  90                  95

Val Gly Phe Gly Gln Gly Thr Lys Val Glu Ile Lys
            100                 105

<210> SEQ ID NO 16
<211> LENGTH: 122
<212> TYPE: PRT
<213> ORGANISM: Artificial Sequence
<220> FEATURE:
<223> OTHER INFORMATION: hT0947AE08H VH

<400> SEQUENCE: 16

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met Asn Trp Ile Arg Gln Pro Pro Gly Lys Gly Leu Glu Trp Ile
            35                  40                  45

Gly Tyr Ile Tyr Thr Ser Gly Thr Arg Tyr Arg Ala Asn Trp Ala Arg
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Thr Asp Ile Tyr Asp Tyr Tyr Trp Val Met Asp Leu Trp
            100                 105                 110

Gly Pro Gly Thr Leu Val Thr Val Ser Ser
            115                 120

<210> SEQ ID NO 17
<211> LENGTH: 108
<212> TYPE: PRT
<213> ORGANISM: Artificial Sequence
<220> FEATURE:
<223> OTHER INFORMATION: hT0947AE08L VL

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Tyr
                20                  25                  30

Leu Ala Trp Tyr Gln Gln Lys Pro Gly Gln Pro Pro Lys Leu Leu Ile
            35                  40                  45

Tyr Ala Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Tyr Ser Asp Gly Asp Ser
                85                  90                  95

Val Gly Phe Gly Gln Gly Thr Lys Val Glu Ile Lys
            100                 105

<210> SEQ ID NO 18
<211> LENGTH: 122
<212> TYPE: PRT
<213> ORGANISM: Artificial Sequence

```
<220> FEATURE:
<223> OTHER INFORMATION: hT0947AE09H VH

<400> SEQUENCE: 18

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Asn Trp Ile Arg Gln Pro Pro Gly Lys Gly Leu Glu Trp Ile
        35                  40                  45

Gly Tyr Ile Tyr Thr Ser Gly Thr Arg Tyr Arg Ala Asn Trp Ala Arg
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Thr Asp Ile Tyr Asp Tyr Tyr Tyr Trp Val Met Asp Leu Trp
            100                 105                 110

Gly Pro Gly Thr Leu Val Thr Val Ser Ser
        115                 120

<210> SEQ ID NO 19
<211> LENGTH: 108
<212> TYPE: PRT
<213> ORGANISM: Artificial Sequence
<220> FEATURE:
<223> OTHER INFORMATION: hT0947AE09L VL

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Tyr
            20                  25                  30

Leu Ala Trp Tyr Gln Gln Lys Pro Gly Gln Pro Pro Lys Leu Leu Ile
        35                  40                  45

Tyr Ala Ala Ser Thr Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Tyr Ser Asp Ala Asp Ser
                85                  90                  95

Val Gly Phe Gly Gln Gly Thr Lys Val Glu Ile Lys
            100                 105

<210> SEQ ID NO 20
<211> LENGTH: 5
<212> TYPE: PRT
<213> ORGANISM: Artificial Sequence
<220> FEATURE:
<223> OTHER INFORMATION: hT0947AE04H HVR-H1

<400> SEQUENCE: 20

Ser Tyr Ala Met Asn
1               5

<210> SEQ ID NO 21
<211> LENGTH: 16
<212> TYPE: PRT
<213> ORGANISM: Artificial Sequence
<220> FEATURE:
```

<223> OTHER INFORMATION: hT0947AE04H HVR-H2

<400> SEQUENCE: 21

Tyr Ile Tyr Thr Ser Gly Thr Thr Tyr His Ala Asn Trp Ala Arg Gly
1               5                   10                  15

<210> SEQ ID NO 22
<211> LENGTH: 14
<212> TYPE: PRT
<213> ORGANISM: Artificial Sequence
<220> FEATURE:
<223> OTHER INFORMATION: hT0947AE04H HVR-H3

<400> SEQUENCE: 22

Gly Thr Phe Ile Trp Asp Tyr Tyr Tyr Trp Val Met Asp Leu
1               5                   10

<210> SEQ ID NO 23
<211> LENGTH: 11
<212> TYPE: PRT
<213> ORGANISM: Artificial Sequence
<220> FEATURE:
<223> OTHER INFORMATION: hT0947AE04L HVR-L1

<400> SEQUENCE: 23

Gln Ala Ser Gln Ser Ile Ser Thr Tyr Leu Ala
1               5                   10

<210> SEQ ID NO 24
<211> LENGTH: 7
<212> TYPE: PRT
<213> ORGANISM: Artificial Sequence
<220> FEATURE:
<223> OTHER INFORMATION: hT0947AE04L HVR-L2

<400> SEQUENCE: 24

Lys Ala Ser Thr Leu Glu Ser
1               5

<210> SEQ ID NO 25
<211> LENGTH: 10
<212> TYPE: PRT
<213> ORGANISM: Artificial Sequence
<220> FEATURE:
<223> OTHER INFORMATION: hT0947AE04L HVR-L3

<400> SEQUENCE: 25

Gln Ser Tyr Ser Asp Ala Asp Ser Val Gly
1               5                   10

<210> SEQ ID NO 26
<211> LENGTH: 5
<212> TYPE: PRT
<213> ORGANISM: Artificial Sequence
<220> FEATURE:
<223> OTHER INFORMATION: hT0947AE07H HVR-H1

<400> SEQUENCE: 26

Ser Glu Ala Met Asn
1               5

<210> SEQ ID NO 27
<211> LENGTH: 16
<212> TYPE: PRT
<213> ORGANISM: Artificial Sequence
<220> FEATURE:
<223> OTHER INFORMATION: hT0947AE07H HVR-H2

```
<400> SEQUENCE: 27

Tyr Ile Tyr Thr Ser Gly Thr Thr Tyr Arg Ala Asn Trp Ala Arg Gly
1               5                   10                  15

<210> SEQ ID NO 28
<211> LENGTH: 14
<212> TYPE: PRT
<213> ORGANISM: Artificial Sequence
<220> FEATURE:
<223> OTHER INFORMATION: hT0947AE07H HVR-H3

<400> SEQUENCE: 28

Gly Thr Gly Ile Tyr Asp Tyr Tyr Tyr Trp Val Met Asp Leu
1               5                   10

<210> SEQ ID NO 29
<211> LENGTH: 11
<212> TYPE: PRT
<213> ORGANISM: Artificial Sequence
<220> FEATURE:
<223> OTHER INFORMATION: hT0947AE07L HVR-L1

<400> SEQUENCE: 29

Gln Ala Ser Gln Ser Ile Ser Thr Tyr Leu Ala
1               5                   10

<210> SEQ ID NO 30
<211> LENGTH: 7
<212> TYPE: PRT
<213> ORGANISM: Artificial Sequence
<220> FEATURE:
<223> OTHER INFORMATION: hT0947AE07L HVR-L2

<400> SEQUENCE: 30

Ala Ala Ser Thr Leu Glu Ser
1               5

<210> SEQ ID NO 31
<211> LENGTH: 10
<212> TYPE: PRT
<213> ORGANISM: Artificial Sequence
<220> FEATURE:
<223> OTHER INFORMATION: hT0947AE07L HVR-L3

<400> SEQUENCE: 31

Gln Ser Tyr Ser Asp Gly Asp Ser Val Gly
1               5                   10

<210> SEQ ID NO 32
<211> LENGTH: 5
<212> TYPE: PRT
<213> ORGANISM: Artificial Sequence
<220> FEATURE:
<223> OTHER INFORMATION: hT0947AE08H HVR-H1

<400> SEQUENCE: 32

Ser Tyr Ala Met Asn
1               5

<210> SEQ ID NO 33
<211> LENGTH: 16
<212> TYPE: PRT
<213> ORGANISM: Artificial Sequence
<220> FEATURE:
<223> OTHER INFORMATION: hT0947AE08H HVR-H2
```

```
<400> SEQUENCE: 33

Tyr Ile Tyr Thr Ser Gly Thr Arg Tyr Arg Ala Asn Trp Ala Arg Gly
1               5                   10                  15

<210> SEQ ID NO 34
<211> LENGTH: 14
<212> TYPE: PRT
<213> ORGANISM: Artificial Sequence
<220> FEATURE:
<223> OTHER INFORMATION: hT0947AE08H HVR-H3

<400> SEQUENCE: 34

Gly Thr Asp Ile Tyr Asp Tyr Tyr Tyr Trp Val Met Asp Leu
1               5                   10

<210> SEQ ID NO 35
<211> LENGTH: 11
<212> TYPE: PRT
<213> ORGANISM: Artificial Sequence
<220> FEATURE:
<223> OTHER INFORMATION: hT0947AE08L HVR-L1

<400> SEQUENCE: 35

Gln Ala Ser Gln Ser Ile Ser Thr Tyr Leu Ala
1               5                   10

<210> SEQ ID NO 36
<211> LENGTH: 7
<212> TYPE: PRT
<213> ORGANISM: Artificial Sequence
<220> FEATURE:
<223> OTHER INFORMATION: hT0947AE08L HVR-L2

<400> SEQUENCE: 36

Ala Ala Ser Thr Leu Glu Ser
1               5

<210> SEQ ID NO 37
<211> LENGTH: 10
<212> TYPE: PRT
<213> ORGANISM: Artificial Sequence
<220> FEATURE:
<223> OTHER INFORMATION: hT0947AE08L HVR-L3

<400> SEQUENCE: 37

Gln Ser Tyr Ser Asp Gly Asp Ser Val Gly
1               5                   10

<210> SEQ ID NO 38
<211> LENGTH: 5
<212> TYPE: PRT
<213> ORGANISM: Artificial Sequence
<220> FEATURE:
<223> OTHER INFORMATION: hT0947AE09H HVR-H1

<400> SEQUENCE: 38

Ser Tyr Ala Met Asn
1               5

<210> SEQ ID NO 39
<211> LENGTH: 16
<212> TYPE: PRT
<213> ORGANISM: Artificial Sequence
<220> FEATURE:
<223> OTHER INFORMATION: hT0947AE09H HVR-H2

<400> SEQUENCE: 39
```

Tyr Ile Tyr Thr Ser Gly Thr Arg Tyr Arg Ala Asn Trp Ala Arg Gly
1               5                   10                  15

<210> SEQ ID NO 40
<211> LENGTH: 14
<212> TYPE: PRT
<213> ORGANISM: Artificial Sequence
<220> FEATURE:
<223> OTHER INFORMATION: hT0947AE09H HVR-H3

<400> SEQUENCE: 40

Gly Thr Asp Ile Tyr Asp Tyr Tyr Trp Val Met Asp Leu
1               5                   10

<210> SEQ ID NO 41
<211> LENGTH: 11
<212> TYPE: PRT
<213> ORGANISM: Artificial Sequence
<220> FEATURE:
<223> OTHER INFORMATION: hT0947AE09L HVR-L1

<400> SEQUENCE: 41

Gln Ala Ser Gln Ser Ile Ser Thr Tyr Leu Ala
1               5                   10

<210> SEQ ID NO 42
<211> LENGTH: 7
<212> TYPE: PRT
<213> ORGANISM: Artificial Sequence
<220> FEATURE:
<223> OTHER INFORMATION: hT0947AE09L HVR-L2

<400> SEQUENCE: 42

Ala Ala Ser Thr Leu Glu Ser
1               5

<210> SEQ ID NO 43
<211> LENGTH: 10
<212> TYPE: PRT
<213> ORGANISM: Artificial Sequence
<220> FEATURE:
<223> OTHER INFORMATION: hT0947AE09L HVR-L3

<400> SEQUENCE: 43

Gln Ser Tyr Ser Asp Ala Asp Ser Val Gly
1               5                   10

<210> SEQ ID NO 44
<211> LENGTH: 328
<212> TYPE: PRT
<213> ORGANISM: Artificial Sequence
<220> FEATURE:
<223> OTHER INFORMATION: SG1

<400> SEQUENCE: 44

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr

```
                65                  70                  75                  80
Tyr Ile Cys Asn Val Asn His Lys Pro Ser Asn Thr Lys Val Asp Lys
                    85                  90                  95
Lys Val Glu Pro Lys Ser Cys Asp Lys Thr His Thr Cys Pro Pro Cys
                100                 105                 110
Pro Ala Pro Glu Leu Leu Gly Gly Pro Ser Val Phe Leu Phe Pro Pro
                115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
                180                 185                 190
His Gln Asp Trp Leu Asn Gly Lys Glu Tyr Lys Cys Lys Val Ser Asn
                195                 200                 205
Lys Ala Leu Pro Ala Pro Ile Glu Lys Thr Ile Ser Lys Ala Lys Gly
                210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
                260                 265                 270
Asn Tyr Lys Thr Thr Pro Pro Val Leu Asp Ser Asp Gly Ser Phe Phe
                275                 280                 285
Leu Tyr Ser Lys Leu Thr Val Asp Lys Ser Arg Trp Gln Gln Gly Asn
                290                 295                 300
Val Phe Ser Cys Ser Val Met His Glu Ala Leu His Asn His Tyr Thr
305                 310                 315                 320
Gln Lys Ser Leu Ser Leu Ser Pro
                325

<210> SEQ ID NO 45
<211> LENGTH: 328
<212> TYPE: PRT
<213> ORGANISM: Artificial Sequence
<220> FEATURE:
<223> OTHER INFORMATION: SG191

<400> SEQUENCE: 45

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
                35                  40                  45
Gly Val His Thr Phe Pro Ala Val Leu Gln Ser Ser Gly Leu Tyr Ser
                50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Arg Val Glu Pro Lys Ser Cys Asp Lys Thr His Thr Cys Pro Pro Cys
```

```
                100                 105                 110
Pro Ala Pro Glu Leu Arg Arg Gly Pro Ser Val Phe Leu Phe Pro Pro
            115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Leu His Glu Ala Leu His Ala His Tyr Thr
305                 310                 315                 320
Arg Lys Glu Leu Ser Leu Ser Pro
                325

<210> SEQ ID NO 46
<211> LENGTH: 324
<212> TYPE: PRT
<213> ORGANISM: Artificial Sequence
<220> FEATURE:
<223> OTHER INFORMATION: mF18

<400> SEQUENCE: 46

Ala Lys Thr Thr Pro Pro Ser Val Tyr Pro Leu Ala Pro Gly Ser Ala
1               5                   10                  15
Ala Gln Thr Asn Ser Met Val Thr Leu Gly Cys Leu Val Lys Gly Tyr
            20                  25                  30
Phe Pro Glu Pro Val Thr Val Thr Trp Asn Ser Gly Ser Leu Ser Ser
        35                  40                  45
Gly Val His Thr Phe Pro Ala Val Leu Gln Ser Asp Leu Tyr Thr Leu
    50                  55                  60
Ser Ser Ser Val Thr Val Pro Ser Ser Thr Trp Pro Ser Glu Thr Val
65                  70                  75                  80
Thr Cys Asn Val Ala His Pro Ala Ser Ser Thr Lys Val Asp Lys Lys
                85                  90                  95
Ile Val Pro Arg Asp Cys Gly Cys Lys Pro Cys Ile Cys Thr Val Lys
            100                 105                 110
Glu Val Ser Lys Val Phe Ile Phe Pro Pro Lys Pro Lys Asp Val Leu
        115                 120                 125
Thr Ile Thr Leu Thr Pro Lys Val Thr Cys Val Val Val Asp Ile Ser
```

```
            130                 135                 140
Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 47
<211> LENGTH: 450
<212> TYPE: PRT
<213> ORGANISM: Artificial Sequence
<220> FEATURE:
<223> OTHER INFORMATION: hT0947AE04H-SG181

<400> SEQUENCE: 47

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Asn Trp Ile Arg Gln Pro Pro Gly Lys Gly Leu Glu Trp Ile
        35                  40                  45

Gly Tyr Ile Tyr Thr Ser Gly Thr Thr Tyr His Ala Asn Trp Ala Arg
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Thr Phe Ile Trp Asp Tyr Tyr Tyr Trp Val Met Asp Leu Trp
            100                 105                 110

Gly Pro Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175
```

-continued

```
Ala Val Leu Gln Ser Ser Gly Leu Tyr Ser Leu Ser Ser Val Val Thr
            180                 185                 190

Val Pro Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
210                 215                 220

Cys Asp Lys Thr His Thr Cys Pro Pro Cys Pro Ala Pro Glu Leu Arg
225                 230                 235                 240

Arg Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro
    450

<210> SEQ ID NO 48
<211> LENGTH: 450
<212> TYPE: PRT
<213> ORGANISM: Artificial Sequence
<220> FEATURE:
<223> OTHER INFORMATION: hT0947AE07H-SG181

<400> SEQUENCE: 48

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Glu
            20                  25                  30

Ala Met Asn Trp Ile Arg Gln Pro Pro Gly Lys Gly Leu Glu Trp Ile
        35                  40                  45

Gly Tyr Ile Tyr Thr Ser Gly Thr Thr Tyr Arg Ala Asn Trp Ala Arg
    50                  55                  60

Gly Arg Phe Thr Ile Ser Arg Asp Asn Ser Lys Asn Thr Leu Tyr Leu
65                  70                  75                  80
```

```
Gln Met Asn Ser Leu Arg Ala Glu Asp Thr Ala Val Tyr Tyr Cys Ala
                85                  90                  95

Arg Gly Thr Gly Ile Tyr Asp Tyr Tyr Trp Val Met Asp Leu Trp
            100                 105                 110

Gly Pro Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Arg
225                 230                 235                 240

Arg Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro
    450

<210> SEQ ID NO 49
<211> LENGTH: 450
<212> TYPE: PRT
<213> ORGANISM: Artificial Sequence
<220> FEATURE:
```

<223> OTHER INFORMATION: hT0947AE08H-SG181

<400> SEQUENCE: 49

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Asn Trp Ile Arg Gln Pro Pro Gly Lys Gly Leu Glu Trp Ile
        35                  40                  45

Gly Tyr Ile Tyr Thr Ser Gly Thr Arg Tyr Arg Ala Asn Trp Ala Arg
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Thr Asp Ile Tyr Asp Tyr Tyr Tyr Trp Val Met Asp Leu Trp
            100                 105                 110

Gly Pro Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Arg
225                 230                 235                 240

Arg Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400
```

-continued

```
Pro Val Leu Asp Ser Asp Gly Ser Phe Phe Leu Tyr Ser Lys Leu Thr
                    405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
Ser Pro
    450

<210> SEQ ID NO 50
<211> LENGTH: 450
<212> TYPE: PRT
<213> ORGANISM: Artificial Sequence
<220> FEATURE:
<223> OTHER INFORMATION: hT0947AE09H-SG181

<400> SEQUENCE: 50

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Ala Met Asn Trp Ile Arg Gln Pro Pro Gly Lys Gly Leu Glu Trp Ile
        35                  40                  45
Gly Tyr Ile Tyr Thr Ser Gly Thr Arg Tyr Arg Ala Asn Trp Ala Arg
    50                  55                  60
Gly Arg Phe Thr Ile Ser Arg Asp Asn Ser Lys Asn Thr Leu Tyr Leu
65                  70                  75                  80
Gln Met Asn Ser Leu Arg Ala Glu Asp Thr Ala Val Tyr Tyr Cys Ala
                85                  90                  95
Arg Gly Thr Asp Ile Tyr Asp Tyr Tyr Tyr Trp Val Met Asp Leu Trp
            100                 105                 110
Gly Pro Gly Thr Leu Val Thr Val Ser Ser Ala Ser Thr Lys Gly Pro
        115                 120                 125
Ser Val Phe Pro Leu Ala Pro Ser Ser Lys Ser Thr Ser Gly Gly Thr
    130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
        195                 200                 205
His Lys Pro Ser Asn Thr Lys Val Asp Lys Arg Val Glu Pro Lys Ser
    210                 215                 220
Cys Asp Lys Thr His Thr Cys Pro Pro Cys Pro Ala Pro Glu Leu Arg
225                 230                 235                 240
Arg Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
    290                 295                 300
```

```
Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Pro
    450

<210> SEQ ID NO 51
<211> LENGTH: 450
<212> TYPE: PRT
<213> ORGANISM: Artificial Sequence
<220> FEATURE:
<223> OTHER INFORMATION: hT0947AE04H-SG191

<400> SEQUENCE: 51

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Asn Trp Ile Arg Gln Pro Pro Gly Lys Gly Leu Glu Trp Ile
        35                  40                  45

Gly Tyr Ile Tyr Thr Ser Gly Thr Thr Tyr His Ala Asn Trp Ala Arg
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Gly Thr Phe Ile Trp Asp Tyr Tyr Tyr Trp Val Met Asp Leu Trp
        100                 105                 110

Gly Pro Gly Thr Leu Val Thr Val Ser Ser Ala Ser Thr Lys Gly Pro
    115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Ser Leu Gly Thr Gln Thr Tyr Ile Cys Asn Val Asn
    195                 200                 205
```

His Lys Pro Ser Asn Thr Lys Val Asp Lys Arg Val Glu Pro Lys Ser
        210                 215                 220
Cys Asp Lys Thr His Thr Cys Pro Pro Cys Pro Ala Pro Glu Leu Arg
225                 230                 235                 240
Arg Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Glu Glu Met Thr Lys Asn Gln Val
        355                 360                 365
Ser Leu Thr Cys Leu Val Lys Gly Phe Tyr Pro Ser Asp Ile Ala Val
370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Leu His Glu Ala Leu His Ala His Tyr Thr Arg Lys Glu Leu Ser Leu
        435                 440                 445
Ser Pro
    450

<210> SEQ ID NO 52
<211> LENGTH: 450
<212> TYPE: PRT
<213> ORGANISM: Artificial Sequence
<220> FEATURE:
<223> OTHER INFORMATION: hT0947AE07H-SG191

<400> SEQUENCE: 52

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Glu
            20                  25                  30
Ala Met Asn Trp Ile Arg Gln Pro Pro Gly Lys Gly Leu Glu Trp Ile
        35                  40                  45
Gly Tyr Ile Tyr Thr Ser Gly Thr Thr Tyr Arg Ala Asn Trp Ala Arg
    50                  55                  60
Gly Arg Phe Thr Ile Ser Arg Asp Asn Ser Lys Asn Thr Leu Tyr Leu
65                  70                  75                  80
Gln Met Asn Ser Leu Arg Ala Glu Asp Thr Ala Val Tyr Tyr Cys Ala
                85                  90                  95
Arg Gly Thr Gly Ile Tyr Asp Tyr Tyr Tyr Trp Val Met Asp Leu Trp
            100                 105                 110

```
Gly Pro Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Arg
225                 230                 235                 240

Arg Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Leu His Glu Ala Leu His Ala His Tyr Thr Arg Lys Glu Leu Ser Leu
        435                 440                 445

Ser Pro
    450

<210> SEQ ID NO 53
<211> LENGTH: 450
<212> TYPE: PRT
<213> ORGANISM: Artificial Sequence
<220> FEATURE:
<223> OTHER INFORMATION: hT0947AE08H-SG191

<400> SEQUENCE: 53

Gln Val Gln Leu Val Glu Ser Gly Gly Gly Val Val Gln Pro Gly Arg
1               5                   10                  15
```

-continued

```
Ser Leu Arg Leu Ser Cys Ala Ala Ser Gly Phe Thr Phe Ser Ser Tyr
         20                  25                  30

Ala Met Asn Trp Ile Arg Gln Pro Gly Lys Gly Leu Glu Trp Ile
         35                  40                  45

Gly Tyr Ile Tyr Thr Ser Gly Thr Arg Tyr Arg Ala Asn Trp Ala Arg
     50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                 85                  90                  95

Arg Gly Thr Asp Ile Tyr Asp Tyr Tyr Tyr Trp Val Met Asp Leu Trp
                100                 105                 110

Gly Pro Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
210                 215                 220

Cys Asp Lys Thr His Thr Cys Pro Pro Cys Pro Ala Pro Glu Leu Arg
225                 230                 235                 240

Arg Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Leu His Glu Ala Leu His Ala His Tyr Thr Arg Lys Glu Leu Ser Leu
```

Ser Pro
    450

<210> SEQ ID NO 54
<211> LENGTH: 450
<212> TYPE: PRT
<213> ORGANISM: Artificial Sequence
<220> FEATURE:
<223> OTHER INFORMATION: hT0947AE09H-SG191

<400> SEQUENCE: 54

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Asn Trp Ile Arg Gln Pro Pro Gly Lys Gly Leu Glu Trp Ile
        35                  40                  45

Gly Tyr Ile Tyr Thr Ser Gly Thr Arg Tyr Arg Ala Asn Trp Ala Arg
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Thr Asp Ile Tyr Asp Tyr Tyr Tyr Trp Val Met Asp Leu Trp
            100                 105                 110

Gly Pro Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Arg
225                 230                 235                 240

Arg Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln

```
                340              345              350
Val Tyr Thr Leu Pro Pro Ser Arg Glu Glu Met Thr Lys Asn Gln Val
            355              360              365

Ser Leu Thr Cys Leu Val Lys Gly Phe Tyr Pro Ser Asp Ile Ala Val
    370              375              380

Glu Trp Glu Ser Asn Gly Gln Pro Glu Asn Asn Tyr Lys Thr Thr Pro
385              390              395              400

Pro Val Leu Asp Ser Asp Gly Ser Phe Phe Leu Tyr Ser Lys Leu Thr
                405              410              415

Val Asp Lys Ser Arg Trp Gln Gln Gly Asn Val Phe Ser Cys Ser Val
            420              425              430

Leu His Glu Ala Leu His Ala His Tyr Thr Arg Lys Glu Leu Ser Leu
        435              440              445

Ser Pro
    450

<210> SEQ ID NO 55
<211> LENGTH: 446
<212> TYPE: PRT
<213> ORGANISM: Artificial Sequence
<220> FEATURE:
<223> OTHER INFORMATION: hT0947AE04H-mF18

<400> SEQUENCE: 55

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Asn Trp Ile Arg Gln Pro Pro Gly Lys Gly Leu Glu Trp Ile
        35                  40                  45

Gly Tyr Ile Tyr Thr Ser Gly Thr Thr Tyr His Ala Asn Trp Ala Arg
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Thr Phe Ile Trp Asp Tyr Tyr Tyr Trp Val Met Asp Leu Trp
            100                 105                 110

Gly Pro Gly Thr Leu Val Thr Val Ser Ser Ala Lys Thr Thr Pro Pro
        115                 120                 125

Ser Val Tyr Pro Leu Ala Pro Gly Ser Ala Ala Gln Thr Asn Ser Met
    130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
                165                 170                 175

Ala Val Leu Gln Ser Asp Leu Tyr Thr Leu Ser Ser Ser Val Thr Val
            180                 185                 190

Pro Ser Ser Thr Trp Pro Ser Glu Thr Val Thr Cys Asn Val Ala His
        195                 200                 205

Pro Ala Ser Ser Thr Lys Val Asp Lys Lys Ile Val Pro Arg Asp Cys
    210                 215                 220

Gly Cys Lys Pro Cys Ile Cys Thr Val Lys Glu Val Ser Lys Val Phe
225                 230                 235                 240

Ile Phe Pro Pro Lys Pro Lys Asp Val Leu Thr Ile Thr Leu Thr Pro
```

```
            245                 250                 255
Lys Val Thr Cys Val Val Asp Ile Ser Lys Asp Pro Glu Val
            260                 265                 270

Gln Phe Ser Trp Phe Val Asp Asp Val Glu Val His Thr Ala Gln Thr
            275                 280                 285

Gln Pro Arg Glu Glu Gln Phe Asn Ser Thr Phe Arg Ser Val Ser Glu
        290                 295                 300

Leu Pro Ile Met His Gln Asp Trp Leu Asn Gly Lys Glu Phe Lys Cys
305                 310                 315                 320

Arg Val Asn Ser Ala Ala Phe Pro Ala Pro Ile Glu Lys Thr Ile Ser
                325                 330                 335

Lys Thr Lys Gly Arg Pro Lys Ala Pro Gln Val Tyr Thr Ile Pro Pro
                340                 345                 350

Pro Lys Glu Gln Met Ala Lys Asp Lys Val Ser Leu Thr Cys Met Ile
            355                 360                 365

Thr Asp Phe Phe Pro Glu Asp Ile Thr Val Glu Trp Gln Trp Asn Gly
        370                 375                 380

Gln Pro Ala Glu Asn Tyr Lys Asn Thr Gln Pro Ile Met Asp Thr Asp
385                 390                 395                 400

Gly Ser Tyr Phe Val Tyr Ser Lys Leu Asn Val Gln Lys Ser Asn Trp
                405                 410                 415

Glu Ala Gly Asn Thr Phe Thr Cys Ser Val Leu His Glu Gly Leu His
                420                 425                 430

Asn His His Thr Glu Lys Ser Leu Ser His Ser Pro Gly Lys
                435                 440                 445

<210> SEQ ID NO 56
<211> LENGTH: 446
<212> TYPE: PRT
<213> ORGANISM: Artificial Sequence
<220> FEATURE:
<223> OTHER INFORMATION: hT0947AE07H-mF18

<400> SEQUENCE: 56

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Glu
            20                  25                  30

Ala Met Asn Trp Ile Arg Gln Pro Pro Gly Lys Gly Leu Glu Trp Ile
        35                  40                  45

Gly Tyr Ile Tyr Thr Ser Gly Thr Thr Tyr Arg Ala Asn Trp Ala Arg
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Thr Gly Ile Tyr Asp Tyr Tyr Tyr Trp Val Met Asp Leu Trp
            100                 105                 110

Gly Pro Gly Thr Leu Val Thr Val Ser Ser Ala Lys Thr Thr Pro Pro
        115                 120                 125

Ser Val Tyr Pro Leu Ala Pro Gly Ser Ala Ala Gln Thr Asn Ser Met
    130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
```

```
            165                 170                 175
Ala Val Leu Gln Ser Asp Leu Tyr Thr Leu Ser Ser Val Thr Val
                180                 185                 190

Pro Ser Ser Thr Trp Pro Ser Glu Thr Val Thr Cys Asn Val Ala His
        195                 200                 205

Pro Ala Ser Ser Thr Lys Val Asp Lys Lys Ile Val Pro Arg Asp Cys
210                 215                 220

Gly Cys Lys Pro Cys Ile Cys Thr Val Lys Glu Val Ser Lys Val Phe
225                 230                 235                 240

Ile Phe Pro Pro Lys Pro Lys Asp Val Leu Thr Ile Thr Leu Thr Pro
                245                 250                 255

Lys Val Thr Cys Val Val Val Asp Ile Ser Lys Asp Asp Pro Glu Val
                260                 265                 270

Gln Phe Ser Trp Phe Val Asp Asp Val Glu Val His Thr Ala Gln Thr
            275                 280                 285

Gln Pro Arg Glu Glu Gln Phe Asn Ser Thr Phe Arg Ser Val Ser Glu
        290                 295                 300

Leu Pro Ile Met His Gln Asp Trp Leu Asn Gly Lys Glu Phe Lys Cys
305                 310                 315                 320

Arg Val Asn Ser Ala Ala Phe Pro Ala Pro Ile Glu Lys Thr Ile Ser
                325                 330                 335

Lys Thr Lys Gly Arg Pro Lys Ala Pro Gln Val Tyr Thr Ile Pro Pro
                340                 345                 350

Pro Lys Glu Gln Met Ala Lys Asp Lys Val Ser Leu Thr Cys Met Ile
            355                 360                 365

Thr Asp Phe Phe Pro Glu Asp Ile Thr Val Glu Trp Gln Trp Asn Gly
        370                 375                 380

Gln Pro Ala Glu Asn Tyr Lys Asn Thr Gln Pro Ile Met Asp Thr Asp
385                 390                 395                 400

Gly Ser Tyr Phe Val Tyr Ser Lys Leu Asn Val Gln Lys Ser Asn Trp
                405                 410                 415

Glu Ala Gly Asn Thr Phe Thr Cys Ser Val Leu His Glu Gly Leu His
                420                 425                 430

Asn His His Thr Glu Lys Ser Leu Ser His Ser Pro Gly Lys
            435                 440                 445
```

<210> SEQ ID NO 57
<211> LENGTH: 446
<212> TYPE: PRT
<213> ORGANISM: Artificial Sequence
<220> FEATURE:
<223> OTHER INFORMATION: hT0947AE08H-mF18

<400> SEQUENCE: 57

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Asn Trp Ile Arg Gln Pro Pro Gly Lys Gly Leu Glu Trp Ile
        35                  40                  45

Gly Tyr Ile Tyr Thr Ser Gly Thr Arg Tyr Arg Ala Asn Trp Ala Arg
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
```

```
                85                  90                  95
Arg Gly Thr Asp Ile Tyr Asp Tyr Tyr Tyr Trp Val Met Asp Leu Trp
                100                 105                 110

Gly Pro Gly Thr Leu Val Thr Val Ser Ser Ala Lys Thr Thr Pro Pro
            115                 120                 125

Ser Val Tyr Pro Leu Ala Pro Gly Ser Ala Ala Gln Thr Asn Ser Met
        130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
                165                 170                 175

Ala Val Leu Gln Ser Asp Leu Tyr Thr Leu Ser Ser Ser Val Thr Val
            180                 185                 190

Pro Ser Ser Thr Trp Pro Ser Glu Thr Val Thr Cys Asn Val Ala His
        195                 200                 205

Pro Ala Ser Ser Thr Lys Val Asp Lys Lys Ile Val Pro Arg Asp Cys
210                 215                 220

Gly Cys Lys Pro Cys Ile Cys Thr Val Lys Glu Val Ser Lys Val Phe
225                 230                 235                 240

Ile Phe Pro Pro Lys Pro Lys Asp Val Leu Thr Ile Thr Leu Thr Pro
                245                 250                 255

Lys Val Thr Cys Val Val Asp Ile Ser Lys Asp Asp Pro Glu Val
            260                 265                 270

Gln Phe Ser Trp Phe Val Asp Asp Val Glu Val His Thr Ala Gln Thr
        275                 280                 285

Gln Pro Arg Glu Glu Gln Phe Asn Ser Thr Phe Arg Ser Val Ser Glu
    290                 295                 300

Leu Pro Ile Met His Gln Asp Trp Leu Asn Gly Lys Glu Phe Lys Cys
305                 310                 315                 320

Arg Val Asn Ser Ala Ala Phe Pro Ala Pro Ile Glu Lys Thr Ile Ser
                325                 330                 335

Lys Thr Lys Gly Arg Pro Lys Ala Pro Gln Val Tyr Thr Ile Pro Pro
            340                 345                 350

Pro Lys Glu Gln Met Ala Lys Asp Lys Val Ser Leu Thr Cys Met Ile
        355                 360                 365

Thr Asp Phe Phe Pro Glu Asp Ile Thr Val Glu Trp Gln Trp Asn Gly
    370                 375                 380

Gln Pro Ala Glu Asn Tyr Lys Asn Thr Gln Pro Ile Met Asp Thr Asp
385                 390                 395                 400

Gly Ser Tyr Phe Val Tyr Ser Lys Leu Asn Val Gln Lys Ser Asn Trp
                405                 410                 415

Glu Ala Gly Asn Thr Phe Thr Cys Ser Val Leu His Glu Gly Leu His
            420                 425                 430

Asn His His Thr Glu Lys Ser Leu Ser His Ser Pro Gly Lys
        435                 440                 445

<210> SEQ ID NO 58
<211> LENGTH: 446
<212> TYPE: PRT
<213> ORGANISM: Artificial Sequence
<220> FEATURE:
<223> OTHER INFORMATION: hT0947AE09H-mF18

<400> SEQUENCE: 58

Gln Val Gln Leu Val Glu Ser Gly Gly Gly Val Val Gln Pro Gly Arg
```

-continued

```
1               5                   10                  15
Ser Leu Arg Leu Ser Cys Ala Ala Ser Gly Phe Thr Phe Ser Ser Tyr
            20                  25                  30

Ala Met Asn Trp Ile Arg Gln Pro Gly Lys Gly Leu Glu Trp Ile
        35                  40                  45

Gly Tyr Ile Tyr Thr Ser Gly Thr Arg Tyr Arg Ala Asn Trp Ala Arg
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Gly Thr Asp Ile Tyr Asp Tyr Tyr Tyr Trp Val Met Asp Leu Trp
            100                 105                 110

Gly Pro Gly Thr Leu Val Thr Val Ser Ala Lys Thr Thr Pro Pro
            115                 120                 125

Ser Val Tyr Pro Leu Ala Pro Gly Ser Ala Ala Gln Thr Asn Ser Met
            130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
            165                 170                 175

Ala Val Leu Gln Ser Asp Leu Tyr Thr Leu Ser Ser Ser Val Thr Val
            180                 185                 190

Pro Ser Ser Thr Trp Pro Ser Glu Thr Val Thr Cys Asn Val Ala His
            195                 200                 205

Pro Ala Ser Ser Thr Lys Val Asp Lys Lys Ile Val Pro Arg Asp Cys
210                 215                 220

Gly Cys Lys Pro Cys Ile Cys Thr Val Lys Glu Val Ser Lys Val Phe
225                 230                 235                 240

Ile Phe Pro Pro Lys Pro Lys Asp Val Leu Thr Ile Thr Leu Thr Pro
            245                 250                 255

Lys Val Thr Cys Val Val Val Asp Ile Ser Lys Asp Asp Pro Glu Val
            260                 265                 270

Gln Phe Ser Trp Phe Val Asp Asp Val Glu Val His Thr Ala Gln Thr
            275                 280                 285

Gln Pro Arg Glu Glu Gln Phe Asn Ser Thr Phe Arg Ser Val Ser Glu
            290                 295                 300

Leu Pro Ile Met His Gln Asp Trp Leu Asn Gly Lys Glu Phe Lys Cys
305                 310                 315                 320

Arg Val Asn Ser Ala Ala Phe Pro Ala Pro Ile Glu Lys Thr Ile Ser
                325                 330                 335

Lys Thr Lys Gly Arg Pro Lys Ala Pro Gln Val Tyr Thr Ile Pro Pro
            340                 345                 350

Pro Lys Glu Gln Met Ala Lys Asp Lys Val Ser Leu Thr Cys Met Ile
            355                 360                 365

Thr Asp Phe Phe Pro Glu Asp Ile Thr Val Glu Trp Gln Trp Asn Gly
            370                 375                 380

Gln Pro Ala Glu Asn Tyr Lys Asn Thr Gln Pro Ile Met Asp Thr Asp
385                 390                 395                 400

Gly Ser Tyr Phe Val Tyr Ser Lys Leu Asn Val Gln Lys Ser Asn Trp
                405                 410                 415

Glu Ala Gly Asn Thr Phe Thr Cys Ser Val Leu His Glu Gly Leu His
            420                 425                 430
```

```
Asn His His Thr Glu Lys Ser Leu Ser His Ser Pro Gly Lys
        435                 440                 445

<210> SEQ ID NO 59
<211> LENGTH: 107
<212> TYPE: PRT
<213> ORGANISM: Mus musculus

<400> SEQUENCE: 59

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 60
<211> LENGTH: 215
<212> TYPE: PRT
<213> ORGANISM: Artificial Sequence
<220> FEATURE:
<223> OTHER INFORMATION: hT0947AE04L-SK1

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Tyr
            20                  25                  30

Leu Ala Trp Tyr Gln Gln Lys Pro Gly Gln Pro Pro Lys Leu Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Tyr Ser Asp Ala Asp Ser
                85                  90                  95

Val Gly Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190
```

Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 61
<211> LENGTH: 215
<212> TYPE: PRT
<213> ORGANISM: Artificial Sequence
<220> FEATURE:
<223> OTHER INFORMATION: hT0947AE07L-SK1

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Tyr
            20                  25                  30

Leu Ala Trp Tyr Gln Gln Lys Pro Gly Gln Pro Pro Lys Leu Leu Ile
        35                  40                  45

Tyr Ala Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Tyr Ser Asp Gly Asp Ser
                85                  90                  95

Val Gly Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 62
<211> LENGTH: 215
<212> TYPE: PRT
<213> ORGANISM: Artificial Sequence
<220> FEATURE:
<223> OTHER INFORMATION: hT0947AE08L-SK1

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Tyr
            20                  25                  30

Leu Ala Trp Tyr Gln Gln Lys Pro Gly Gln Pro Pro Lys Leu Leu Ile
        35                  40                  45

Tyr Ala Ala Ser Thr Leu Glu Ser Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Ser Tyr Ser Asp Gly Asp Ser
                 85                  90                  95

Val Gly Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 63
<211> LENGTH: 215
<212> TYPE: PRT
<213> ORGANISM: Artificial Sequence
<220> FEATURE:
<223> OTHER INFORMATION: hT0947AE09L-SK1

<400> SEQUENCE: 63

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Ser Ile Ser Thr Tyr
             20                  25                  30

Leu Ala Trp Tyr Gln Gln Lys Pro Gly Gln Pro Pro Lys Leu Leu Ile
         35                  40                  45

Tyr Ala Ala Ser Thr Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Ser Tyr Ser Asp Ala Asp Ser
                 85                  90                  95

Val Gly Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205
```

-continued

Ser Phe Asn Arg Gly Glu Cys
    210                 215

<210> SEQ ID NO 64
<211> LENGTH: 215
<212> TYPE: PRT
<213> ORGANISM: Artificial Sequence
<220> FEATURE:
<223> OTHER INFORMATION: hT0947AE04L-mk1

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Tyr
            20                  25                  30

Leu Ala Trp Tyr Gln Gln Lys Pro Gly Gln Pro Pro Lys Leu Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Tyr Ser Asp Ala Asp Ser
                85                  90                  95

Val Gly Phe Gly Gln Gly Thr Lys Val Glu Ile Lys Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
    130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
    210                 215

<210> SEQ ID NO 65
<211> LENGTH: 215
<212> TYPE: PRT
<213> ORGANISM: Artificial Sequence
<220> FEATURE:
<223> OTHER INFORMATION: hT0947AE07L-mk1

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Tyr
            20                  25                  30

Leu Ala Trp Tyr Gln Gln Lys Pro Gly Gln Pro Pro Lys Leu Leu Ile
        35                  40                  45

Tyr Ala Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro

```
                65                  70                  75                  80
Glu Asp Phe Ala Thr Tyr Tyr Cys Gln Ser Tyr Ser Asp Gly Asp Ser
                    85                  90                  95

Val Gly Phe Gly Gln Gly Thr Lys Val Glu Ile Lys Arg Ala Asp Ala
                100                 105                 110

Ala Pro Thr Val Ser Ile Phe Pro Pro Ser Ser Glu Gln Leu Thr Ser
                115                 120                 125

Gly Gly Ala Ser Val Val Cys Phe Leu Asn Asn Phe Tyr Pro Lys Asp
            130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
                195                 200                 205

Ser Phe Asn Arg Asn Glu Cys
    210                 215

<210> SEQ ID NO 66
<211> LENGTH: 215
<212> TYPE: PRT
<213> ORGANISM: Artificial Sequence
<220> FEATURE:
<223> OTHER INFORMATION: hT0947AE08L-mk1

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Tyr
                20                  25                  30

Leu Ala Trp Tyr Gln Gln Lys Pro Gly Gln Pro Pro Lys Leu Leu Ile
            35                  40                  45

Tyr Ala Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Tyr Ser Asp Gly Asp Ser
                85                  90                  95

Val Gly Phe Gly Gln Gly Thr Lys Val Glu Ile Lys Arg Ala Asp Ala
                100                 105                 110

Ala Pro Thr Val Ser Ile Phe Pro Pro Ser Ser Glu Gln Leu Thr Ser
                115                 120                 125

Gly Gly Ala Ser Val Val Cys Phe Leu Asn Asn Phe Tyr Pro Lys Asp
            130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
                195                 200                 205

Ser Phe Asn Arg Asn Glu Cys
```

<210> SEQ ID NO 67
<211> LENGTH: 215
<212> TYPE: PRT
<213> ORGANISM: Artificial Sequence
<220> FEATURE:
<223> OTHER INFORMATION: hT0947AE09L-mk1

<400> SEQUENCE: 67

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Tyr
            20                  25                  30

Leu Ala Trp Tyr Gln Gln Lys Pro Gly Gln Pro Pro Lys Leu Leu Ile
        35                  40                  45

Tyr Ala Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Tyr Ser Asp Ala Asp Ser
                85                  90                  95

Val Gly Phe Gly Gln Gly Thr Lys Val Glu Ile Lys Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
    130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
    210                 215
```

<210> SEQ ID NO 68
<211> LENGTH: 390
<212> TYPE: PRT
<213> ORGANISM: Homo sapiens

<400> SEQUENCE: 68

```
Met Pro Pro Ser Gly Leu Arg Leu Leu Pro Leu Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95
```

```
Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
            115                 120                 125

His Ser Ile Tyr Met Phe Phe Asn Thr Ser Glu Leu Arg Glu Ala Val
130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
            195                 200                 205

Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
            325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
    370                 375                 380

Arg Ser Cys Lys Cys Ser
385                 390

<210> SEQ ID NO 69
<211> LENGTH: 1173
<212> TYPE: DNA
<213> ORGANISM: Homo sapiens

<400> SEQUENCE: 69
atgccgccct ccgggctgcg gctgctgccg ctgctgctac cgctgctgtg gctactggtg    60
ctgacgcctg gccggccggc cgcgggacta tccacctgca agactatcga catggagctg    120
gtgaagcgga agcgcatcga ggccatccgc ggccagatcc tgtccaagct gcggctcgcc    180
agccccccga gccaggggga ggtgccgccc ggcccgctgc ccgaggccgt gctcgccctg    240
tacaacagca cccgcgaccg ggtggccggg gagagtgcag aaccggagcc cgagcctgag    300
gccgactact acgccaagga ggtcacccgc gtgctaatgg tggaaaccca caacgaaatc    360
tatgacaagt tcaagcagag tacacacagc atatatatgt tcttcaacac atcagagctc    420
```

-continued

```
cgagaagcgg tacctgaacc cgtgttgctc tcccgggcag agctgcgtct gctgaggctc    480
aagttaaaag tggagcagca cgtggagctg taccagaaat acagcaacaa ttcctggcga    540
tacctcagca accggctgct ggcacccagc gactcgccag agtggttatc ttttgatgtc    600
accggagttg tgcggcagtg gttgagccgt ggaggggaaa ttgagggctt tcgccttagc    660
gcccactgct cctgtgacag cagggataac acactgcaag tggacatcaa cgggttcact    720 accgccgcc gaggtgacct ggccaccatt catggcatga accggccttt cctgcttctc    780
atggccaccc cgctggagag ggcccagcat ctgcaaagct cccggcaccg ccgagccctg    840
gacaccaact attgcttcag ctccacggag aagaactgct gcgtgcggca gctgtacatt    900
gacttccgca aggacctcgg ctggaagtgg atccacgagc ccaagggcta ccatgccaac    960
ttctgcctcg ggcctgccc ctacatttgg agcctggaca cgcagtacag caaggtcctg   1020
gccctgtaca accagcataa cccgggcgcc tcggcggcgc cgtgctgcgt gccgcaggcg   1080
ctggagccgc tgcccatcgt gtactacgtg ggccgcaagc ccaaggtgga gcagctgtcc   1140
aacatgatcg tgcgctcctg caagtgcagc tga                                1173
```

```
<210> SEQ ID NO 70
<211> LENGTH: 390
<212> TYPE: PRT
<213> ORGANISM: Mus musculus

<400> SEQUENCE: 70

Met Pro Pro Ser Gly Leu Arg Leu Leu Pro Leu Leu Pro Leu Pro
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Asp Pro Glu
                85                  90                  95

Pro Glu Pro Glu Ala Asp Tyr Tyr Ala Lys Glu Val Thr Arg Val Leu
            100                 105                 110

Met Val Asp Arg Asn Asn Ala Ile Tyr Glu Lys Thr Lys Asp Ile Ser
        115                 120                 125

His Ser Ile Tyr Met Phe Phe Asn Thr Ser Asp Ile Arg Glu Ala Val
    130                 135                 140

Pro Glu Pro Pro Leu Leu Ser Arg Ala Glu Leu Arg Leu Gln Arg Leu
145                 150                 155                 160

Lys Ser Ser Val Glu Gln His Val Glu Leu Tyr Gln Lys Tyr Ser Asn
                165                 170                 175

Asn Ser Trp Arg Tyr Leu Gly Asn Arg Leu Leu Thr Pro Thr Asp Thr
            180                 185                 190

Pro Glu Trp Leu Ser Phe Asp Val Thr Gly Val Val Arg Gln Trp Leu
        195                 200                 205

Asn Gln Gly Asp Gly Ile Gln Gly Phe Arg Phe Ser Ala His Cys Ser
    210                 215                 220

Cys Asp Ser Lys Asp Asn Lys Leu His Val Glu Ile Asn Gly Ile Ser
225                 230                 235                 240
```

```
Pro Lys Arg Arg Gly Asp Leu Gly Thr Ile His Asp Met Asn Arg Pro
                245                 250                 255

Phe Leu Leu Leu Met Ala Thr Pro Leu Glu Arg Ala Gln His Leu His
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ser Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
    370                 375                 380

Arg Ser Cys Lys Cys Ser
385                 390

<210> SEQ ID NO 71
<211> LENGTH: 1173
<212> TYPE: DNA
<213> ORGANISM: Mus musculus

<400> SEQUENCE: 71
atgccgccct cggggctgcg gctactgccg cttctgctcc cactcccgtg gcttctagtg      60
ctgacgcccg ggaggccagc cgcgggactc tccacctgca agaccatcga catggagctg     120
gtgaaacgga agcgcatcga agccatccgt ggccagatcc tgtccaaact aaggctcgcc     180
agtcccccaa gccaggggga ggtaccgccc ggcccgctgc cgaggcggt gctcgctttg      240 tacaacagca cccgcgaccg ggtggcaggc gagagcgccg acccagagcc ggagcccgaa     300
gcggactact atgctaaaga ggtcacccgc gtgctaatgg tggaccgcaa caacgccatc     360
tatgagaaaa ccaaagacat ctcacacagt atatatatgt tcttcaatac gtcagacatt     420
cgggaagcag tgcccgaacc cccattgctg tcccgtgcag agctgcgctt gcagagatta     480
aaatcaagtg tggagcaaca tgtggaactc taccagaaat atagcaacaa ttcctggcgt     540
taccttggta accggctgct gacccccact gatacgcctg agtggctgtc ttttgacgtc     600
actggagttg tacggcagtg gctgaaccaa ggagacggaa tacagggctt cgattcagc      660 gctcactgct cttgtgacag caaagataac aaactccacg tggaaatcaa cgggatcagc     720
cccaaacgtc gggcgacct gggcaccatc catgacatga accggcctt cctgctcctc       780 atggccaccc ccctggaaag ggcccagcac ctgcacagct cacggcaccg agagccctg      840 gataccaact attgcttcag ctccacagag aagaactgct gtgtgcggca gctgtacatt     900
gactttagga aggacctggg ttggaagtgg atccacgagc caagggcta ccatgccaac      960 ttctgtctgg accctgccc ctatatttgg agcctggaca cacagtacag caaggtcctt     1020
gccctctaca accaacacaa cccgggcgct tcggcgtcac cgtgctgcgt gccgcaggct    1080
ttggagccac tgcccatcgt ctactacgtg gtcgcaagc ccaaggtgga gcagttgtcc    1140
aacatgattg tgcgctcctg caagtgcagc tga                                 1173
```

<210> SEQ ID NO 72
<211> LENGTH: 390
<212> TYPE: PRT
<213> ORGANISM: Macaca fascicularis

<400> SEQUENCE: 72

```
Met Pro Ser Gly Leu Arg Leu Leu Pro Leu Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
            35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
            115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
            195                 200                 205

Ser Arg Gly Gly Glu Ile Glu Gly Phe Arg Leu Ser Ala His Cys Ser
    210                 215                 220

Cys Asp Ser Lys Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
            275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
            355                 360                 365

Tyr Val Gly Arg Lys Pro Lys Val Glu Gln Leu Ser Asn Met Ile Val
    370                 375                 380
```

```
Arg Ser Cys Lys Cys Ser
385             390

<210> SEQ ID NO 73
<211> LENGTH: 1173
<212> TYPE: DNA
<213> ORGANISM: Macaca fascicularis

<400> SEQUENCE: 73
atgccgccct ccgggctgcg gctgctgccg ctgctgctac cgctgctgtg gctactggtg      60
ctgacgcctg gccggccggc cgccggacta tccacctgca agactatcga catggagctg     120
gtgaagcgga agcgcatcga ggccatccgc ggccagatcc tgtccaagct gcggctcgcc     180
agccccccga gccaggggga ggtgccgccc ggcccgctgc ccgaggccgt gctcgccctg     240
tacaacagca cccgcgaccg ggtggccggg gagagtgcgg agccggaacc cgaaccggag     300
gccgactact acgccaagga ggtcacccgc gtgctaatgg tggaaaccca caacgaaatc     360
tatgacaagt tcaagcagag cacacacagc atatatatgt tcttcaacac atcagagctc     420
cgagaagcag tacctgaacc tgtgttgctc tcccgggcag agctgcgtct gctgaggctc     480
aagttaaaag tggagcagca tgtggagctg taccagaaat acagcaacaa ttcctggcga     540
tacctcagca accggctgct ggcgcccagc gactcgccgg agtggttgtc ttttgatgtc     600
accggagttg tgcggcagtg gttgagccgc ggaggggaaa ttgagggctt tcgccttagc     660
gcccactgct cctgtgacag caaagataac acactgcaag tggacatcaa cgggttcact     720
accggccgcc gaggtgacct ggccaccatt catggcatga accggccttt cctgcttctc     780
atggccaccc cgctggagag ggcccaacat ctgcaaagct cccggcaccg ccgagccctg     840
gacaccaact actgcttcag ctccacggag aagaactgct gcgtgcggca gctgtatatt     900
gacttccgca aggacctcgg ctggaagtgg atccacgagc caagggcta ccatgccaac     960
ttctgcctgg accctgccc ctacatttgg agcctggaca cgcagtacag caaggtcctg    1020
gccctgtaca accagcataa cccgggcgcc tcggcggcgc cgtgctgcgt gccgcaggcg    1080
ctggagccgc tgcccatcgt gtactacgtg ggccgcaagc ccaaggtgga gcagctgtcc    1140
aacatgatcg tgcgctcctg caaatgcagc tga                                  1173
```